(12) United States Patent
Salahieh et al.

(10) Patent No.: US 12,329,635 B2
(45) Date of Patent: Jun. 17, 2025

(54) FLARED PROSTHETIC CARDIAC VALVE DELIVERY DEVICES AND SYSTEMS

(71) Applicant: SHIFAMED HOLDINGS, LLC, Campbell, CA (US)

(72) Inventors: Ali Salahieh, Saratoga, CA (US); Connor G. Mulcahy, San Francisco, CA (US); Alice Yang, Campbell, CA (US); Savina Brachthauser Balcells, Los Gatos, CA (US); Mitchell Young, San Francisco, CA (US); Jonathan H. Oakden, San Jose, CA (US); Jasper Adamek-Bowers, San Francisco, CA (US); Cornelius Crowley, San Francisco, CA (US); Terrence Vick, Los Gatos, CA (US); Balvir Johal, San Jose, CA (US); Thu Hoang Pham, San Jose, CA (US)

(73) Assignee: Shifamed Holdings, LLC, Campbell, CA (US)

( * ) Notice: Subject to any disclaimer, the term of this patent is extended or adjusted under 35 U.S.C. 154(b) by 0 days.

(21) Appl. No.: 17/543,555

(22) Filed: Dec. 6, 2021

(65) Prior Publication Data

US 2022/0175522 A1 Jun. 9, 2022

Related U.S. Application Data

(60) Provisional application No. 63/274,821, filed on Nov. 2, 2021, provisional application No. 63/173,281, filed on
(Continued)

(51) Int. Cl.
  *A61F 2/24* (2006.01)
(52) U.S. Cl.
  CPC .... *A61F 2/2418* (2013.01); *A61F 2220/0008* (2013.01); *A61F 2220/0025* (2013.01);
(Continued)

(58) Field of Classification Search
  CPC .... A61F 2/2418; A61F 2/2412; A61F 2/2409; A61F 2/2427; A61F 2/24; A61F 2/07; A61F 2/246; A61F 2250/0039
  See application file for complete search history.

(56) References Cited

U.S. PATENT DOCUMENTS

| | | |
|---|---|---|
| 4,725,274 A | 2/1988 | Lane et al. |
| 5,002,563 A | 3/1991 | Pyka et al. |

(Continued)

FOREIGN PATENT DOCUMENTS

| | | |
|---|---|---|
| AU | 2012261727 B2 | 10/2015 |
| AU | 2019246822 B2 | 8/2020 |

(Continued)

OTHER PUBLICATIONS

Christian Schaefer, Large heart valves—small heart valves, Oct. 19, 2015, ISMAAP (Year: 2015).*
(Continued)

*Primary Examiner* — Seema Mathew
(74) *Attorney, Agent, or Firm* — Shay Glenn LLP

(57) ABSTRACT

A device for treating a diseased native valve in a patient is provided, the device including a frame structure; a valve segment positioned radially within the frame structure, the valve segment comprising a plurality of leaflets, and a plurality of commissure attachment mechanisms coupling the leaflets to the frame structure, each commissure attachment mechanism extending radially inwards from an outflow end of the frame structure as to create a gap between an interior diameter of the outflow end and an outflow edge of the valve segment. Other embodiments and methods of use are also provided.

25 Claims, 32 Drawing Sheets

Related U.S. Application Data on Apr. 9, 2021, provisional application No. 63/121,812, filed on Dec. 4, 2020.

(52) U.S. Cl.
CPC . *A61F 2230/005* (2013.01); *A61F 2230/0078* (2013.01); *A61F 2230/0091* (2013.01); *A61F 2250/0039* (2013.01)

(56) References Cited

U.S. PATENT DOCUMENTS

| | | | |
|---|---|---|---|
| 5,327,905 A | 7/1994 | Avitall | |
| 5,356,424 A | 10/1994 | Buzerak et al. | |
| 5,370,685 A | 12/1994 | Stevens | |
| 5,582,616 A | 12/1996 | Bolduc et al. | |
| 5,716,397 A | 2/1998 | Myers | |
| 5,755,601 A | 5/1998 | Jones | |
| 5,779,669 A | 7/1998 | Haissaguerre et al. | |
| 5,873,835 A | 2/1999 | Hastings et al. | |
| 5,944,690 A | 8/1999 | Falwell et al. | |
| 5,997,526 A | 12/1999 | Giba et al. | |
| 6,048,339 A | 4/2000 | Zirps et al. | |
| 6,053,873 A | 4/2000 | Govari et al. | |
| 6,254,550 B1 | 7/2001 | McNamara et al. | |
| 6,419,695 B1 | 7/2002 | Gabbay | |
| 6,419,696 B1 | 7/2002 | Ortiz et al. | |
| 6,530,952 B2 | 3/2003 | Vesely | |
| 6,533,783 B1 | 3/2003 | Töllner | |
| 6,641,553 B1 | 11/2003 | Chee et al. | |
| 6,752,813 B2 | 6/2004 | Goldfarb et al. | |
| 6,908,478 B2 | 6/2005 | Alferess et al. | |
| 6,964,684 B2 | 11/2005 | Ortiz et al. | |
| 6,974,476 B2 | 12/2005 | McGuckin, Jr. et al. | |
| 7,077,861 B2 | 7/2006 | Spence | |
| 7,101,395 B2 | 9/2006 | Tremulis et al. | |
| 7,125,421 B2 | 10/2006 | Tremulis et al. | |
| 7,160,322 B2 | 1/2007 | Gabbay | |
| 7,175,656 B2 | 2/2007 | Khairkhahan | |
| 7,201,771 B2 | 4/2007 | Lane | |
| 7,226,467 B2 | 6/2007 | Lucatero et al. | |
| 7,381,219 B2 | 1/2008 | Salahieh et al. | |
| 7,329,279 B2 | 2/2008 | Haug et al. | |
| 7,445,631 B2 | 11/2008 | Salahieh et al. | |
| 7,470,285 B2 | 12/2008 | Nugent et al. | |
| 7,527,647 B2 | 5/2009 | Spence | |
| 7,534,261 B2 | 5/2009 | Freidman | |
| 7,563,267 B2 | 7/2009 | Goldfarb et al. | |
| 7,594,903 B2 | 9/2009 | Webler et al. | |
| 7,604,646 B2 | 10/2009 | Goldfarb et al. | |
| 7,608,091 B2 | 10/2009 | Goldfarb et al. | |
| 7,618,449 B2 | 11/2009 | Tremulis et al. | |
| 7,621,948 B2 | 11/2009 | Herrmann et al. | |
| 7,666,204 B2 | 2/2010 | Thornton et al. | |
| 7,704,269 B2 | 4/2010 | St. Goar et al. | |
| 7,731,705 B2 | 6/2010 | Wardle | |
| 7,748,389 B2 | 7/2010 | Salahieh et al. | |
| 7,749,266 B2 | 7/2010 | Forster et al. | |
| 7,780,725 B2 | 8/2010 | Haug et al. | |
| 7,799,069 B2 | 9/2010 | Bailey et al. | |
| 7,811,296 B2 | 10/2010 | Goldfarb et al. | |
| 7,824,442 B2 | 11/2010 | Salahieh et al. | |
| 7,824,443 B2 | 11/2010 | Salahieh et al. | |
| 7,846,203 B2 | 12/2010 | Cribier | |
| 7,942,927 B2 | 5/2011 | Kaye et al. | |
| 7,947,075 B2 | 5/2011 | Goetz et al. | |
| 7,951,195 B2 | 5/2011 | Antonsson et al. | |
| 7,959,666 B2 | 6/2011 | Salahieh et al. | |
| 7,988,724 B2 | 8/2011 | Salahieh et al. | |
| 8,021,421 B2 | 9/2011 | Fogarty et al. | |
| 8,052,749 B2 | 11/2011 | Salahieh et al. | |
| 8,052,750 B2 | 11/2011 | Tuval et al. | |
| 8,062,355 B2 | 11/2011 | Figulla et al. | |
| 8,070,800 B2 | 12/2011 | Lock et al. | |
| 8,075,615 B2 | 12/2011 | Eberhardt et al. | |
| 8,096,985 B2 | 1/2012 | Legaspi et al. | |
| 8,147,541 B2 | 4/2012 | Forster et al. | |
| 8,147,542 B2 | 4/2012 | Maisano et al. | |
| 8,182,528 B2 | 5/2012 | Salahieh et al. | |
| 8,216,256 B2 | 7/2012 | Raschdorf et al. | |
| 8,236,049 B2 | 8/2012 | Rowe et al. | |
| 8,241,351 B2 | 8/2012 | Cabiri | |
| 8,251,977 B2 | 8/2012 | Partlett | |
| 8,252,050 B2 | 8/2012 | Maisano et al. | |
| 8,287,584 B2 | 10/2012 | Salahieh et al. | |
| 8,313,526 B2 | 11/2012 | Hoffman et al. | |
| 8,323,241 B2 | 12/2012 | Salahieh et al. | |
| 8,323,336 B2 | 12/2012 | Hill et al. | |
| 8,328,868 B2 | 12/2012 | Paul et al. | |
| 8,343,213 B2 | 1/2013 | Salahieh et al. | |
| 8,348,995 B2 | 1/2013 | Tuval et al. | |
| 8,348,996 B2 | 1/2013 | Tuval et al. | |
| 8,366,767 B2 | 2/2013 | Zhang | |
| 8,403,981 B2 | 3/2013 | Forster et al. | |
| 8,403,983 B2 | 3/2013 | Quadri et al. | |
| 8,414,643 B2 | 4/2013 | Tuval et al. | |
| 8,414,644 B2 | 4/2013 | Quadri et al. | |
| 8,414,645 B2 | 4/2013 | Dwork et al. | |
| 8,425,593 B2 | 4/2013 | Braido et al. | |
| 8,449,599 B2 | 5/2013 | Chau et al. | |
| 8,454,686 B2 | 6/2013 | Alkhatib | |
| 8,465,541 B2 | 6/2013 | Dwork | |
| 8,500,800 B2 | 8/2013 | Maisano et al. | |
| 8,512,401 B2 | 8/2013 | Murray et al. | |
| 8,523,881 B2 | 9/2013 | Cabiri et al. | |
| 8,545,553 B2 | 10/2013 | Zipory et al. | |
| 8,556,963 B2 | 10/2013 | Tremulis et al. | |
| 8,562,645 B2 | 10/2013 | Stone et al. | |
| 8,562,673 B2 | 10/2013 | Yeung et al. | |
| 8,579,962 B2 | 11/2013 | Salahieh et al. | |
| 8,603,157 B2 | 12/2013 | Seguin et al. | |
| 8,603,160 B2 | 12/2013 | Salahieh et al. | |
| 8,623,075 B2 | 1/2014 | Murray et al. | |
| 8,628,570 B2 | 1/2014 | Seguin | |
| 8,641,727 B2 | 2/2014 | Starksen et al. | |
| 8,652,202 B2 | 2/2014 | Alon et al. | |
| 8,652,203 B2 | 2/2014 | Quadri et al. | |
| 8,657,872 B2 | 2/2014 | Seguin | |
| 8,685,086 B2 | 4/2014 | Navia et al. | |
| 8,696,693 B2 | 4/2014 | Najafi et al. | |
| 8,715,342 B2 | 5/2014 | Zipory et al. | |
| 8,740,976 B2 | 6/2014 | Tran et al. | |
| 8,784,479 B2 | 7/2014 | Antonsson et al. | |
| 8,790,367 B2 | 7/2014 | Nguyen et al. | |
| 8,808,368 B2 | 8/2014 | Maisano et al. | |
| 8,828,078 B2 | 9/2014 | Salahieh et al. | |
| 8,834,564 B2 | 9/2014 | Tuval et al. | |
| 8,840,663 B2 | 9/2014 | Salahieh et al. | |
| 8,840,664 B2 | 9/2014 | Karapetian et al. | |
| 8,845,588 B2 | 9/2014 | Bruszewski | |
| 8,852,271 B2 | 10/2014 | Murray et al. | |
| 8,876,893 B2 | 11/2014 | Dwork et al. | |
| 8,876,894 B2 | 11/2014 | Tuval et al. | |
| 8,876,895 B2 | 11/2014 | Tuval et al. | |
| 8,900,294 B2 | 12/2014 | Paniagua et al. | |
| 8,911,494 B2 | 12/2014 | Hammer et al. | |
| 8,920,369 B2 | 12/2014 | Salahieh et al. | |
| 8,926,690 B2 | 1/2015 | Kovalsky | |
| 8,926,696 B2 | 1/2015 | Cabiri et al. | |
| 8,926,697 B2 | 1/2015 | Gross et al. | |
| 8,940,002 B2 | 1/2015 | Goertzen | |
| 8,940,044 B2 | 1/2015 | Hammer et al. | |
| 8,951,299 B2 | 2/2015 | Paul et al. | |
| 8,986,371 B2 | 3/2015 | Quill et al. | |
| 8,998,980 B2 | 4/2015 | Shipley et al. | |
| 9,005,273 B2 | 4/2015 | Salahleh et al. | |
| 9,011,515 B2 | 4/2015 | Schweich et al. | |
| 9,011,523 B2 | 4/2015 | Seguin | |
| 9,011,530 B2 | 4/2015 | Reich et al. | |
| 9,017,408 B2 | 4/2015 | Siegal et al. | |
| 9,023,100 B2 | 5/2015 | Quadri et al. | |
| 9,034,032 B2 | 5/2015 | McLean et al. | |
| 9,039,757 B2 | 5/2015 | McLean et al. | |
| 9,056,009 B2 | 6/2015 | Keränen | |
| 9,061,120 B2 | 6/2015 | Osypka et al. | |

(56) References Cited

U.S. PATENT DOCUMENTS

| | | | |
|---|---|---|---|
| 9,078,747 | B2 | 7/2015 | Conklin |
| 9,095,431 | B2 | 8/2015 | Yu et al. |
| 9,119,719 | B2 | 9/2015 | Zipory et al. |
| 9,125,739 | B2 | 9/2015 | Paniagua et al. |
| 9,125,740 | B2 | 9/2015 | Morriss et al. |
| 9,155,619 | B2 | 10/2015 | Liu et al. |
| 9,168,129 | B2 | 10/2015 | Valdez et al. |
| 9,168,131 | B2 * | 10/2015 | Yohanan ............ A61F 2/2433 |
| 9,173,713 | B2 | 11/2015 | Hart et al. |
| 9,173,737 | B2 | 11/2015 | Hill et al. |
| 9,180,006 | B2 | 11/2015 | Keränen |
| 9,226,823 | B2 | 1/2016 | Dwork |
| 9,232,995 | B2 * | 1/2016 | Kovalsky ............ A61F 2/2418 |
| 9,277,994 | B2 | 3/2016 | Miller et al. |
| 9,289,297 | B2 | 3/2016 | Wilson et al. |
| 9,295,547 | B2 | 3/2016 | Costello et al. |
| 9,301,756 | B2 | 4/2016 | Wardle |
| 9,301,836 | B2 | 4/2016 | Buchbinder et al. |
| 9,320,597 | B2 | 4/2016 | Savage et al. |
| 9,339,380 | B2 * | 5/2016 | Quadri ............ A61F 2/2409 |
| 9,343,224 | B2 | 5/2016 | Zilbershlag |
| 9,358,110 | B2 | 6/2016 | Paul et al. |
| 9,414,915 | B2 | 8/2016 | Lombardi et al. |
| 9,427,315 | B2 | 8/2016 | Schweich et al. |
| 9,439,757 | B2 | 9/2016 | Wallace et al. |
| 9,468,525 | B2 | 10/2016 | Kovalsky |
| 9,474,606 | B2 | 10/2016 | Zipory et al. |
| 9,474,840 | B2 | 10/2016 | Siess |
| 9,480,559 | B2 | 11/2016 | Vidlund et al. |
| 9,480,560 | B2 * | 11/2016 | Quadri ............ A61F 2/2439 |
| 9,492,273 | B2 | 11/2016 | Wallace et al. |
| 9,526,487 | B2 | 12/2016 | Rahmani |
| 9,526,609 | B2 | 12/2016 | Salahieh et al. |
| 9,532,868 | B2 | 1/2017 | Braido |
| 9,532,870 | B2 | 1/2017 | Cooper et al. |
| 9,561,102 | B2 | 2/2017 | Rust et al. |
| 9,579,198 | B2 | 2/2017 | Deem et al. |
| 9,636,224 | B2 | 5/2017 | Zipory et al. |
| 9,636,481 | B2 | 5/2017 | Campbell et al. |
| 9,662,202 | B2 | 5/2017 | Quill et al. |
| 9,662,206 | B2 | 5/2017 | Börtlein et al. |
| 9,662,209 | B2 | 5/2017 | Gross et al. |
| 9,675,454 | B2 | 6/2017 | Vidlund et al. |
| 9,681,952 | B2 | 6/2017 | Hacohen et al. |
| 9,687,343 | B2 | 6/2017 | Börtlein et al. |
| 9,724,192 | B2 | 8/2017 | Sheps et al. |
| 9,730,790 | B2 | 8/2017 | Quadri et al. |
| 9,730,793 | B2 | 8/2017 | Reich et al. |
| 9,744,031 | B2 | 8/2017 | Girard et al. |
| 9,744,038 | B2 | 8/2017 | Dahlgren et al. |
| 9,750,605 | B2 | 9/2017 | Ganesan et al. |
| 9,763,779 | B2 | 9/2017 | Börtlein et al. |
| 9,763,780 | B2 | 9/2017 | Morriss et al. |
| 9,814,611 | B2 | 11/2017 | Cartledge et al. |
| 9,827,090 | B2 | 11/2017 | Hill et al. |
| 9,861,480 | B2 | 1/2018 | Zakai et al. |
| 9,867,700 | B2 | 1/2018 | Bakis et al. |
| 9,867,702 | B2 | 1/2018 | Keränen et al. |
| 9,877,833 | B1 | 1/2018 | Bishop et al. |
| 9,883,941 | B2 | 2/2018 | Hastings et al. |
| 9,889,003 | B2 | 2/2018 | Börtlein et al. |
| 9,895,221 | B2 | 2/2018 | Vidlund |
| 9,895,222 | B2 | 2/2018 | Zeng et al. |
| 9,901,444 | B2 | 2/2018 | Valdez et al. |
| 9,918,840 | B2 | 3/2018 | Reich et al. |
| D815,744 | S | 4/2018 | Ratz et al. |
| 9,949,825 | B2 | 4/2018 | Braido et al. |
| 9,949,828 | B2 | 4/2018 | Sheps et al. |
| 9,950,142 | B2 | 4/2018 | Eversull et al. |
| 9,968,452 | B2 | 5/2018 | Sheps et al. |
| 9,974,647 | B2 * | 5/2018 | Ganesan ............ A61F 2/2418 |
| 9,974,650 | B2 | 5/2018 | Nguyen-Thien-Nhon et al. |
| 9,999,502 | B2 | 6/2018 | Nasr et al. |
| 9,999,504 | B2 | 6/2018 | Czyscon et al. |
| 10,004,599 | B2 | 6/2018 | Rabito et al. |
| 10,016,271 | B2 | 7/2018 | Morriss et al. |
| 10,016,272 | B2 | 7/2018 | Spence et al. |
| 10,028,832 | B2 | 7/2018 | Quill et al. |
| 10,029,037 | B2 | 7/2018 | Muller et al. |
| 10,034,747 | B2 | 7/2018 | Harewood |
| 10,034,749 | B2 | 7/2018 | Spence et al. |
| 10,039,637 | B2 | 8/2018 | Maimon et al. |
| 10,045,846 | B2 | 8/2018 | Bonyuet et al. |
| 10,052,198 | B2 | 8/2018 | Chau et al. |
| 10,052,199 | B2 | 8/2018 | Spence et al. |
| 10,058,318 | B2 | 8/2018 | Tegzes |
| 10,058,321 | B2 | 8/2018 | Sampson et al. |
| 10,058,424 | B2 * | 8/2018 | Cooper ............ A61F 2/2436 |
| 10,064,719 | B2 | 9/2018 | Börtlein et al. |
| 10,070,954 | B2 | 9/2018 | Braido et al. |
| 10,092,400 | B2 | 10/2018 | Jimenez et al. |
| 10,098,734 | B2 | 10/2018 | Hoang |
| 10,105,217 | B2 | 10/2018 | Keränen |
| 10,105,224 | B2 | 10/2018 | Buchbinder et al. |
| 10,117,744 | B2 * | 11/2018 | Ratz ............ A61F 2/2418 |
| 10,130,464 | B2 | 11/2018 | Meiri et al. |
| 10,130,471 | B2 | 11/2018 | Keränen et al. |
| 10,143,552 | B2 | 12/2018 | Wallace et al. |
| 10,149,756 | B2 * | 12/2018 | Quadri ............ A61F 2/2409 |
| 10,149,759 | B2 | 12/2018 | Naor |
| 10,172,708 | B2 | 1/2019 | Anderson |
| 10,172,711 | B2 | 1/2019 | Keränen |
| 10,179,042 | B2 | 1/2019 | Braido et al. |
| 10,179,044 | B2 * | 1/2019 | Ratz ............ A61F 2/2445 |
| 10,188,514 | B2 * | 1/2019 | Nasr ............ A61F 2/2418 |
| 10,195,021 | B2 | 2/2019 | Keränen et al. |
| 10,195,025 | B2 | 2/2019 | Levi et al. |
| 10,195,027 | B2 | 2/2019 | Nasr |
| 10,195,028 | B2 | 2/2019 | Hosmer et al. |
| 10,195,029 | B2 | 2/2019 | Keränen |
| 10,201,418 | B2 | 2/2019 | Biadillah et al. |
| 10,206,775 | B2 | 2/2019 | Kovalsky et al. |
| 10,213,307 | B2 | 2/2019 | Dwork et al. |
| 10,226,330 | B2 | 3/2019 | Spence et al. |
| 10,226,334 | B2 | 3/2019 | Rowe et al. |
| 10,226,339 | B2 | 3/2019 | Spence et al. |
| 10,238,489 | B2 | 3/2019 | Conklin |
| 10,251,749 | B2 | 4/2019 | Zerkowski et al. |
| 10,258,464 | B2 | 4/2019 | Delaloye et al. |
| 10,258,468 | B2 | 4/2019 | Deem et al. |
| 10,265,169 | B2 | 4/2019 | Desrosiers et al. |
| 10,271,950 | B2 | 4/2019 | Neustadter |
| 10,299,917 | B2 | 5/2019 | Morriss et al. |
| 10,299,921 | B2 | 5/2019 | Dale et al. |
| 10,314,701 | B2 | 6/2019 | Von Segesser et al. |
| 10,321,988 | B2 | 6/2019 | Gorman et al. |
| 10,321,989 | B2 | 6/2019 | Keränen |
| 10,327,743 | B2 | 6/2019 | St. Goar et al. |
| 10,327,766 | B2 | 6/2019 | Zerkowski et al. |
| 10,335,277 | B2 | 7/2019 | Crisostomo et al. |
| 10,338,724 | B2 | 7/2019 | Zhao |
| 10,350,066 | B2 | 7/2019 | Cooper et al. |
| 10,357,351 | B2 | 7/2019 | Cooper et al. |
| 10,357,634 | B2 | 7/2019 | Simmons et al. |
| 10,363,130 | B2 | 7/2019 | Armer et al. |
| 10,363,131 | B2 | 7/2019 | Eidenschink et al. |
| 10,368,986 | B2 | 8/2019 | Gosal et al. |
| 10,368,990 | B2 | 8/2019 | Noe et al. |
| 10,376,266 | B2 | 8/2019 | Herman et al. |
| 10,376,360 | B2 | 8/2019 | Bruchman et al. |
| 10,376,363 | B2 | 8/2019 | Quadri et al. |
| 10,398,547 | B2 | 9/2019 | Li et al. |
| 10,426,605 | B2 * | 10/2019 | Ma ............ A61F 2/2418 |
| 10,426,608 | B2 | 10/2019 | Salahieh et al. |
| 10,433,961 | B2 | 10/2019 | McLean |
| 10,470,881 | B2 | 11/2019 | Noe et al. |
| 10,478,291 | B2 | 11/2019 | Nguyen et al. |
| 10,500,048 | B2 | 12/2019 | Khairkhahan et al. |
| 10,507,104 | B2 | 12/2019 | Zhang et al. |
| 10,512,541 | B2 | 12/2019 | Zerkowski et al. |
| 10,524,901 | B2 | 1/2020 | Quadri et al. |
| 10,548,729 | B2 | 2/2020 | Zipory et al. |
| 10,568,737 | B2 | 2/2020 | Noe et al. |
| 10,575,951 | B2 | 3/2020 | Johnson et al. |

(56) References Cited

U.S. PATENT DOCUMENTS

| | | |
|---|---|---|
| 10,603,165 B2 | 3/2020 | Maimon et al. |
| 10,639,143 B2 * | 5/2020 | Oba .................. A61F 2/2409 |
| 10,639,154 B2 | 5/2020 | Seguin |
| 10,653,524 B2 | 5/2020 | Khairkhahan et al. |
| 10,660,753 B2 | 5/2020 | Pham et al. |
| 10,687,938 B2 | 6/2020 | Patel et al. |
| 10,695,160 B2 | 6/2020 | Lashinski et al. |
| 10,702,386 B2 | 7/2020 | Khairkhahan et al. |
| 10,709,552 B2 | 7/2020 | Backus et al. |
| 10,716,662 B2 | 7/2020 | Delaloye et al. |
| 10,722,351 B2 | 7/2020 | Griffin et al. |
| 10,722,352 B2 | 7/2020 | Spence |
| 10,722,353 B2 | 7/2020 | Levi |
| 10,729,542 B2 | 8/2020 | Howard et al. |
| 10,743,991 B2 | 8/2020 | Brown |
| 10,751,180 B2 | 8/2020 | Schewel |
| 10,751,184 B2 | 8/2020 | Reich et al. |
| 10,765,514 B2 | 9/2020 | Iflah et al. |
| 10,813,749 B2 | 10/2020 | Nguyen et al. |
| 10,828,153 B2 | 11/2020 | Noe et al. |
| 10,856,970 B2 | 12/2020 | Tuval et al. |
| 10,869,755 B2 | 12/2020 | Granada et al. |
| 10,888,420 B2 | 1/2021 | Bateman et al. |
| 10,888,421 B2 * | 1/2021 | Hariton .................. A61F 2/24 |
| 10,912,644 B2 | 2/2021 | Argento et al. |
| 10,973,629 B2 | 4/2021 | Levi et al. |
| 10,973,630 B2 | 4/2021 | Torrianni et al. |
| 11,007,057 B2 | 5/2021 | Pham et al. |
| 11,020,221 B2 | 6/2021 | Arcaro et al. |
| 11,039,922 B2 | 6/2021 | Konno |
| 11,051,934 B2 * | 7/2021 | Cooper .................. A61F 2/2439 |
| 11,051,935 B2 * | 7/2021 | Schweich, Jr. ........... A61F 2/24 |
| 11,147,670 B2 | 10/2021 | Hayoz et al. |
| 11,234,818 B2 | 2/2022 | Zerkowski et al. |
| 11,547,563 B2 | 1/2023 | Keränen et al. |
| 11,759,318 B2 * | 9/2023 | Vidlund .................. A61F 2/2418 623/1.14 |
| 2002/0173841 A1 | 11/2002 | Ortiz et al. |
| 2003/0114913 A1 * | 6/2003 | Spenser .................. A61F 2/2436 623/2.14 |
| 2003/0233142 A1 | 12/2003 | Morales et al. |
| 2004/0039442 A1 | 2/2004 | St. Goar et al. |
| 2004/0044350 A1 | 3/2004 | Martin et al. |
| 2005/0137686 A1 | 6/2005 | Salahieh et al. |
| 2005/0137687 A1 | 6/2005 | Salahieh et al. |
| 2005/0137691 A1 | 6/2005 | Salahieh et al. |
| 2005/0137694 A1 | 6/2005 | Haug et al. |
| 2005/0137696 A1 | 6/2005 | Salahieh et al. |
| 2005/0165344 A1 | 7/2005 | Dobak |
| 2005/0240202 A1 | 10/2005 | Shennib et al. |
| 2005/0277839 A1 | 12/2005 | Alderman et al. |
| 2006/0009841 A1 | 1/2006 | McGuckin et al. |
| 2006/0052821 A1 | 3/2006 | Abbot et al. |
| 2006/0074484 A1 | 4/2006 | Huber |
| 2006/0178700 A1 | 8/2006 | Quinn |
| 2006/0195134 A1 | 8/2006 | Crittenden |
| 2006/0217762 A1 | 9/2006 | Maahs et al. |
| 2006/0259136 A1 | 11/2006 | Nguyen et al. |
| 2006/0293698 A1 | 12/2006 | Douk |
| 2007/0027533 A1 | 2/2007 | Douk |
| 2007/0038292 A1 | 2/2007 | Danielpour |
| 2007/0051377 A1 | 3/2007 | Douk et al. |
| 2007/0055206 A1 | 3/2007 | To et al. |
| 2007/0118151 A1 | 5/2007 | Davidson |
| 2007/0142907 A1 | 6/2007 | Moaddeb et al. |
| 2007/0185572 A1 | 8/2007 | Solem et al. |
| 2007/0255396 A1 | 11/2007 | Douk et al. |
| 2007/0293724 A1 | 12/2007 | Saadat et al. |
| 2007/0293943 A1 | 12/2007 | Quinn |
| 2008/0004696 A1 | 1/2008 | Vesely |
| 2008/0004697 A1 | 1/2008 | Lichtenstein et al. |
| 2008/0200980 A1 | 8/2008 | Robin et al. |
| 2008/0208327 A1 | 8/2008 | Rowe |
| 2008/0275503 A1 | 11/2008 | Spence et al. |
| 2008/0275540 A1 | 11/2008 | Wen |
| 2009/0030504 A1 | 1/2009 | Weber et al. |
| 2009/0088836 A1 | 4/2009 | Bishop et al. |
| 2009/0093826 A1 | 4/2009 | Warder-Gabaldon |
| 2009/0138079 A1 | 5/2009 | Tuval et al. |
| 2009/0157174 A1 | 6/2009 | Yoganathan et al. |
| 2009/0192601 A1 * | 7/2009 | Rafiee .................. A61F 2/2436 623/2.11 |
| 2009/0209950 A1 | 8/2009 | Starksen |
| 2009/0222026 A1 | 9/2009 | Rothstein et al. |
| 2009/0276040 A1 | 11/2009 | Rowe et al. |
| 2009/0299471 A1 | 12/2009 | Keranen |
| 2010/0010520 A1 | 1/2010 | Takahashi et al. |
| 2010/0049239 A1 | 2/2010 | McGuckin, Jr. et al. |
| 2010/0076497 A1 | 3/2010 | Zwirkoski |
| 2010/0076549 A1 | 3/2010 | Keidar et al. |
| 2010/0094406 A1 | 4/2010 | Leprince et al. |
| 2010/0185172 A1 | 7/2010 | Fabro |
| 2010/0198056 A1 | 8/2010 | Fabro et al. |
| 2010/0198192 A1 | 8/2010 | Serina et al. |
| 2010/0198208 A1 | 8/2010 | Napp et al. |
| 2010/0217385 A1 | 8/2010 | Thompson et al. |
| 2010/0312333 A1 | 12/2010 | Navia et al. |
| 2011/0022164 A1 | 1/2011 | Quinn et al. |
| 2011/0040366 A1 | 2/2011 | Goetz et al. |
| 2011/0046600 A1 | 2/2011 | Crank |
| 2011/0208298 A1 * | 8/2011 | Tuval .................. A61F 2/2418 623/2.17 |
| 2011/0224785 A1 | 9/2011 | Hacohen |
| 2011/0245911 A1 | 10/2011 | Quill et al. |
| 2011/0288637 A1 | 11/2011 | De Marchena |
| 2011/0295363 A1 * | 12/2011 | Girard .................. A61F 2/2412 623/1.26 |
| 2011/0313515 A1 | 12/2011 | Quadri et al. |
| 2011/0319989 A1 | 12/2011 | Lane et al. |
| 2012/0022633 A1 | 1/2012 | Olson et al. |
| 2012/0053680 A1 | 3/2012 | Bolling et al. |
| 2012/0053682 A1 * | 3/2012 | Kovalsky .............. A61F 2/2418 623/2.11 |
| 2012/0143316 A1 | 6/2012 | Seguin et al. |
| 2012/0197388 A1 | 8/2012 | Khairkhahan et al. |
| 2012/0203333 A1 | 8/2012 | McGuckin, Jr. et al. |
| 2012/0221101 A1 | 8/2012 | Moaddeb et al. |
| 2012/0277734 A1 | 11/2012 | Geotz et al. |
| 2012/0277853 A1 | 11/2012 | Rothstein |
| 2013/0006352 A1 | 1/2013 | Yaron |
| 2013/0023985 A1 | 1/2013 | Khairkhahan et al. |
| 2013/0035758 A1 | 2/2013 | Seguin et al. |
| 2013/0079873 A1 | 3/2013 | Migliazza et al. |
| 2013/0116779 A1 | 5/2013 | Weber |
| 2013/0123912 A1 | 5/2013 | Tung et al. |
| 2013/0172992 A1 | 7/2013 | Gross et al. |
| 2013/0253643 A1 | 9/2013 | Rolando et al. |
| 2013/0274873 A1 | 10/2013 | Delaloye et al. |
| 2013/0282113 A1 * | 10/2013 | Punga .................. A61F 2/2418 623/2.17 |
| 2013/0304200 A1 * | 11/2013 | McLean .................. A61F 2/2418 623/2.18 |
| 2013/0325110 A1 | 12/2013 | Khalil et al. |
| 2013/0331931 A1 * | 12/2013 | Gregg .................. A61F 2/2412 623/2.11 |
| 2014/0005768 A1 | 1/2014 | Thomas et al. |
| 2014/0031928 A1 | 1/2014 | Murphy et al. |
| 2014/0081154 A1 | 5/2014 | Toth |
| 2014/0194983 A1 * | 7/2014 | Kovalsky .............. A61F 2/2418 623/2.38 |
| 2014/0200649 A1 | 7/2014 | Essinger et al. |
| 2014/0222136 A1 * | 8/2014 | Geist .................. A61F 2/2436 623/2.37 |
| 2014/0222142 A1 * | 8/2014 | Kovalsky .............. A61F 2/2418 623/2.17 |
| 2014/0228943 A1 | 8/2014 | Stigall et al. |
| 2014/0249621 A1 | 9/2014 | Eidenschink |
| 2014/0257467 A1 | 9/2014 | Lane et al. |
| 2014/0277382 A1 | 9/2014 | Dolan et al. |
| 2014/0277409 A1 | 9/2014 | Börtlein et al. |
| 2014/0277427 A1 * | 9/2014 | Ratz .................. A61F 2/2409 623/2.38 |

(56) References Cited

U.S. PATENT DOCUMENTS

| | | | |
|---|---|---|---|
| 2014/0296966 A1* | 10/2014 | Braido | A61F 2/915 623/1.26 |
| 2014/0324163 A1 | 10/2014 | Keränen et al. | |
| 2014/0350669 A1* | 11/2014 | Gillespie | A61F 2/2442 623/2.18 |
| 2015/0005764 A1 | 1/2015 | Hanson et al. | |
| 2015/0005874 A1* | 1/2015 | Vidlund | A61F 2/2412 623/2.14 |
| 2015/0018876 A1 | 1/2015 | Ewers et al. | |
| 2015/0051709 A1 | 2/2015 | Vasquez et al. | |
| 2015/0094802 A1* | 4/2015 | Buchbinder | A61F 2/2454 623/2.38 |
| 2015/0134055 A1 | 5/2015 | Spence et al. | |
| 2015/0173897 A1 | 6/2015 | Raanani et al. | |
| 2015/0250480 A1 | 9/2015 | Featherstone | |
| 2015/0257879 A1* | 9/2015 | Bortlein | A61F 2/2418 623/2.11 |
| 2015/0265403 A1 | 9/2015 | Keränen | |
| 2015/0272737 A1 | 10/2015 | Dale et al. | |
| 2015/0297346 A1 | 10/2015 | Duffy et al. | |
| 2015/0305863 A1 | 10/2015 | Gray et al. | |
| 2015/0328000 A1 | 11/2015 | Ratz et al. | |
| 2015/0335290 A1 | 11/2015 | Hunter | |
| 2015/0335426 A1 | 11/2015 | Lim et al. | |
| 2015/0351735 A1 | 12/2015 | Keränen et al. | |
| 2015/0351908 A1 | 12/2015 | Keränen et al. | |
| 2015/0351911 A1 | 12/2015 | Keränen et al. | |
| 2016/0089126 A1 | 3/2016 | Guo | |
| 2016/0095705 A1 | 4/2016 | Keränen et al. | |
| 2016/0113764 A1 | 4/2016 | Sheahan et al. | |
| 2016/0113766 A1* | 4/2016 | Ganesan | A61F 2/2436 623/2.11 |
| 2016/0143689 A1 | 5/2016 | Ditter | |
| 2016/0143731 A1 | 5/2016 | Backus et al. | |
| 2016/0151153 A1* | 6/2016 | Sandstrom | A61F 2/2418 623/2.18 |
| 2016/0166380 A1 | 6/2016 | Seguin et al. | |
| 2016/0206853 A1 | 7/2016 | Bolduc et al. | |
| 2016/0228247 A1 | 8/2016 | Maimon et al. | |
| 2016/0235526 A1 | 8/2016 | Lashinski et al. | |
| 2016/0235529 A1 | 8/2016 | Ma et al. | |
| 2016/0324637 A1 | 11/2016 | Hlavka et al. | |
| 2016/0324639 A1 | 11/2016 | Nguyen et al. | |
| 2016/0331523 A1 | 11/2016 | Chau et al. | |
| 2016/0346080 A1 | 12/2016 | Righini et al. | |
| 2017/0056163 A1 | 3/2017 | Tayeb et al. | |
| 2017/0071732 A1 | 3/2017 | Conklin et al. | |
| 2017/0079790 A1 | 3/2017 | Vidlund et al. | |
| 2017/0095328 A1* | 4/2017 | Cooper | A61F 2/2418 |
| 2017/0112624 A1 | 4/2017 | Patel | |
| 2017/0119524 A1 | 5/2017 | Salahich et al. | |
| 2017/0128203 A1 | 5/2017 | Zhang et al. | |
| 2017/0156723 A1 | 6/2017 | Keating et al. | |
| 2017/0165054 A1* | 6/2017 | Benson | A61F 2/2418 |
| 2017/0165057 A9 | 6/2017 | Morriss et al. | |
| 2017/0189177 A1 | 7/2017 | Schweich et al. | |
| 2017/0216025 A1 | 8/2017 | Nitzan et al. | |
| 2017/0245850 A1 | 8/2017 | Call et al. | |
| 2017/0258585 A1 | 9/2017 | Marquez et al. | |
| 2017/0273788 A1 | 9/2017 | O'Carroll et al. | |
| 2017/0273789 A1 | 9/2017 | Yaron et al. | |
| 2017/0281341 A1 | 10/2017 | Lim et al. | |
| 2017/0311937 A1 | 11/2017 | Bambury et al. | |
| 2017/0348099 A1 | 12/2017 | Mendelson et al. | |
| 2018/0014931 A1* | 1/2018 | Morriss | A61F 2/2418 |
| 2018/0021546 A1 | 1/2018 | McDermott et al. | |
| 2018/0049873 A1 | 2/2018 | Manash et al. | |
| 2018/0055628 A1 | 3/2018 | Patel et al. | |
| 2018/0092763 A1 | 4/2018 | Dagan et al. | |
| 2018/0110622 A1 | 4/2018 | Gregg et al. | |
| 2018/0116790 A1 | 5/2018 | Ratz et al. | |
| 2018/0125648 A1* | 5/2018 | Nasr | A61F 2/2415 |
| 2018/0125649 A1* | 5/2018 | Nasr | A61F 2/2415 |
| 2018/0125650 A1* | 5/2018 | Nasr | A61F 2/2418 |
| 2018/0125651 A1* | 5/2018 | Nasr | A61F 2/2418 |
| 2018/0133003 A1 | 5/2018 | Levi | |
| 2018/0177592 A1 | 6/2018 | Benichou et al. | |
| 2018/0177594 A1 | 6/2018 | Patel et al. | |
| 2018/0206982 A1 | 7/2018 | Haivatov et al. | |
| 2018/0206986 A1* | 7/2018 | Noe | A61F 2/2412 |
| 2018/0206992 A1 | 7/2018 | Brown | |
| 2018/0207395 A1 | 7/2018 | Bulman et al. | |
| 2018/0214267 A1 | 8/2018 | Lally et al. | |
| 2018/0214270 A1 | 8/2018 | Subramanian et al. | |
| 2018/0221014 A1 | 8/2018 | Darabian | |
| 2018/0228608 A1 | 8/2018 | Sheps et al. | |
| 2018/0228610 A1 | 8/2018 | Lashinski et al. | |
| 2018/0235443 A1 | 8/2018 | Smith et al. | |
| 2018/0250126 A1 | 9/2018 | O'Connor et al. | |
| 2018/0250132 A1 | 9/2018 | Ketai et al. | |
| 2018/0263764 A1 | 9/2018 | Manash et al. | |
| 2018/0280171 A1 | 10/2018 | Gloss et al. | |
| 2018/0289473 A1 | 10/2018 | Rajagopal et al. | |
| 2018/0289474 A1 | 10/2018 | Rajagopal et al. | |
| 2018/0289478 A1 | 10/2018 | Quill | |
| 2018/0289480 A1 | 10/2018 | D'ambra et al. | |
| 2018/0289485 A1 | 10/2018 | Rajagopal et al. | |
| 2018/0296335 A1 | 10/2018 | Miyashiro | |
| 2018/0296338 A1 | 10/2018 | Rabito et al. | |
| 2018/0296341 A1* | 10/2018 | Noe | A61F 2/2412 |
| 2018/0318079 A1 | 11/2018 | Patel et al. | |
| 2018/0325665 A1* | 11/2018 | Gurovich | A61F 2/2418 |
| 2018/0333259 A1 | 11/2018 | Dibie | |
| 2018/0344303 A1 | 12/2018 | Bambury et al. | |
| 2018/0344454 A1 | 12/2018 | Mauch et al. | |
| 2018/0344459 A1 | 12/2018 | Spence et al. | |
| 2018/0344971 A1 | 12/2018 | Suzuki et al. | |
| 2018/0360600 A1 | 12/2018 | Zhuang et al. | |
| 2018/0368830 A1 | 12/2018 | O'Carroll et al. | |
| 2019/0000615 A1* | 1/2019 | Tayeb | A61F 2/9522 |
| 2019/0000625 A1 | 1/2019 | O'Carroll et al. | |
| 2019/0008635 A1 | 1/2019 | Francis et al. | |
| 2019/0008639 A1 | 1/2019 | Landon et al. | |
| 2019/0008640 A1 | 1/2019 | Cooper et al. | |
| 2019/0015205 A1 | 1/2019 | Rajagopal et al. | |
| 2019/0021859 A1 | 1/2019 | O'Carrol et al. | |
| 2019/0046315 A1 | 2/2019 | Gao et al. | |
| 2019/0053894 A1 | 2/2019 | Levi et al. | |
| 2019/0053895 A1 | 2/2019 | Levi | |
| 2019/0053898 A1 | 2/2019 | Maimon et al. | |
| 2019/0053899 A1 | 2/2019 | Levi | |
| 2019/0053903 A1 | 2/2019 | Rohl et al. | |
| 2019/0060068 A1 | 2/2019 | Cope et al. | |
| 2019/0060069 A1 | 2/2019 | Maimon et al. | |
| 2019/0060071 A1 | 2/2019 | Lane et al. | |
| 2019/0076244 A1 | 3/2019 | Yohanan et al. | |
| 2019/0076664 A1 | 3/2019 | Ollivier | |
| 2019/0091014 A1* | 3/2019 | Arcaro | A61F 2/2433 |
| 2019/0117392 A1 | 4/2019 | Quadri et al. | |
| 2019/0133756 A1 | 5/2019 | Zhang et al. | |
| 2019/0133757 A1 | 5/2019 | Zhang et al. | |
| 2019/0142589 A1 | 5/2019 | Basude | |
| 2019/0159770 A1 | 5/2019 | Rohl et al. | |
| 2019/0160292 A1 | 5/2019 | Peichel et al. | |
| 2019/0167425 A1 | 6/2019 | Reich et al. | |
| 2019/0183649 A1 | 6/2019 | Allen et al. | |
| 2019/0192288 A1 | 6/2019 | Levi et al. | |
| 2019/0192296 A1 | 6/2019 | Schwartz et al. | |
| 2019/0201191 A1 | 7/2019 | McLean et al. | |
| 2019/0209311 A1 | 7/2019 | Zhang et al. | |
| 2019/0209312 A1 | 7/2019 | Zhang et al. | |
| 2019/0209313 A1 | 7/2019 | Zhang et al. | |
| 2019/0209314 A1 | 7/2019 | Zhang et al. | |
| 2019/0209315 A1 | 7/2019 | Zhang et al. | |
| 2019/0209316 A1 | 7/2019 | Zhang et al. | |
| 2019/0209317 A1 | 7/2019 | Zhang et al. | |
| 2019/0209318 A1 | 7/2019 | Zhang et al. | |
| 2019/0209320 A1 | 7/2019 | Drasler et al. | |
| 2019/0231520 A1 | 8/2019 | Desrosiers et al. | |
| 2019/0240023 A1 | 8/2019 | Spence et al. | |
| 2019/0246916 A1 | 8/2019 | Kuraguntla et al. | |
| 2019/0254816 A1 | 8/2019 | Anderson et al. | |
| 2019/0261995 A1 | 8/2019 | Goldfarb et al. | |

(56) References Cited

U.S. PATENT DOCUMENTS

| | | |
|---|---|---|
| 2019/0261996 A1 | 8/2019 | Goldfarb et al. |
| 2019/0261997 A1 | 8/2019 | Goldfarb et al. |
| 2019/0262129 A1 | 8/2019 | Cooper et al. |
| 2019/0282237 A1 | 9/2019 | Goldfarb et al. |
| 2019/0328515 A1* | 10/2019 | Peterson ............... A61F 2/2409 |
| 2019/0328518 A1 | 10/2019 | Neumann |
| 2019/0336282 A1 | 11/2019 | Christianson et al. |
| 2019/0343625 A1 | 11/2019 | Gharib et al. |
| 2019/0365530 A1 | 12/2019 | Hoang et al. |
| 2019/0374337 A1 | 12/2019 | Zamani et al. |
| 2019/0374342 A1 | 12/2019 | Gregg et al. |
| 2020/0000579 A1 | 1/2020 | Manash et al. |
| 2020/0000586 A1 | 1/2020 | Tian et al. |
| 2020/0008936 A1 | 1/2020 | Cheema et al. |
| 2020/0022811 A1 | 1/2020 | Griswold et al. |
| 2020/0054453 A1 | 2/2020 | Zerkowski et al. |
| 2020/0060813 A1 | 2/2020 | Nguyen et al. |
| 2020/0060820 A1 | 2/2020 | Ben-Zvi et al. |
| 2020/0060852 A1 | 2/2020 | Argento et al. |
| 2020/0069415 A1* | 3/2020 | Bialas .................. A61F 2/2445 |
| 2020/0078000 A1 | 3/2020 | Rajagopal et al. |
| 2020/0093601 A1 | 3/2020 | Neustadter |
| 2020/0107932 A1 | 4/2020 | Rabito et al. |
| 2020/0107933 A1 | 4/2020 | Oba |
| 2020/0113586 A1 | 4/2020 | Karasic et al. |
| 2020/0113685 A1 | 4/2020 | Miller et al. |
| 2020/0113696 A1 | 4/2020 | Ekvall et al. |
| 2020/0138575 A1 | 5/2020 | Tuval |
| 2020/0139082 A1 | 5/2020 | Matlock |
| 2020/0178977 A1 | 6/2020 | Coleman et al. |
| 2020/0188107 A1 | 6/2020 | Gloss et al. |
| 2020/0205800 A1 | 7/2020 | Gilmore et al. |
| 2020/0205969 A1 | 7/2020 | Hacohen |
| 2020/0205974 A1 | 7/2020 | Zerkowski et al. |
| 2020/0205975 A1 | 7/2020 | Khairkhahan |
| 2020/0205979 A1 | 7/2020 | O'Carroll et al. |
| 2020/0214708 A1 | 7/2020 | Sharma |
| 2020/0229806 A1 | 7/2020 | Goldfarb et al. |
| 2020/0229918 A1 | 7/2020 | Pham et al. |
| 2020/0261220 A1 | 8/2020 | Argento et al. |
| 2020/0275921 A1 | 9/2020 | Gilmore et al. |
| 2020/0276017 A1 | 9/2020 | Subramanian et al. |
| 2020/0297489 A1 | 9/2020 | Bishop et al. |
| 2020/0297491 A1 | 9/2020 | Argento et al. |
| 2020/0323637 A1* | 10/2020 | Banai .................. A61F 2/2436 |
| 2020/0352705 A1 | 11/2020 | Heneghan et al. |
| 2020/0352706 A1 | 11/2020 | Campbell |
| 2020/0360139 A1 | 11/2020 | Hammer et al. |
| 2021/0022854 A1 | 1/2021 | Zhao et al. |
| 2021/0022860 A1 | 1/2021 | Lally et al. |
| 2021/0030536 A1 | 2/2021 | Kaleta |
| 2021/0121289 A1 | 4/2021 | Bruchman et al. |
| 2021/0128297 A1 | 5/2021 | Braido et al. |
| 2021/0145573 A1 | 5/2021 | Dasi et al. |
| 2021/0154009 A1 | 5/2021 | Argento et al. |
| 2021/0161688 A1 | 6/2021 | Shahriari |
| 2021/0177583 A1 | 6/2021 | Colavito et al. |
| 2021/0177584 A1 | 6/2021 | Levi et al. |
| 2021/0177587 A1 | 6/2021 | Braido |
| 2021/0186689 A1 | 6/2021 | Eidenschink et al. |
| 2021/0228343 A1 | 7/2021 | Scheinblum et al. |
| 2021/0315693 A1* | 10/2021 | Tabor ..................... A61F 2/07 |
| 2021/0338419 A1* | 11/2021 | Gifford, III ........... A61F 2/2409 |
| 2021/0378823 A1 | 12/2021 | Argento et al. |
| 2021/0386542 A1* | 12/2021 | Schankereli .......... A61F 2/2436 |
| 2021/0401572 A1 | 12/2021 | Nasar et al. |
| 2022/0054261 A1* | 2/2022 | Argento .................. A61F 2/95 |
| 2022/0257373 A1 | 8/2022 | Yang et al. |
| 2022/0387755 A1 | 12/2022 | Higgins |
| 2022/0401214 A1 | 12/2022 | Saul |
| 2023/0028648 A1* | 1/2023 | Neuberger ............ A61F 2/2418 |
| 2023/0044256 A1 | 2/2023 | Salahieh |
| 2023/0105492 A1 | 4/2023 | Argento et al. |
| 2023/0118748 A1 | 4/2023 | Argento |
| 2023/0165679 A1 | 6/2023 | Boyd et al. |
| 2023/0225861 A1* | 7/2023 | Argento ................ A61F 2/2418 623/2.17 |
| 2023/0240839 A1* | 8/2023 | Corona ................. A61F 2/2436 623/2.1 |
| 2023/0277317 A1 | 9/2023 | Argento et al. |
| 2023/0320845 A1* | 10/2023 | Salahieh ............... A61F 2/2418 623/2.18 |
| 2024/0148497 A1* | 5/2024 | Bukin .................. A61F 2/2436 |
| 2024/0164895 A1* | 5/2024 | Mai ....................... A61F 2/2418 |
| 2024/0285396 A1 | 8/2024 | Schwartz et al. |
| 2024/0293217 A1 | 9/2024 | Cartledge et al. |
| 2024/0374378 A1 | 11/2024 | Adamek-Bowers et al. |
| 2024/0390144 A1 | 11/2024 | Adamek-Bowers et al. |
| 2024/0415652 A1* | 12/2024 | Stearns ................. A61F 2/246 |

FOREIGN PATENT DOCUMENTS

| | | |
|---|---|---|
| AU | 2020227034 A1 | 9/2020 |
| BR | PI0820603 B1 | 6/2020 |
| CA | 2979817 A1 | 9/2016 |
| CA | 2954826 C | 10/2019 |
| CN | 103764216 A | 4/2014 |
| CN | 103974670 A | 8/2014 |
| CN | 105358098 A | 2/2016 |
| CN | 107690323 A | 2/2018 |
| CN | 111110401 A | 5/2020 |
| CN | 111110403 A | 5/2020 |
| CN | 108601655 B | 6/2020 |
| CN | 111265335 A | 6/2020 |
| CN | 111278389 A | 6/2020 |
| CN | 111329541 A | 6/2020 |
| DE | 19857887 B4 | 5/2005 |
| DE | 102014102650 A1 | 9/2015 |
| EP | 1105181 B1 | 2/2004 |
| EP | 1432369 B1 | 2/2008 |
| EP | 2374415 A1 | 10/2011 |
| EP | 2907479 A1 | 8/2015 |
| EP | 3037064 A1 | 6/2016 |
| EP | 3158975 A1 | 4/2017 |
| EP | 3342355 A1 | 7/2018 |
| EP | 3395296 A1 | 10/2018 |
| EP | 3406225 A1 | 11/2018 |
| EP | 3417831 A1 | 12/2018 |
| EP | 3476366 A1 | 5/2019 |
| EP | 3482718 A1 | 5/2019 |
| EP | 2637607 B1 | 10/2019 |
| EP | 3554424 A1 | 10/2019 |
| EP | 324480981 | 2/2020 |
| EP | 3639792 A1 | 4/2020 |
| EP | 3417831 B1 | 5/2020 |
| EP | 3649963 A2 | 5/2020 |
| EP | 2072027 B1 | 6/2020 |
| EP | 3441045 B1 | 7/2020 |
| EP | 3672528 A1 | 7/2020 |
| EP | 3554423 B1 | 8/2020 |
| EP | 3107498 B1 | 9/2020 |
| EP | 3570782 B1 | 9/2020 |
| EP | 3700467 A1 | 9/2020 |
| EP | 3705090 A1 | 9/2020 |
| EP | 3782585 A1 | 2/2021 |
| JP | H08131551 A | 5/1996 |
| JP | 2004154177 A | 6/2004 |
| JP | 2008018139 A | 1/2008 |
| JP | 2011506017 A | 3/2011 |
| JP | 2012531270 A | 12/2012 |
| JP | 2020515375 A | 5/2020 |
| JP | 2020517379 A | 6/2020 |
| JP | 2020520729 A | 7/2020 |
| JP | 6735294 B2 | 8/2020 |
| KR | 2020032237 A | 3/2020 |
| KR | 2020033349 A | 3/2020 |
| KR | 2020033350 A | 3/2020 |
| TW | 202027694 A | 8/2020 |
| WO | WO2007/007873 A1 | 1/2007 |
| WO | WO2007/081820 A1 | 7/2007 |
| WO | WO2009/079475 A2 | 6/2009 |
| WO | WO-2010141847 A1 * | 12/2010 ........... A61F 2/2418 |
| WO | WO2011/025945 A1 | 3/2011 |
| WO | WO2012/087842 A1 | 6/2012 |

(56) References Cited

FOREIGN PATENT DOCUMENTS

| | | |
|---|---|---|
| WO | WO2012/145545 A1 | 10/2012 |
| WO | WO2013/059747 A1 | 4/2013 |
| WO | WO2013/190910 A1 | 12/2013 |
| WO | WO2015/127264 A1 | 8/2015 |
| WO | WO2015/173609 A1 | 11/2015 |
| WO | WO2015/195823 A1 | 12/2015 |
| WO | WO2016/052145 A1 | 4/2016 |
| WO | WO2016/117169 A1 | 7/2016 |
| WO | WO2016/183485 A1 | 11/2016 |
| WO | WO2017/121193 A1 | 7/2017 |
| WO | WO2017/151566 A1 | 9/2017 |
| WO | WO2017/214098 A1 | 12/2017 |
| WO | WO-2018025260 A1 * | 2/2018 |
| WO | WO2018/039561 A1 | 3/2018 |
| WO | WO2018/039589 A1 | 3/2018 |
| WO | WO2018/112429 A1 | 6/2018 |
| WO | WO2018/119304 A1 | 6/2018 |
| WO | WO2018/178966 A1 | 10/2018 |
| WO | WO2018/178967 A1 | 10/2018 |
| WO | WO2018/187390 A1 | 10/2018 |
| WO | WO2018/192197 A1 | 10/2018 |
| WO | WO2019/010370 A1 | 1/2019 |
| WO | WO2019/036592 A1 | 2/2019 |
| WO | WO2019/062366 A1 | 4/2019 |
| WO | WO2019/081777 A1 | 5/2019 |
| WO | WO2019/086958 A1 | 5/2019 |
| WO | WO2019/102484 A1 | 5/2019 |
| WO | WO2019/116369 A1 | 6/2019 |
| WO | WO2019/118371 A1 | 6/2019 |
| WO | WO2019/135011 A1 | 7/2019 |
| WO | WO2019/135028 A1 | 7/2019 |
| WO | WO-2019144036 A1 * | 7/2019 ........... A61F 2/0077 |
| WO | WO2019/147504 A1 | 8/2019 |
| WO | WO2019/147846 A2 | 8/2019 |
| WO | WO2019/154124 A1 | 8/2019 |
| WO | WO2019/164516 A1 | 8/2019 |
| WO | WO2019/195860 A2 | 10/2019 |
| WO | WO2019/209927 A1 | 10/2019 |
| WO | WO2019/222694 A1 | 11/2019 |
| WO | WO2019/241777 A1 | 12/2019 |
| WO | WO2020/051147 A1 | 3/2020 |
| WO | WO2020/051591 A1 | 3/2020 |
| WO | WO2020/072199 A1 | 4/2020 |
| WO | WO2020/072201 A1 | 4/2020 |
| WO | WO2020/073050 A1 | 4/2020 |
| WO | WO2020/123719 A1 | 6/2020 |
| WO | WO2020/157018 A1 | 8/2020 |
| WO | WO2020/163112 A1 | 8/2020 |
| WO | WO2020/180485 A1 | 9/2020 |
| WO | WO2020/236830 A1 | 11/2020 |
| WO | WO2020/247907 A1 | 12/2020 |
| WO | WO2021/021482 A1 | 2/2021 |
| WO | WO2021/028867 A1 | 2/2021 |
| WO | WO2021/034497 A1 | 2/2021 |
| WO | WO2021/086850 A1 | 5/2021 |
| WO | WO2021/087400 A1 | 5/2021 |
| WO | WO2021/091754 A1 | 5/2021 |
| WO | WO2021/113143 A1 | 6/2021 |
| WO | WO2021/178560 A1 | 9/2021 |
| WO | WO2021/183610 A1 | 9/2021 |
| WO | WO2021/207545 A1 | 10/2021 |
| WO | WO2021/257278 A1 | 12/2021 |
| WO | WO2021/257722 A1 | 12/2021 |
| WO | WO2022/010974 A1 | 1/2022 |
| WO | WO2022/046678 A1 | 3/2022 |
| WO | WO2022/047095 A1 | 3/2022 |
| WO | WO2022/047160 A1 | 3/2022 |
| WO | WO2022/047274 A1 | 3/2022 |
| WO | WO2022/047393 A1 | 3/2022 |
| WO | WO2022/047395 A1 | 3/2022 |
| WO | WO2022/066713 A1 | 3/2022 |
| WO | WO2022/066720 A1 | 3/2022 |
| WO | WO2022/121057 A1 | 6/2022 |
| WO | WO2022/174160 A1 | 8/2022 |
| WO | WO202/271851 A1 | 12/2022 |
| WO | WO2023/034936 A1 | 3/2023 |
| WO | WO2023/049625 A1 | 3/2023 |
| WO | WO2023/064910 A1 | 4/2023 |
| WO | WO2022/204138 A1 | 9/2024 |

OTHER PUBLICATIONS

Westaby et al.; Adult human valve dimensions and their surgical significance; The American Journal of Cardiology; 53(4); pp. 552-556; Feb. 1984.
Argento et al.; U.S. Appl. No. 18/185,330 entitled "Prosthetic cardiac valve devices, systems, and methods," filed Mar. 16, 2023.
Adamek-Bowers et al.; U.S. Appl. No. 18/255,763 entitled "Mitral valve implants," filed Jun. 2, 2023.
Argento et al.; U.S. Appl. No. 18/002,219 entitled "Minimal frame prosthetic cardiac valve delivery devices, systems, and methods," filed Dec. 16, 2022.
Adamek-Bowers et al.; U.S. Appl. No. 18/043,458 entitled "Prosthetic valve delivery system," filed Feb. 28, 2023.
Backus et al.; U.S. Appl. No. 18/004,609 entitled "Valve delivery system," filed Jan. 6, 2023.
Mulcahy et al.; U.S. Appl. No. 18/043,480 entitled "Prosthetic cardiac valve delivery devices, systems, and methods," filed Feb. 28, 2023.
Adamek-Bowers et al.; U.S. Appl. No. 18/043,499 entitled "Interface for prosthetic cardiac valve and delivery systems," filed Feb. 28, 2023.
Salahieh et al.; U.S. Appl. No. 18/043,519 entitled "Flared prosthetic cardiac valve delivery devices and systems," filed Feb. 28, 2023.
Scott et al.; U.S. Appl. No. 18/043,526 entitled "Access sheath for prosthetic cardiac valve delivery systems," filed Feb. 28, 2023.
Yang et al.; U.S. Appl. No. 18/043,542 entitled "Anchor for prosthetic cardiac valve devices," filed Feb. 28, 2023.
Argento et al.; U.S. Appl. No. 18/246,307 entitled "Systems, methods, and devices for expandable sensors," filed Mar. 22, 2023.
Argento et al.; U.S. Appl. No. 18/246,311 entitled "Prosthetic cardiac valve sensor devices, systems, and methods with imaging," filed Mar. 22, 2023.
Argento et al.; U.S. Appl. No. 18/494,520 entitled "Prosthetic cardiac valve devices, systems, and methods," filed Oct. 25, 2023.
Mulcahy et al.; U.S. Appl. No. 18/573,816 entitled "Prosthetic cardiac valve delivery devices, systems, and methods," filed Dec. 22, 2023.
Boyd et al., U.S. Appl. No. 18/688,735 entitled "Guide catheter for prosthetic cardiac valve delivery systems," filed Mar. 1, 2024.
Masterclass; Knit vs. Woven: Learn How to Identify the Two Fabric Types; Jun. 7, 2021; 13 pages; retrieved from the internet (https://www.masterclass.com/articles/knit-vs-woven-learn-how-to-identify-the-two-fabric-types) on Nov. 15, 2024.
Yang et al.; U.S. Appl. No. 18/700,621 entitled "Cardiac valve prosthesis delivery system and methods of use," filed Apr. 11, 2024.
Argento et al.; U.S. Appl. No. 18/639,743 entitled "Prosthetic cardiac valve devices, systems and methods," filed Apr. 18, 2024.

* cited by examiner

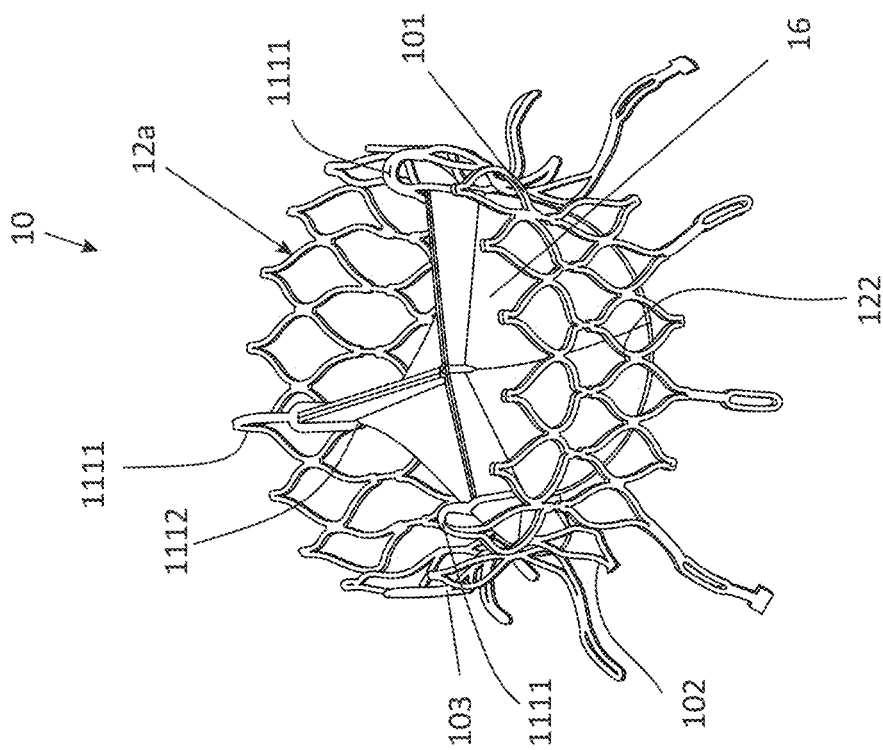
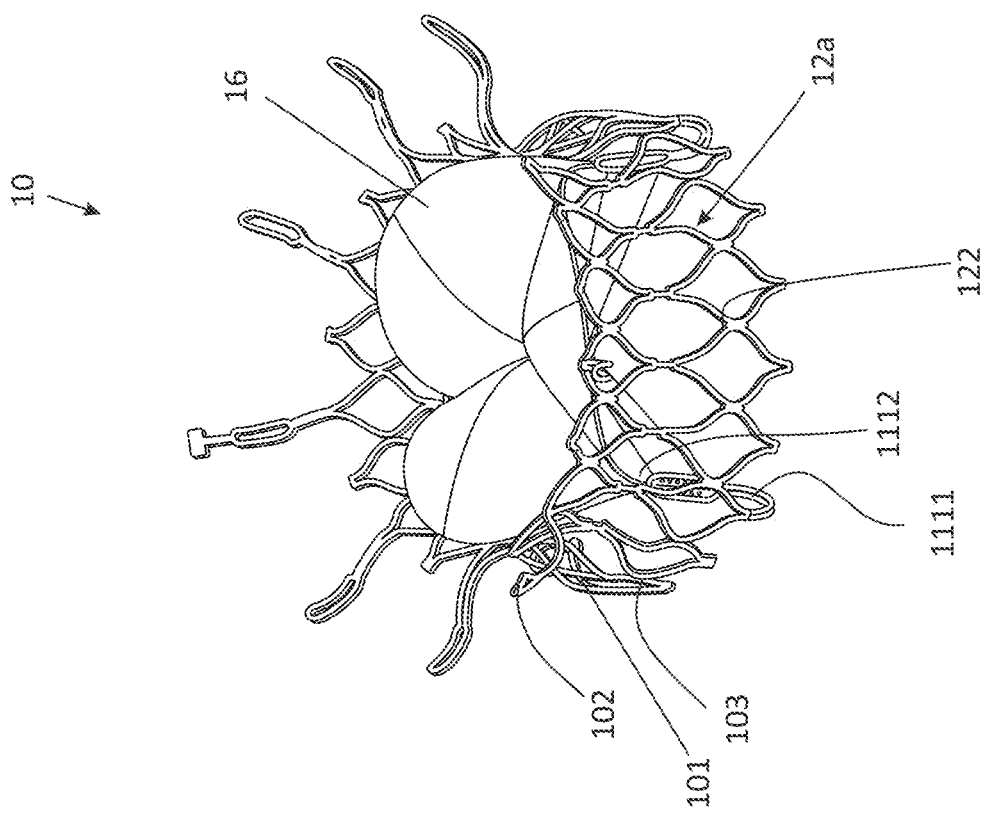
FIG. 1A
FIG. 1B

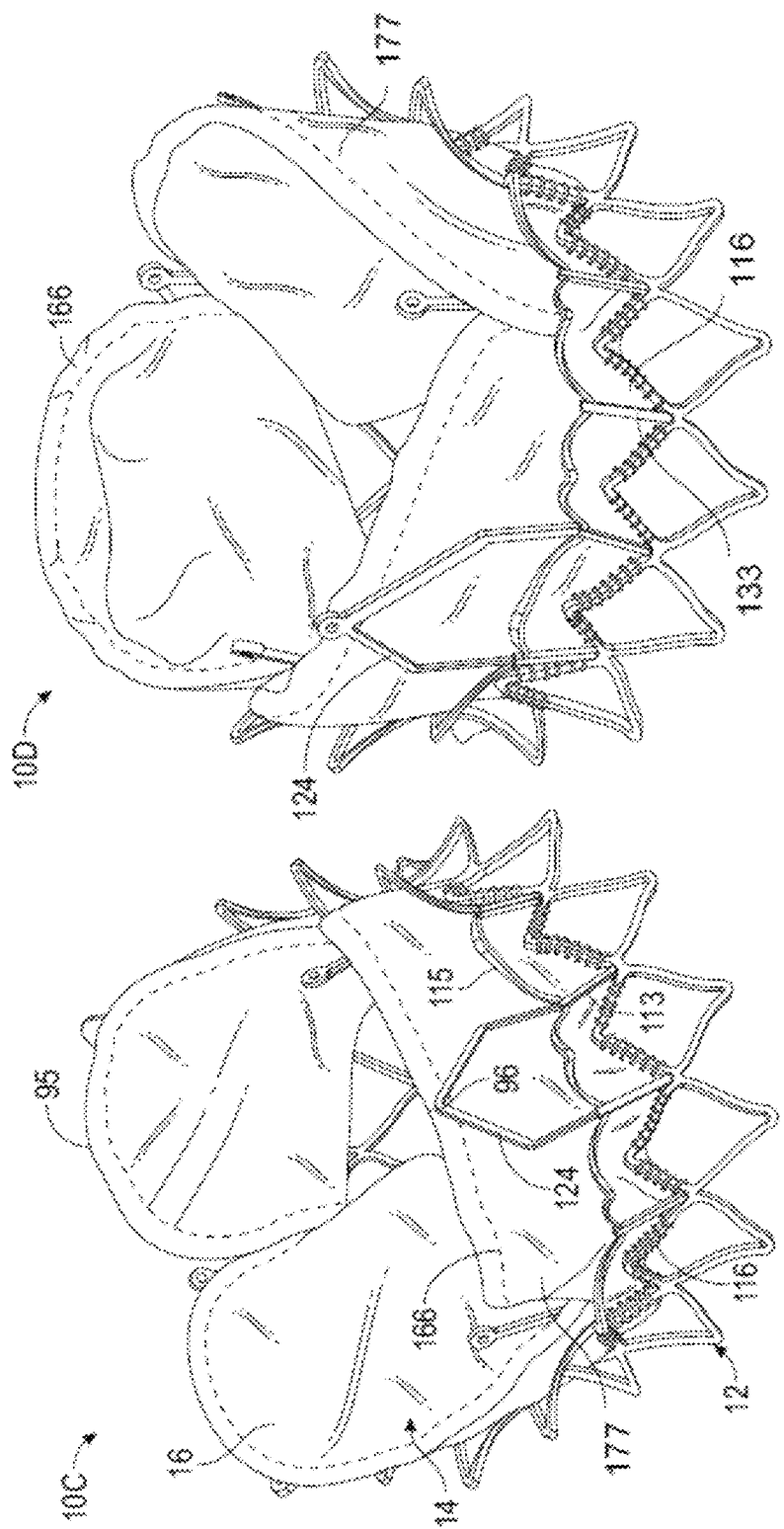

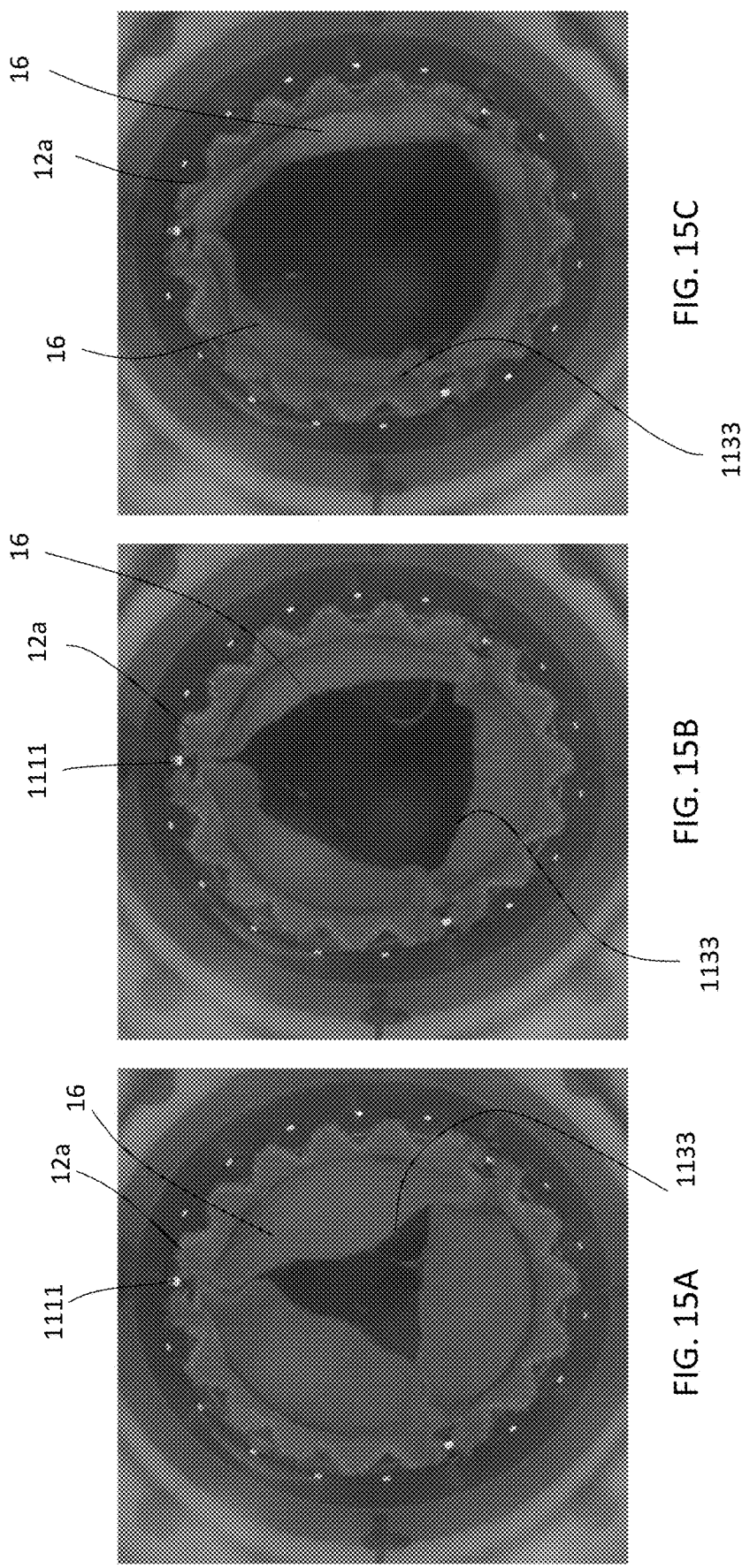

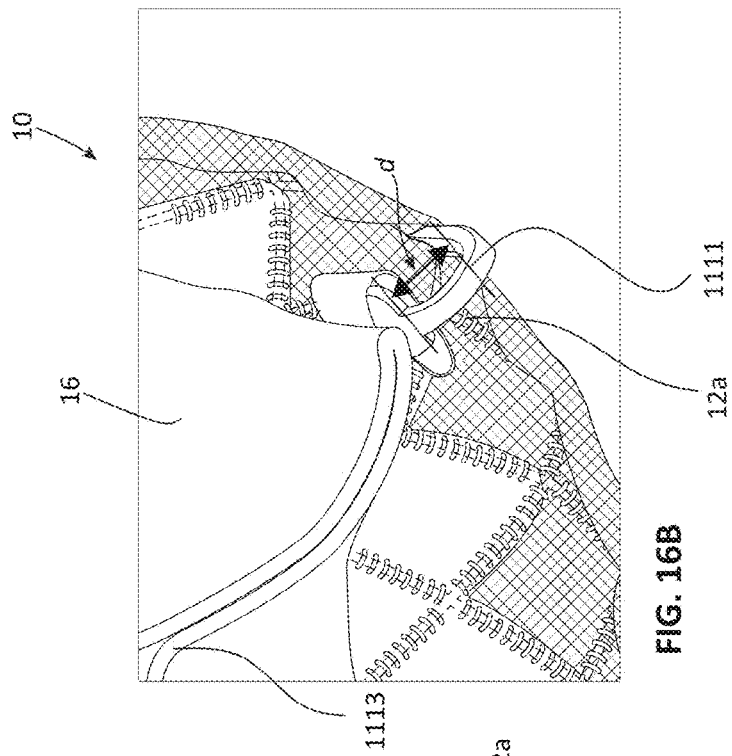
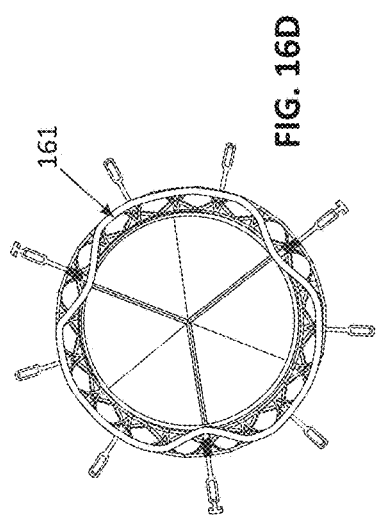
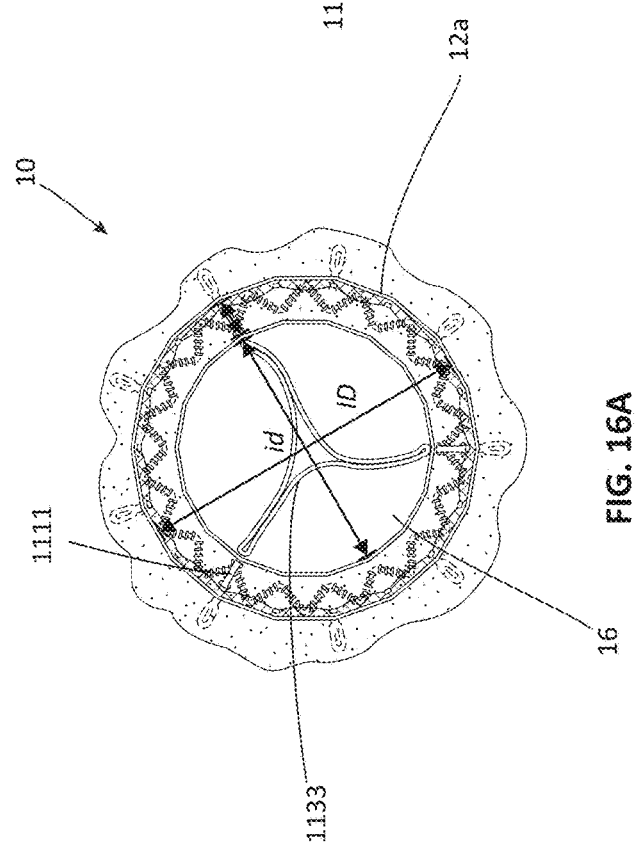
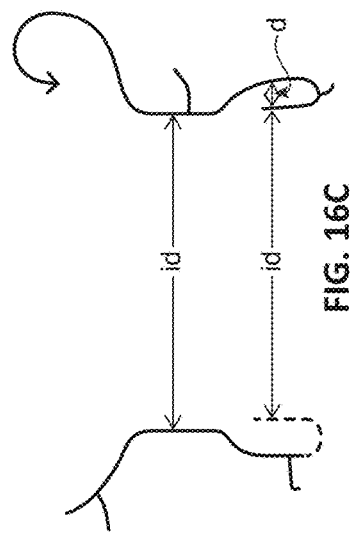

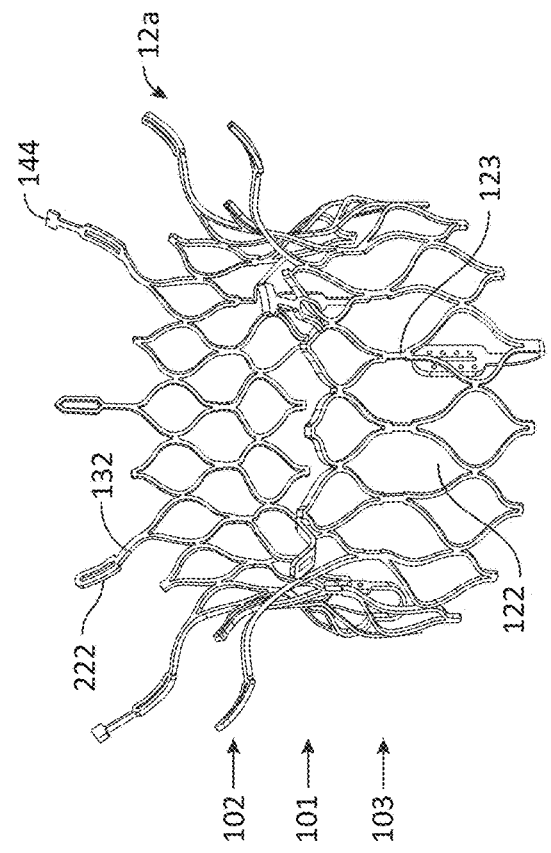
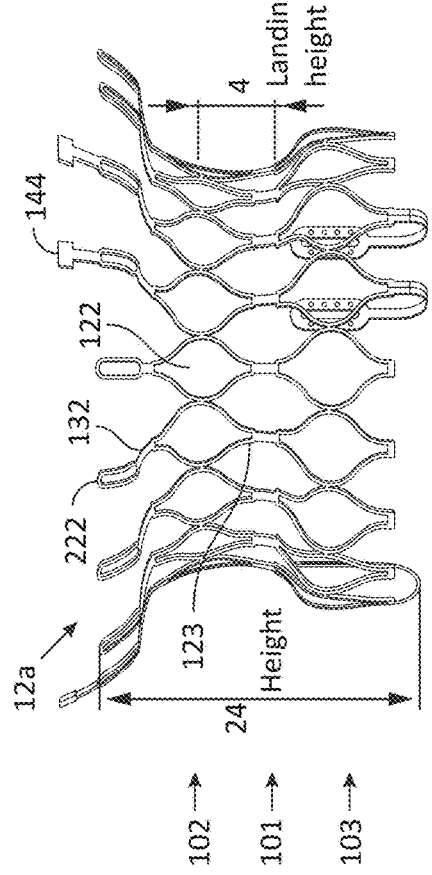
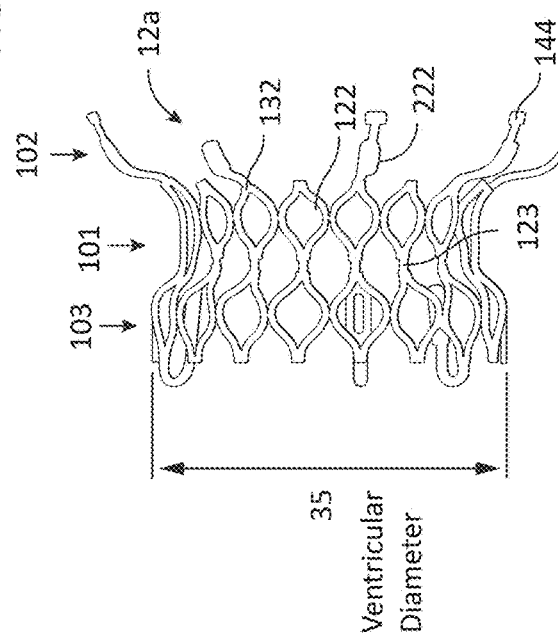
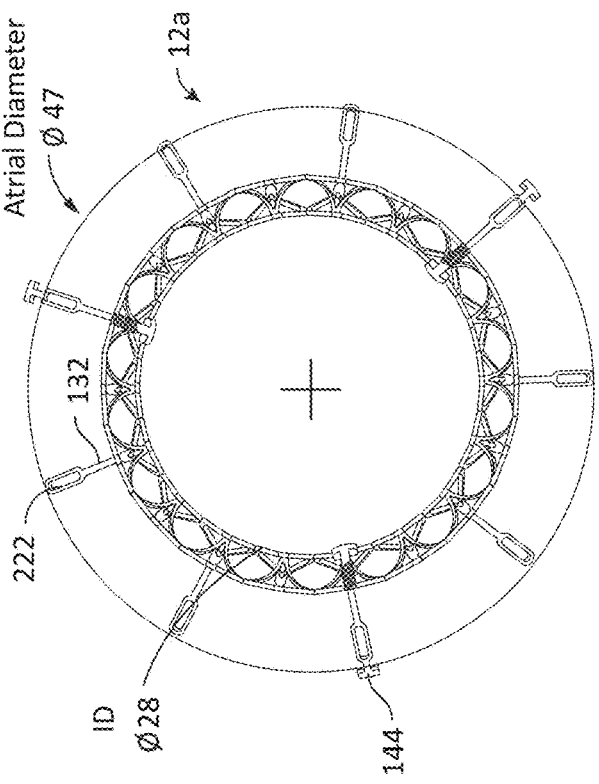
FIG. 17A
FIG. 17B
FIG. 17C
FIG. 17D

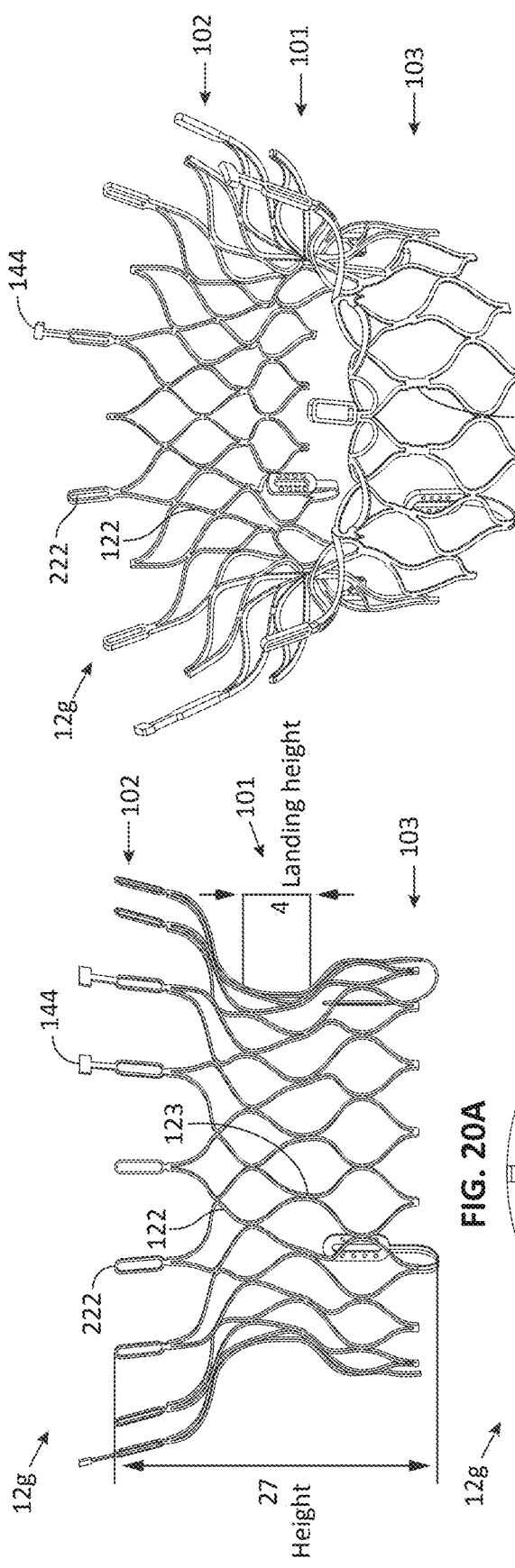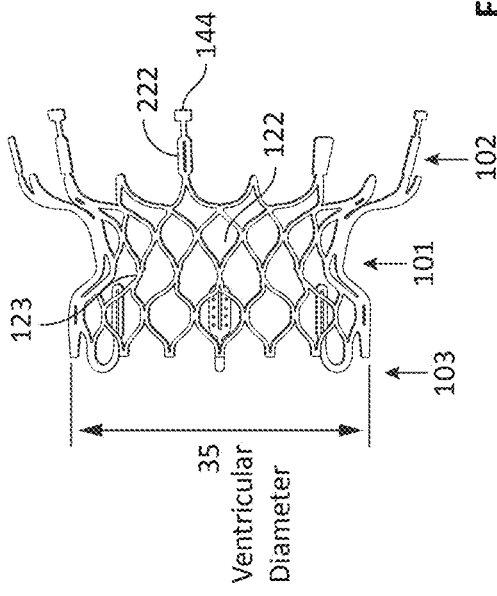
FIG. 20A
FIG. 20B
FIG. 20C
FIG. 20D

| Frame ID mm | Ventricular OD mm | Atrial OD mm | Expanded Height mm | Landing height mm | Ventricular height mm | Sheathed height approx. mm |
|---|---|---|---|---|---|---|
| 12a | 28 | 35 | 47 | 24 | 4 | 14 | <33 |
| 12e | 28 | 35 | 48 | 27 | 4 | 14 | <38 |
| 12f | 28 | 35 | 48 | 28 | 7 | 18 | <38 |
| 12g | 28 | 35 | 49 | 27 | 4 | 14 | <38 |

FIG. 21

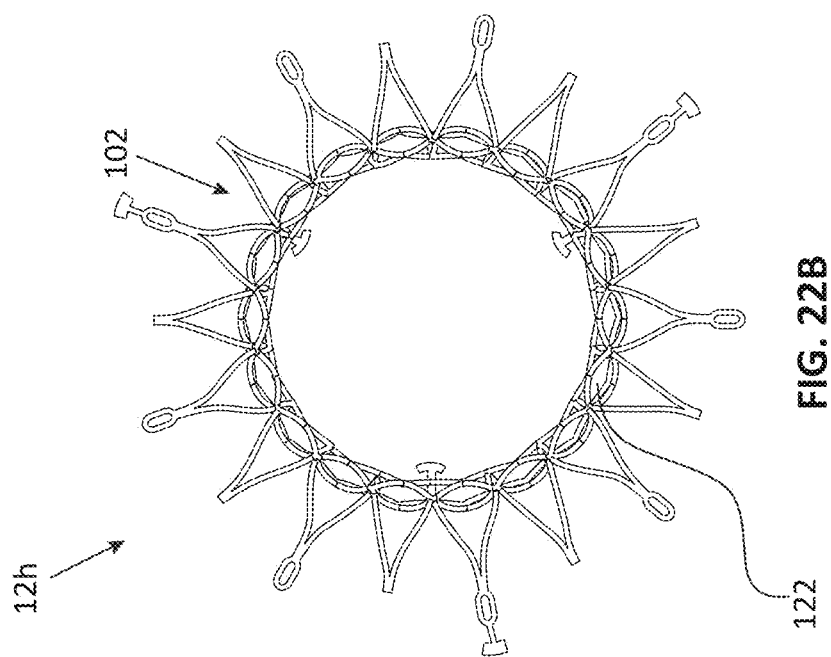
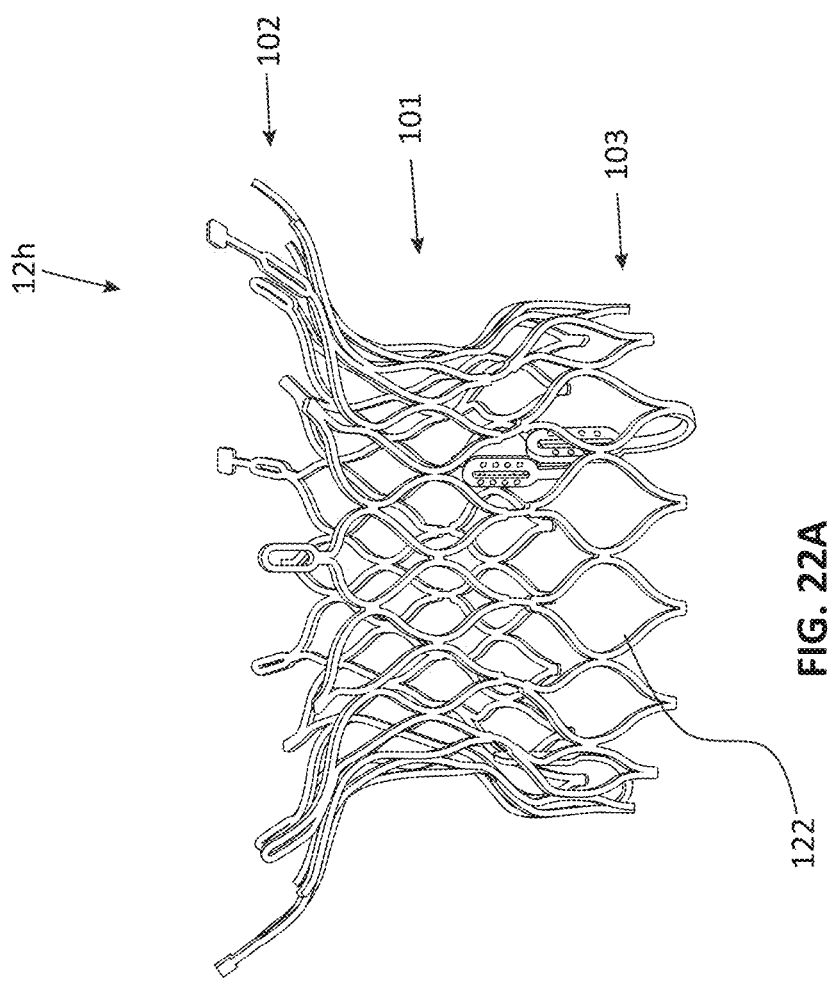

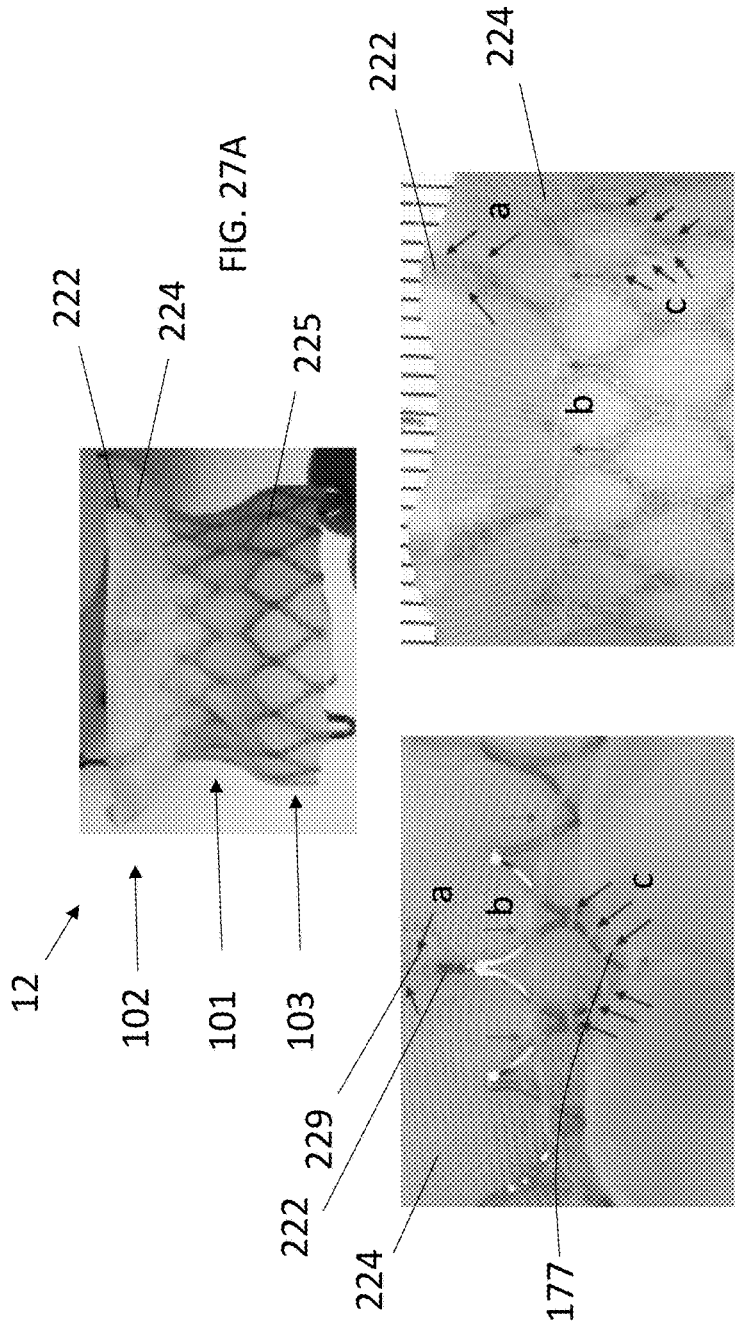
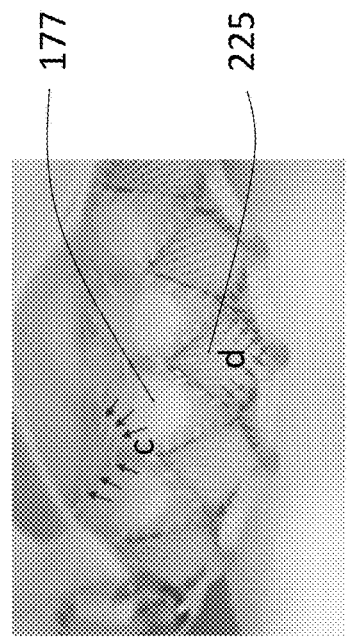
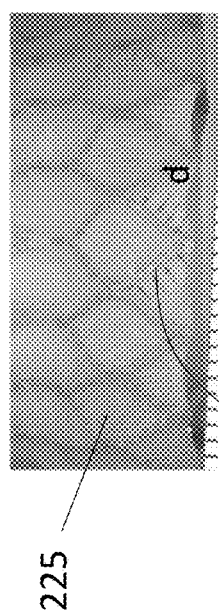
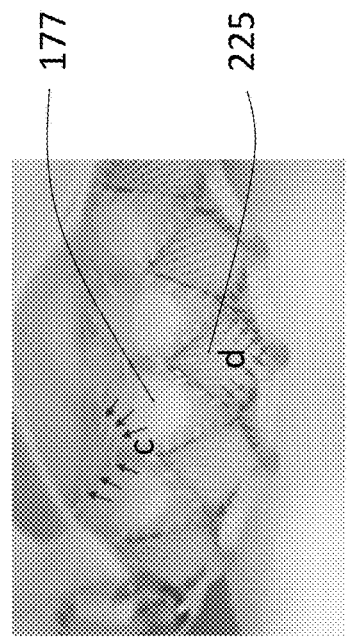

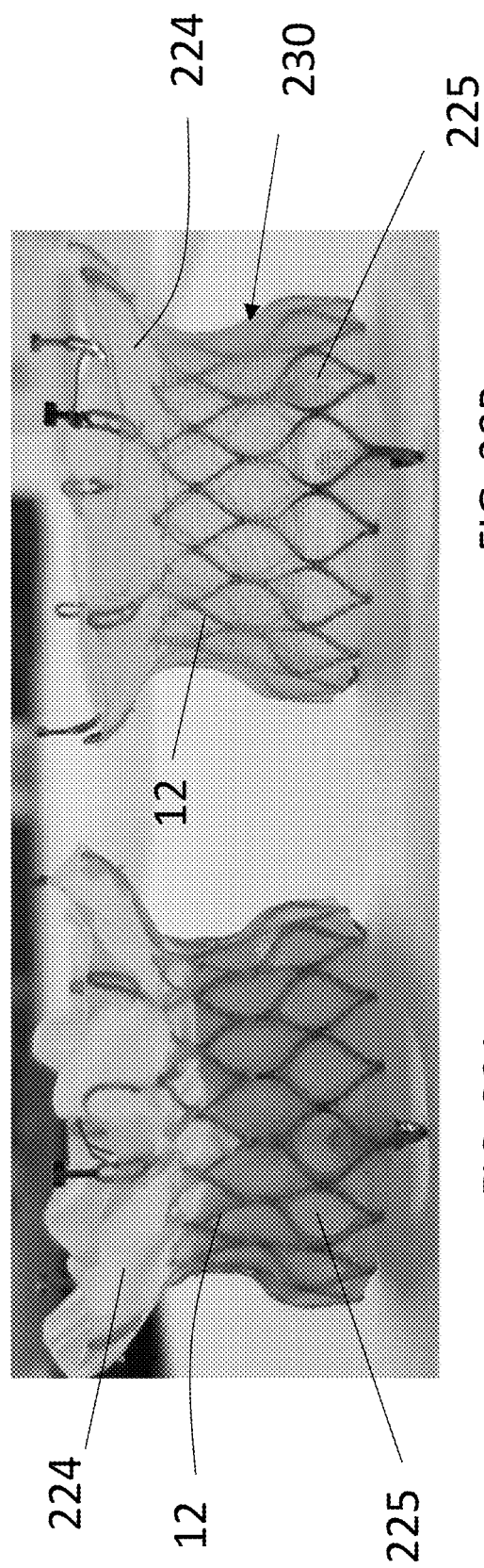

FLARED PROSTHETIC CARDIAC VALVE DELIVERY DEVICES AND SYSTEMS

CROSS-REFERENCE TO RELATED APPLICATIONS

This application claims the benefit of U.S. Provisional Appln. No. 63/121,812, filed Dec. 4, 2020, titled "MINIMAL FRAME PROSTHETIC CARDIAC VALVE DELIVERY DEVICES, SYSTEMS, AND METHODS," and to U.S. Provisional Appln. No. 63/173,281, filed Apr. 9, 2021, titled "FLARED PROSTHETIC CARDIAC VALVE DELIVERY DEVICES AND SYSTEMS," and to U.S. Provisional Appln. No. 63/274,821, filed Nov. 2, 2021, titled "FLARED PROSTHETIC CARDIAC VALVE DELIVERY DEVICES AND SYSTEMS", all of which are incorporated by reference as if fully set forth herein.

BACKGROUND

Blood flow between heart chambers is regulated by native valves—the mitral valve, the aortic valve, the pulmonary valve, and the tricuspid valve. Each of these valves is a passive one-way valve that opens and closes in response to differential pressures. Patients with valvular disease have abnormal anatomy and/or function of at least one valve. For example, a valve may suffer from insufficiency, also referred to as regurgitation, when the valve does not fully close, thereby allowing blood to flow retrograde. Valve stenosis can cause a valve to fail to open properly. Other diseases may also lead to dysfunction of the valves.

The mitral valve, for example, sits between the left atrium and the left ventricle and, when functioning properly, allows blood to flow from the left atrium to the left ventricle while preventing backflow or regurgitation in the reverse direction. Native valve leaflets of a diseased mitral valve, however, do not fully prolapse, causing the patient to experience regurgitation.

While medications may be used to treat diseased native valves, the defective valve often needs to be repaired or replaced at some point during the patient's lifetime. Existing prosthetic valves and surgical repair and/or replacement procedures may have increased risks, limited lifespans, and/or are highly invasive. Some less invasive transcatheter options are available, but most are not ideal. A major limitation of existing transcatheter mitral valve devices, for example, is that the mitral valve devices are too large in diameter to be delivered transeptally, requiring transapical access instead. Furthermore, existing mitral valve replacement devices are not optimized with respect to strength-weight ratio and often take up too much space within the valve chambers, resulting in obstruction of outflow from the ventricle into the aorta and/or thrombosis.

Thus, a new valve device that overcomes some or all of these deficiencies is desired.

SUMMARY OF THE DISCLOSURE

A device for treating a diseased native valve in a patient is provided, the device comprising a frame structure; a valve segment positioned radially within the frame structure, the valve segment comprising a plurality of leaflets, and a plurality of commissure attachment mechanisms coupling the leaflets to the frame structure, each commissure attachment mechanism extending radially inwards from an outflow end of the frame structure as to create a gap between an interior diameter of the outflow end and an outflow edge of the valve segment.

In some embodiments, an inflow edge of the valve segment is unsupported by the frame structure. In other embodiments, the inflow edge is spaced radially inwards from an inflow end of the frame structure. In some embodiments, an inflow end of the frame structure is flared radially outwards.

In one embodiment, the outflow end of the frame structure is flared radially outwards, and wherein tips of the outflow end point substantially axially.

In some embodiments, the commissure attachment mechanisms each comprise a paddle, the paddle including a slot therein through which tabs of the leaflet commissures pass.

In one example, the paddle further comprises a plurality of holes therethrough for sewing attachment of the tabs to the paddle.

In another embodiment, the commissure attachment mechanisms each include a post that attaches to the outflow end of the frame structure and curves radially inwards.

In some examples the post curves in approximately 180 degrees.

In some embodiments, the post attaches to a strut of the outflow end, and wherein a thickness of the post is greater than a thickness of the strut.

In one embodiment, the gap is between 1.5 mm and 4 mm when the leaflets are fully opened.

In some examples, the leaflets are unsupported except at the commissure attachment mechanisms.

In some embodiments, the device further comprises a spiral anchor configured to be placed around the frame structure.

In some embodiments, the frame structure comprises a plurality of struts, and wherein the struts have a narrowed portion proximate to the spiral anchor.

A device for treating a diseased native valve in a patient is also provided, the device comprising a frame structure comprising a central annular portion, an inflow portion, and an outflow portion, wherein the outflow portion is flared radially outwards relative to the central annular portion; a valve segment positioned radially within the frame structure, the valve segment comprising a plurality of leaflets, and a plurality of commissure attachment mechanisms coupling the leaflets to the outflow portion of the frame structure, each commissure attachment mechanism extending radially inwards such that an inner circumference formed by the commissure attachment mechanisms is approximately equal to an inner circumference of the central annular portion.

In some embodiments, an inflow edge of the valve segment is unsupported by the frame structure. In other embodiments, the inflow edge is spaced radially inwards from the inflow portion of the frame structure. In some examples, the inflow portion of the frame structure is flared radially outwards.

In some embodiments, tips of the outflow portion point substantially axially. In one embodiment, the commissure attachment mechanisms each comprise a paddle, the paddle including a slot therein through which tabs of the leaflet commissures pass.

In another embodiment, the paddle further comprises a plurality of holes therethrough for sewing attachment of the tabs to the paddle.

In some examples, the commissure attachment mechanisms each include a post that attaches to the outflow portion of the frame structure and curves radially inwards.

In one embodiment, the post curves in approximately 180 degrees. In other examples, the post attaches to a strut of the outflow portion, and wherein a thickness of the post is greater than a thickness of the strut.

In one embodiment, a gap between an outflow edge of the valve segment and an inner perimeter (e.g., diameter) of the outflow portion of the frame structure is between 1.5 mm and 4 mm when the leaflets are fully opened.

In some examples, the leaflets are unsupported except at the commissure attachment mechanisms.

In one embodiment, the device further comprises a spiral anchor configured to be placed around the frame structure at the central annular portion.

In some examples, the frame structure comprises a plurality of struts, and wherein the struts have a narrowed portion within the central annular portion.

A device for treating a diseased native valve in a patient is provided, the device comprising a frame structure comprising an annular central portion, a flared inflow portion, and a flared outflow portion, a valve segment positioned radially within the frame structure, the valve segment comprising a plurality of leaflets, and an internal skirt attached to the frame structure, the internal skirt comprising a plurality of convex segments configured to at least partially conform to inflow edges of the leaflets.

In some embodiments, the convex segments have a greater radius of curvature than the inflow edges of the leaflets.

In one example, an outflow edge of the internal skirt comprises a zig-zag pattern configured to match a cell pattern of the frame structure. In other examples, an outflow edge of the internal skirt is attached to the frame proximate to the annular central portion. In another embodiment, an outflow edge of the internal skirt does not extend to an outflow end of the frame structure.

In some examples, the inflow edges of the leaflets are unsupported by the frame structure. In another embodiment, the inflow edges of the leaflets are spaced radially inwards from an inflow end of the frame structure.

In some embodiments, the device further comprises a spiral anchor configured to be placed around the frame structure.

A device for treating a diseased native valve in a patient is provided, the device comprising a frame structure comprising an annular central portion, a flared inflow portion, and a flared outflow portion; a valve segment positioned radially within the frame structure, the valve segment comprising a plurality of leaflets, and an external skirt attached to the frame structure, the external skirt comprising a unitary structure covering the flared inflow portion and the flared outflow portion.

In some examples, the external skirt comprises a tube knit fabric. In another embodiment, the external skirt comprises a coating thereon.

In some embodiments, the device further comprises a spiral anchor configured to be placed around the frame structure.

In one embodiment, the external skirt is wrapped over an outflow edge of the frame structure.

In another embodiment, an additional skirt layered with the external skirt. In some examples, the additional skirt is positioned along the flared outflow portion. In one embodiment, the additional skirt is positioned along a central annular portion of the frame structure.

A device for treating a diseased native valve in a patient is provided, the device comprising a frame structure comprising a flared inflow portion comprising first and second rows of cells; an annular central portion comprising a third row of cells, and a flared outflow portion comprising a fourth row of cells, and a valve segment positioned radially within the frame structure, the valve segment comprising a plurality of leaflets.

In some embodiments, the inflow portion is flared further radially outwards than the outflow portion.

In other embodiments, the inflow portion is curved so as to point radially inwards.

In one embodiment, the device further comprises a plurality of non-foreshortening elements extending from the inflow portion.

In some examples, tips of the outflow portion point substantially axially.

In one embodiment, the third row of cells comprises a plurality of narrowed axially extending struts therein.

In other embodiments, tips of the flared outflow portion point substantially axially.

In some examples, the cells are substantially diamond-shaped.

In another embodiment, the device comprises a spiral anchor configured to be placed around the frame structure at the central annular portion.

In another example, the device includes a plurality of commissure attachment mechanisms coupling the leaflets to the frame structure, each commissure attachment mechanism extending radially inwards from an outflow end of the frame structure as to create a gap between an interior diameter of the outflow end and an outflow edge of the valve segment.

A method for treating a diseased native valve in a patient is provided, comprising: providing a device including a frame structure, a valve segment positioned radially within the frame structure, the valve segment comprising a plurality of leaflets, and a plurality of commissure attachment mechanisms coupling the leaflets to the frame structure; advancing the device to the diseased native valve in the patient; deploying the device within the diseased native valve to secure the device to the diseased native valve; and allowing an outflow edge of the plurality of leaflets to open to a radius that is greater than a radius formed by the plurality of commissure attachment mechanisms.

In some embodiments, the outflow edge of the plurality of leaflets is allowed to open to a radius that is less than an inner perimeter of the frame structure.

In other embodiments, the opening of the plurality of leaflets is configured to maintain a cylindrical flow path.

A method for treating a diseased native valve in a patient is provided, comprising: providing a device including a frame structure, a valve segment positioned radially within the frame structure, the valve segment comprising a plurality of leaflets, and a plurality of commissure attachment mechanisms coupling the leaflets to the frame structure, wherein the plurality of commissure attachment mechanisms extend radially inwards such that an inner circumference formed by the commissure attachment mechanisms is less than an inner circumference formed by the frame structure; advancing the device to the diseased native valve in the patient; deploying the device within the diseased native valve to secure the device to the diseased native valve; and allowing an outflow edge of the plurality of leaflets to open to a radius that is greater than a radius formed by the plurality of commissure attachment mechanisms.

In some embodiments, the outflow edge of the plurality of leaflets is allowed to open to a radius that is less than an inner perimeter of the frame structure.

In other embodiments, the opening of the plurality of leaflets is configured to maintain a cylindrical flow path.

BRIEF DESCRIPTION OF THE DRAWINGS

The novel features of the present disclosure are set forth with particularity in the appended claims. A better understanding of the features and advantages of the present disclosure will be obtained by reference to the following detailed description that sets forth illustrative embodiments, in which the principles of the present disclosure are utilized, and the accompanying drawings of which:

FIGS. 1A-1B show an implantable valve prosthesis, in accordance with embodiments.

FIGS. 6-7 show a frame with a valve segment attached to one or more struts of the frame structure.

FIGS. 15A-15C illustrate the leaflets opening.

FIGS. 16A-16D illustrate various views of a frame structure with leaflets including dimensions.

FIGS. 17A-17D illustrate one example of a frame structure.

FIGS. 20A-20D illustrate yet another example of a frame structure.

FIG. 21 is a table showing exemplary dimensions for various frame structures.

FIGS. 22A-22B illustrate one example of a frame structure.

FIGS. 27A-27F illustrate attachment or sewing points of a skirt to the frame.

FIGS. 30A-30B illustrate a frame with an internal skirt or an external skirt.

DETAILED DESCRIPTION

Figure 2:
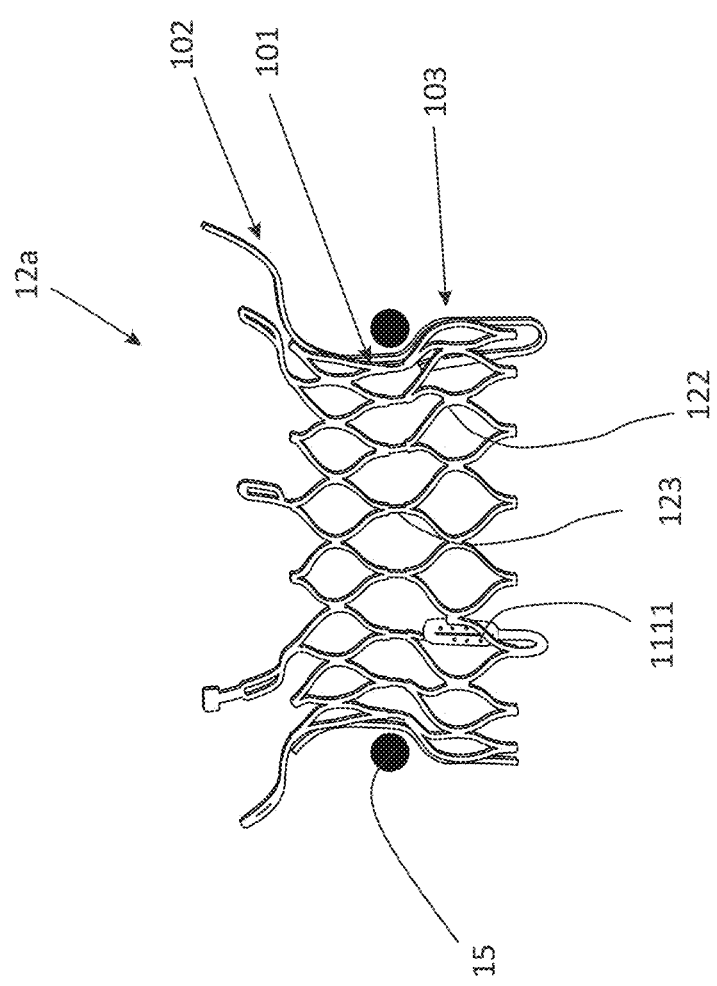
FIG. 2 shows a frame structure of a valve prosthesis in a partial hourglass shape.

Described herein are systems, devices, and methods for treatment or replacement of a diseased native valve of the heart, such as the mitral valve.

In general, described herein is a replacement prosthesis that can include a valve frame and a spiral anchor therearound.

FIGS. 1A-1B show a valve prosthesis 10 having a valve frame 12a and a plurality of leaflets 16 therein. The valve frame 12a can include interior commissure attachment mechanisms 1111 for attachment of the commissures 1112 of leaflets 16 to the frame structure 12. The valve frame 12a can be deployed from a collapsed (delivery) configuration to an expanded configuration during a method of replacing or repairing a native valve, such as a mitral valve. As shown in FIGS. 1A-1B, the valve frame 12a can include a plurality of rows (e.g., 3-7 rows) of substantially diamond-shaped cells 122. The valve frame 12a can foreshorten during delivery (i.e., as the valve frame 12 transitions from the collapsed configuration to the expanded configuration) due to the cell structure. In some embodiments, the valve frame 12a can be configured to self-expand from the collapsed configuration to the expanded configuration (e.g., can be made of nitinol). The valve frame 12a can provide circumferential strength and/or longitudinal strength to valve prosthesis 10.

The valve prosthesis 10 can be deployed in an expanded configuration according to the methods described herein. For example, valve prosthesis 10 can be deployed into an expanded configuration in a method of replacing or repairing a native anatomical structure. In the expanded configuration, valve prosthesis 10 can be positioned and/or anchored at a target region of a subject (e.g., an organ or tissue of an animal such as a dog, cat, horse, or human). For example, valve prosthesis 10 can be positioned in the expanded configuration in the orifice of a heart valve, such as the mitral valve or tricuspid valve (e.g., to function as a temporary or permanent replacement for an existing mitral valve or tricuspid valve of the heart).

One or more portions of the valve frame 12a can be shaped or configured to aid in securing the valve frame 12 at a location (e.g., in the orifice of a native heart valve). For example, the valve frame 12a can include an atrial flared portion 102 and a ventricular flared portion 103 configured to help secure the frame in the anatomy. The atrial and ventricular flared portions 102, 103 can extend radially outwards from a central annular portion 101. The atrial flared portion 102 can, for example, extend into the atrium of the heart from the central annular portion 101 when the valve prosthesis is deployed in the native mitral valve. The ventricular flared portion 103, in turn, can extend into the ventricle of the heart from the central annular portion 101 when the valve prosthesis is deployed in the native mitral valve. The atrial and ventricular flared portions 102, 103 can, for example, be configured to be positioned on either side of an external flat spiral anchor (e.g., that is wrapped around the chordae) to anchor the valve frame 12 in the anatomy. Alternatively or additionally, the atrial and ventricular flared portions 102, 103 can be configured to engage with tissue to prevent the valve prosthesis from slipping through the native valve orifice.

Referring to FIG. 2, the frame structure 12a of the valve prosthesis 10 can be in a partial hourglass shape such that the flared ventricular portion 103 initially flares radially outwards, but then curves to point substantially axially (i.e., in the ventricular direction). This half-hourglass or cup shape of the ventricular portion 103 can advantageously help provide space for the chordae therearound.

As shown in FIG. 2, the spacing between the atrial and ventricular portions 102, 103 (i.e., along the smaller diameter central annular portion 101) can enable the anchor 15 to lodge therebetween to better anchor the prosthesis in place in the native valve. Further, as shown in FIG. 2, the annular central portion 101 can include axially extending struts 123 that are narrower than the struts that form the rest of the diamond-shaped cells 122. The narrowed axially extending struts 123 can create an area of flexibility within the annular central portion 101, encouraging the anchor 15 to rest against that portion of the frame structure 12a.

Further, as shown in FIGS. 1A-1B and 2, the atrial flared portion 102 can extend further radially outwards than the ventricular flared portion 103. Having a larger atrial flared portion can help prevent para-valvular leakage (PVL).

Figure 3:
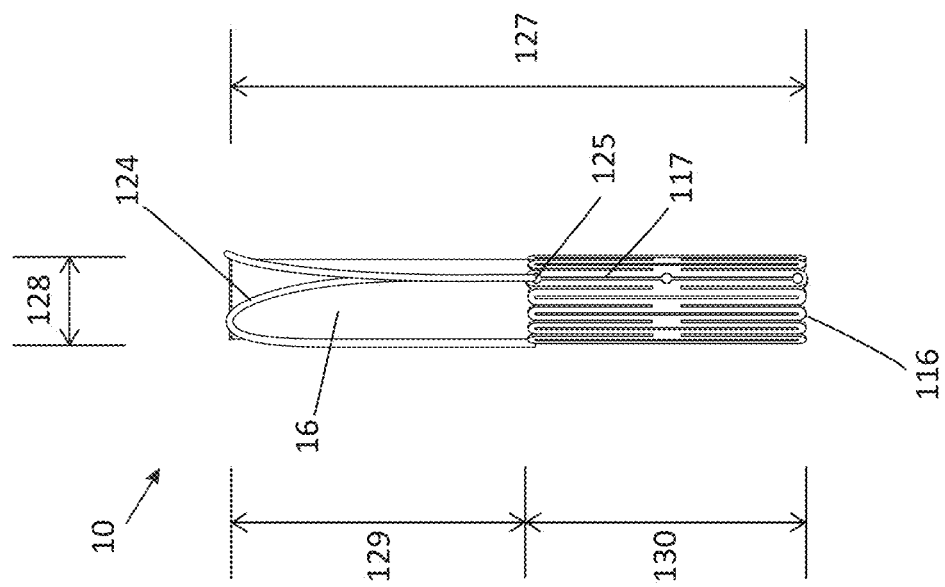
FIG. 3 shows a valve prosthesis in an unexpanded (or collapsed or crimped) configuration.

FIG. 3 shows a valve prosthesis in an unexpanded (or collapsed or crimped) configuration. In some cases, the valve prosthesis 10 can be delivered to a target region (e.g., a region of a heart comprising a native valve) in the unexpanded configuration. In some cases, the valve prosthesis 10 in the unexpanded configuration can allow the valve prosthesis 10 to be delivered via minimally invasive means (e.g., via a delivery device, as described herein).

In some embodiments, the longitudinal length 127 of the collapsed valve frame 12a can be minimized, which can be advantageous for delivery of the valve frame 12a. For example, minimizing the overall longitudinal length of the collapsed valve frame 12a can allow improved maneuverability within a delivery device while maintaining structural strength of the device. In some embodiments, minimizing the overall longitudinal length of the collapsed valve frame 12a can allow insertion of valve frame 12a through an access path that would be challenging for a longer device to traverse (e.g., an access path comprising tortuous passages or passages with sharp turns). In some embodiments, the valve frame 12a in the unexpanded configuration can have an overall longitudinal length of from 1 mm to 50 mm, from 1 mm to 45 mm, from 1 mm to 40 mm, from 1 mm to 35 mm, from 1 mm to 30 mm, from 1 mm to 25 mm, from 1 mm to 20 mm, from 1 mm to 10 mm, from 10 mm to 45 mm, from 20 mm to 45 mm, from 20 mm to 30 mm, from 25 mm to 35 mm, or from 27.5 mm to 32.5 mm. In some embodiments, the valve frame 12a in the expanded configuration can have an overall longitudinal length of from 1 mm to 45 mm, from 10 mm to 45 mm, from 15 mm to 45 mm, from 15 mm to 35 mm, from 16 mm to 34 mm, from 17 mm to 33 mm, from 18 mm to 32 mm, from 19 mm to 31 mm, from 20 mm to 30 mm, from 25 mm to 35 mm, or from 27.5 mm to 32.5 mm. In some embodiments, the valve frame 12a can foreshorten as it expands such that the length in the expanded configuration is less than the length in the collapsed configuration.

In some embodiments, the valve frame 12a and/or overall prosthesis can have specific features designed to increase stiffness, improve control over valve deployment, promote uniform radial expansion of the central annular portion, ensure anchoring within the annulus, and/or decrease PVL.

Further, the diameter 128 of the collapsed valve prosthesis 10 can be minimized, which can likewise be advantageous for delivery of the valve prosthesis 10. For example, a collapsed valve prosthesis 10 with a smaller diameter 128 can fit inside of a delivery device with a smaller diameter, allowing for less invasive delivery and for improved maneuvering capability inside of a subject's body. Reducing the diameter 128 of the collapsed valve prosthesis 10 (e.g., for use in treatment or replacement of a mitral valve, a tricuspid valve, an aortic valve, or a pulmonic valve) can further allow for easier delivery of the valve prosthesis 10 to a target region of a subject, faster recovery of a subject receiving valve prosthesis 10, and/or improved clinical outcomes for a subject receiving valve prosthesis 10 (e.g., improved subject survival, improved ejection fraction, improved cardiac output, decreased valvular regurgitation, and/or decreased edema). In some cases, reducing the diameter 128 of the collapsed valve prosthesis 10 can make transseptal access and delivery possible in addition to transapical access. In some cases, the diameter 128 of the collapsed valve prosthesis 10 or portion thereof (e.g., frame structure 12) can be from 0.01 mm to 20 mm, 0.01 mm to 15 mm, 0.01 mm to 10 mm, from 0.01 mm to 9 mm, from 0.01 mm to 8 mm, from 0.01 mm to 7 mm, from 0.01 mm to 6 mm, from 0.01 mm to 5 mm, from 0.01 mm to 4 mm, from 0.01 mm to 3 mm, from 0.01 mm to 2 mm, from 0.01 mm to 1 mm, from 1 mm to 15 mm, from 2 mm to 14 mm, from 3 mm to 13 mm, from 4 mm to 12 mm, from 5 mm to 10 mm, from 6 mm to 10 mm, from 7 mm to 10 mm, from 8 mm to 10 mm, from 9 mm to 10 mm, from 10 mm to 15 mm, no more than 20 mm, no more than 15 mm, no more than 10 mm, no more than 9 mm, no more than 8 mm, no more than 7 mm, no more than 6 mm, or no more than 5 mm.

In some cases, the valve prosthesis 10 or a portion thereof can be sized or shaped to be positioned at a certain location or target region. For example, the frame structure 12 can be sized to be positioned in a valve, such as the mitral valve (e.g., by designing a dimension of frame structure to fit a valve, such as the mitral valve, when in an expanded configuration).

Figure 4:
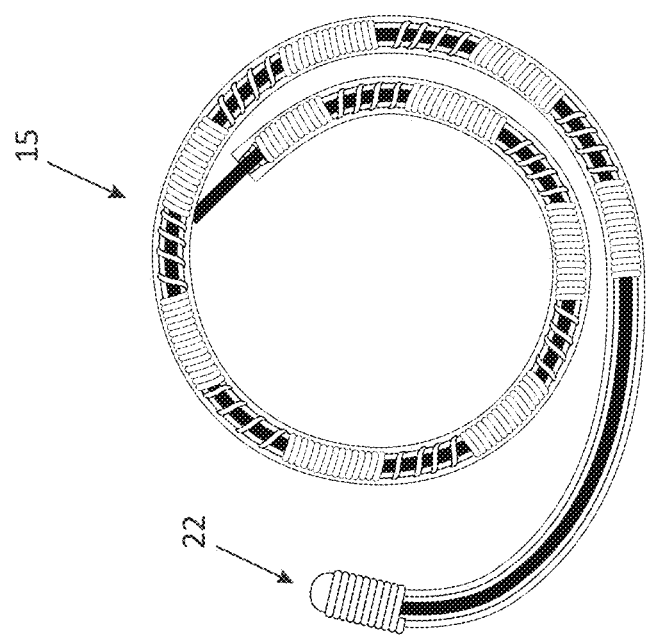
FIG. 4 shows a representative example an anchor for a valve prosthesis.

FIG. 4 shows a representative example of the an anchor 15 configured to position or anchor a valve prosthesis within a certain location such as a native valve. In some embodiments, the anchor 15 may comprise a flat shape that, for example, span around the valve prosthesis 10 in the unexpanded and/or expanded configuration. The anchor 15 can have a free end 22. In some cases, the free end 22 of anchor 15 can be useful during deployment of the anchor 15 in a native heart valve (e.g., by ensnaring chordae or other structures when the prosthesis 10, anchor 15, and/or delivery device are rotated around longitudinal axis of the valve prosthesis 10). The anchor 15 may be directly coupled to the frame structure 12a, for example at a first end (e.g., a proximal end) or a second end (e.g., a distal end) thereof. Alternatively, the anchor 15 can be physically uncoupled from the frame structure 12 while providing an anchor for the frame 12 as the frame expands within the native valve orifice (thereby sandwiching tissue between the frame 12 and the anchor 15). In some embodiments, the frame structure 12a can be at least partially held in place within the native valve via interaction with the anchor 15. For example, the expanded diameter of the frame structure 12a can be greater than or equal to the inner diameter of the spiraled anchor 15 such that the frame structure 12a expands into and engages with the anchor 15 (with native valve leaflets, chordae, or other tissue therebetween).

Figure 5:
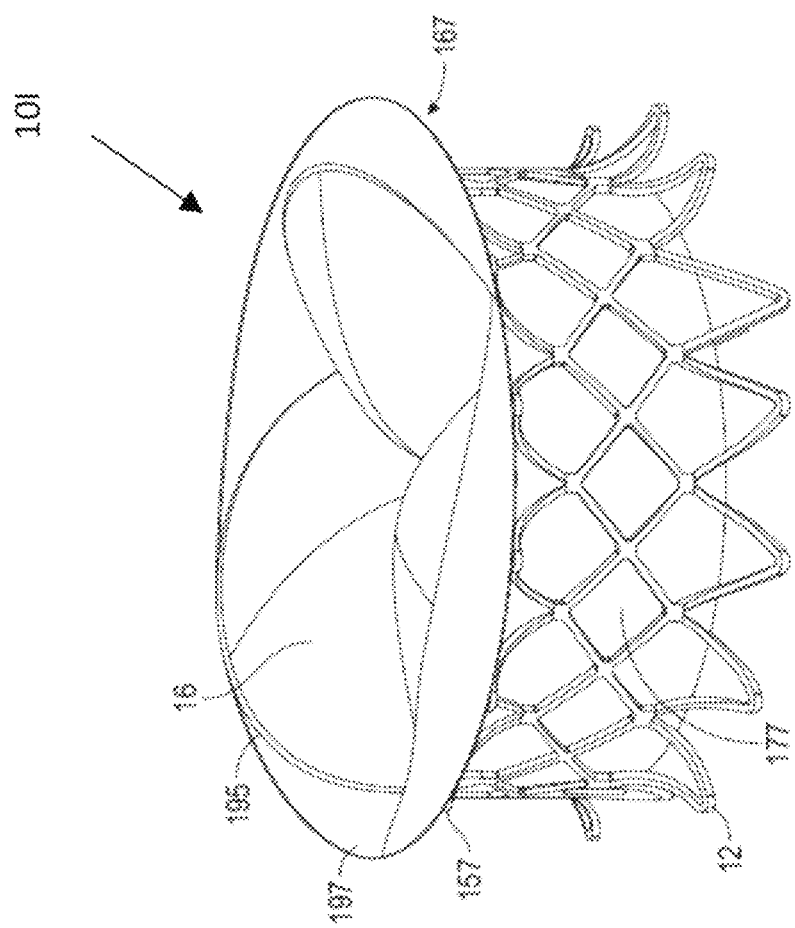
FIG. 5 is an example of a frame structure with one or more leaflets.

In some embodiments, the valve prostheses 10 described herein can include one or more flared portions to engage with the anchor 15 and/or help prevent the valve prostheses 10 from sliding through a valve orifice. For example, as shown in FIG. 5, the frame structure 12a of valve prosthesis 10I can include an atrial flared portion 157 extending radially outwards from a central annular portion 158. The atrial flared portion 157 can, for example, extend into the atrium of the heart from the central annular portion 158 when valve prosthesis 10I is deployed in a native mitral valve. Alternatively, or in combination, the atrial flared portion 157 can contact a tissue of the atrium of the heart, e.g., a mitral valve annulus when valve prosthesis 10I is deployed in a native mitral valve.

Referring to FIGS. 5-6, the valve prostheses 10 described herein may include one or more valve segments 14 disposed therein to replace the native valve leaflets. For example, the valve segment 14 can include a plurality of leaflets 16, e.g., that form a biocompatible one-way valve. Flow in one direction may cause the leaflets 16 to deflect open and flow in the opposite direction may cause the leaflets 16 to close.

Any of the valve segments 14 described herein may be formed of multi-layered materials for preferential function. Referring to FIG. 6, for example, the valve prosthesis 10C may include a valve segment 14 having a seal 177 (also called an outer leaflet, outer layer, or skirt) positioned radially between leaflets 16 (also called inner leaflets or the inner layer) and the frame structure 12. The seal 177 can be a single piece wrapped around the leaflets 16 or can be individual pieces shaped to match the leaflets 16. In some cases, the seal 177 and/or leaflets 16 can be formed from or coated with a material to confer an advantage upon the valve segment 14. For example, a layer or surface of a valve segment 14 can be formed from or coated with a biocompatible material. In some cases, a layer or surface of a valve segment 14 can be formed from or coated with an anti-thrombotic material. In some cases, a valve segment 14 (or portion thereof, such as a leaflet 16 of the valve segment) comprises a synthetic material. In some cases, a valve segment 14 (or portion thereof, such as a leaflet) comprises a biological tissue. In many cases, a valve segment 14 (or portion thereof, such as a leaflet) comprises pericardial tissue. In some embodiments, a valve segment 14 (or portion thereof, such as a leaflet 16 of the valve segment 14) comprises a decellularized biological tissue. For example, a valve segment 14 (or portion thereof, such as a leaflet 16 of the valve segment) can include decellularized pericardium.

The valve segment 14 may be attached to a frame structure 12, which can in turn be attached to the anchor 15. The frame structure 12 may be connected to the anchor 15 before or after the frame structure 12 has been deployed adjacent a native valve. The frame structure 12 may be attached to the valve segment 12, for example, via attachment of the frame structure 12 to the seal 177, which can in turn be attached to the leaflets 16.

In some embodiments, two or more portions of a valve segment 14 (e.g., two or more leaflets 16, and/or seal 177) can comprise a single piece of material (e.g., a single piece of biological or synthetic tissue formed into the shape of a functional valve). In some cases, two or more portions of a valve segment (e.g., two or more of a first and second leaflet 16, and/or the seal 177) can be joined together. In some embodiments, two or more portions of a valve segment (e.g., two or more of a first and second leaflet 16, and/or the seal 177) can be joined together by suturing the two or more portions together (e.g., at convex segment 166 shown in FIG. 6). In some cases, 1, 2, 3, 4, 5, or more than 5 leaflets 16 can be coupled to a single seal 177.

In many cases, convex segment 166 is disposed at an inflow end of valve prosthesis 10 (i.e., closest to the source of flow through the device, e.g., caused by a contracting heart chamber) when deployed. In some cases, coupling two or more portions of a valve segment 14 at the inflow end of valve prosthesis 10 (or portion thereof) allows the valve segment 14 to fold or collapse (e.g., radially away from a longitudinal axis of valve prosthesis device 10) during contraction of a heart chamber upstream of the deployed device (i.e., during diastole). Further, in some cases, coupling two or more portions of a valve segment 14 at the inflow end of valve prosthesis 10 causes the valve segment 14 to expand (e.g., radially toward a longitudinal axis of valve prosthesis device 10) during refilling of a heart chamber upstream of the deployed device (i.e., during systole). This expansion of the valve segment 14 can, for example, result in billowing or parachuting of the valve segment 14 (e.g., between the seal 177 and the leaflets 16) to block the flow of blood therethrough.

As shown in FIG. 6, the valve segment 14 can be attached to one or more struts 113 of the frame structure 12. In some embodiments, a portion of a valve segment 14 (e.g., leaflets 16 or seal 177) can be sutured to the central annular portion 158 of frame structure 12 and not to the inflow portion of frame structure 12 or the outflow portion of frame structure 12 (e.g., can be unattached to the distal arches 116 and the proximal arches 115 as shown in FIG. 6).

Figures 8A, 8B:
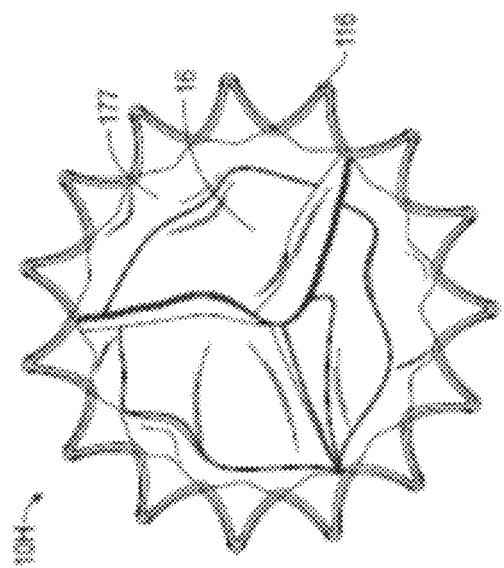
FIGS. 8A-8B show another valve prosthesis where substantially all of the inflow edge extends proximally beyond the proximal arches of the frame structure.

In some embodiments, a portion of a valve segment 14 (e.g., leaflets 16 or seal 177) can be sutured to one or more outflow portion of frame structure 12 and not to the inflow portion of frame structure 12 (e.g., can be sutured to one or more distal arches 116 but not one or more proximal arches 115 as shown in FIG. 8A).

Figure 9:
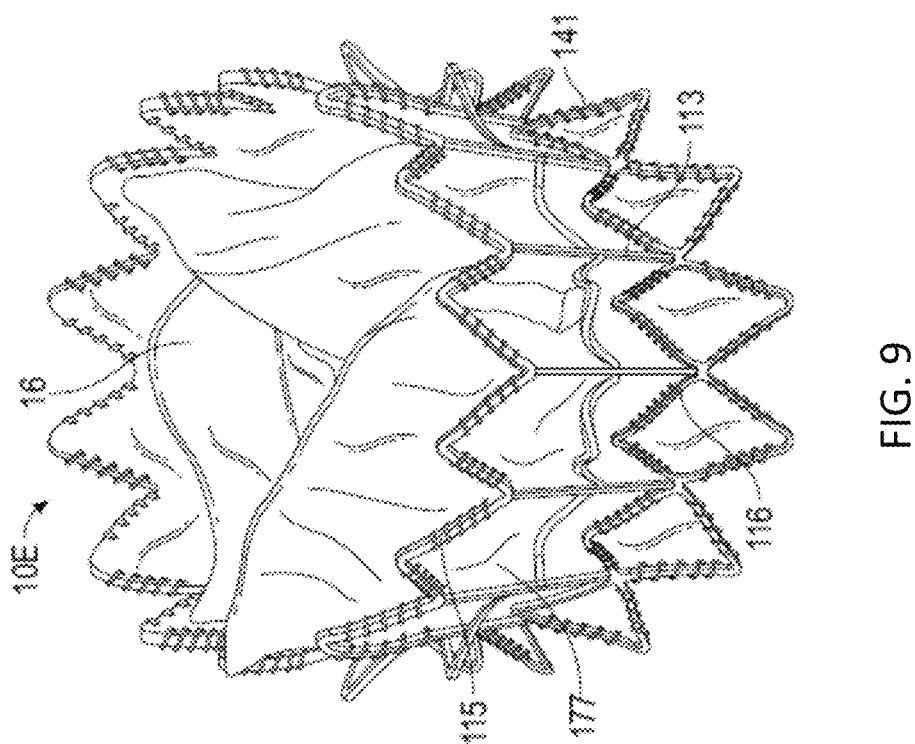
FIG. 9 shows another embodiment of a frame structure.

In some embodiments, a portion of the valve segment 14 can be sutured or otherwise attached with an outflow attachment mechanism (e.g., with inwardly extending commissure attachment mechanisms as illustrated and described further herein) and not to the inflow portion of the frame. In some embodiments, a portion of a valve segment 14 (e.g., leaflets 16 or seal 177) can be sutured to one or more outflow portion of frame structure 12 and to the inflow portion of frame structure 12 (e.g., can be sutured to one or more distal arches 116 and also to one or more proximal arches 115 as shown in valve prosthesis 10E of FIG. 9). In some embodiments, an inflow end of the valve segment 14 can be substantially unsupported by the frame 12 while the outflow end of the valve segment 14 can be fully supported by and within the valve segment 14 (as shown in FIG. 6). The valve segment 14 (or portion thereof, such as the seal 177) can be coupled to the frame 12 continuously around the inner circumference of the frame 12 (e.g., at a distal or outflow end of valve prosthesis device 10).

In some cases, the amount of attachment of a valve segment 14 (e.g., a valve leaflet 16) to the frame structure 12 can be minimized, which can advantageously enhance ease of delivery and reduce the required length of the frame, thereby reducing the chance of thrombosis and reducing the chance of blocking the outflow from the ventricle to the aorta. Minimizing the frame structure 12 can also improve the speed and cost of fabrication of the valve prosthesis device 10.

In some embodiments, a leaflet 16 that is attached to a first portion of frame structure 12 (e.g., one or more struts 113) at a distal end of frame structure 12 can be unattached at a proximal end of the frame structure 12 (e.g., a strut or portion thereof at a proximal end of frame structure 12). In some cases, valve prosthesis devices 10 in which a valve segment 14 is attached at a proximal end of frame structure 12 and is unattached at a proximal end of frame structure 12 (and/or at a proximal end of valve segment 14) may require less metal and/or fewer struts than a valve prosthesis 10 in which a valve segment 14 is attached at both a proximal end and a distal end of the frame structure 12 of the valve prosthesis device 10. In some cases, minimizing the amount of metal used in the structure of valve prosthesis 10 (e.g., by reducing the number and/or length of struts in valve prosthesis device 10) can reduce the risk of thrombus formation and can improve the ease with which the device is deployed at a target location.

Further, the valve segment 14 can be configured to be substantially unsupported at the inflow edge 95 of the valve segment 14. For example, as shown in FIG. 6, the entire inflow edge 95 of valve segment can be unsupported with the exception of minimal valve supports 124 positioned at the nadir 96 of each leaflet 16. The valve supports 124 can have a pointed proximal tip and can extend, for example, from two neighboring struts 113 of the frame structure 12. The minimal valve supports 124 can help prevent the valve segment 14 (e.g., the seal) from collapsing radially inwards in the outflow direction (i.e., towards the ventricle) when implanted in the heart. FIG. 7 shows a valve prosthesis 10D that is similar to valve prosthesis 10C of FIG. 4 except that the valve support 124 of FIG. 5 includes an aperture 97 for suturing the leaflet 16 to the valve support 124.

Figure 10B:
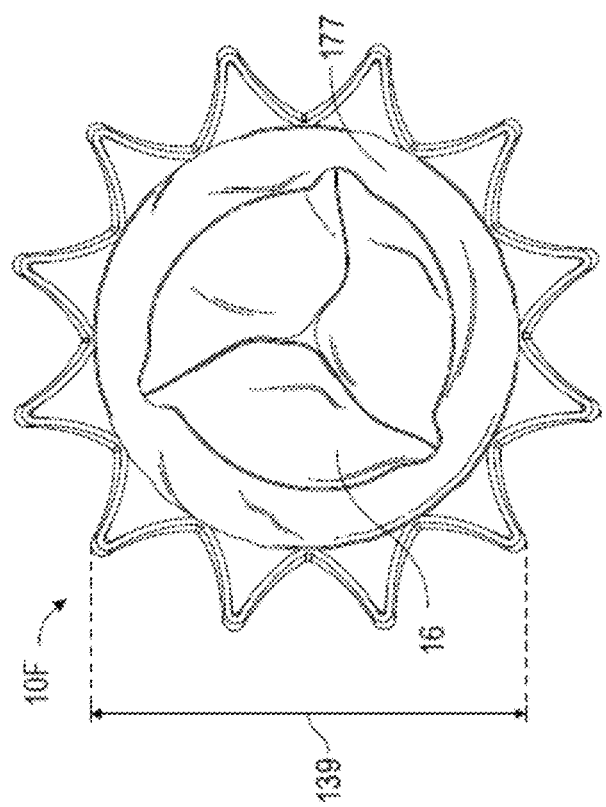
FIGS. 10A-10B show a valve prosthesis wherein the inflow edge of the valve segment is completely unsupported.
Figure 10A:
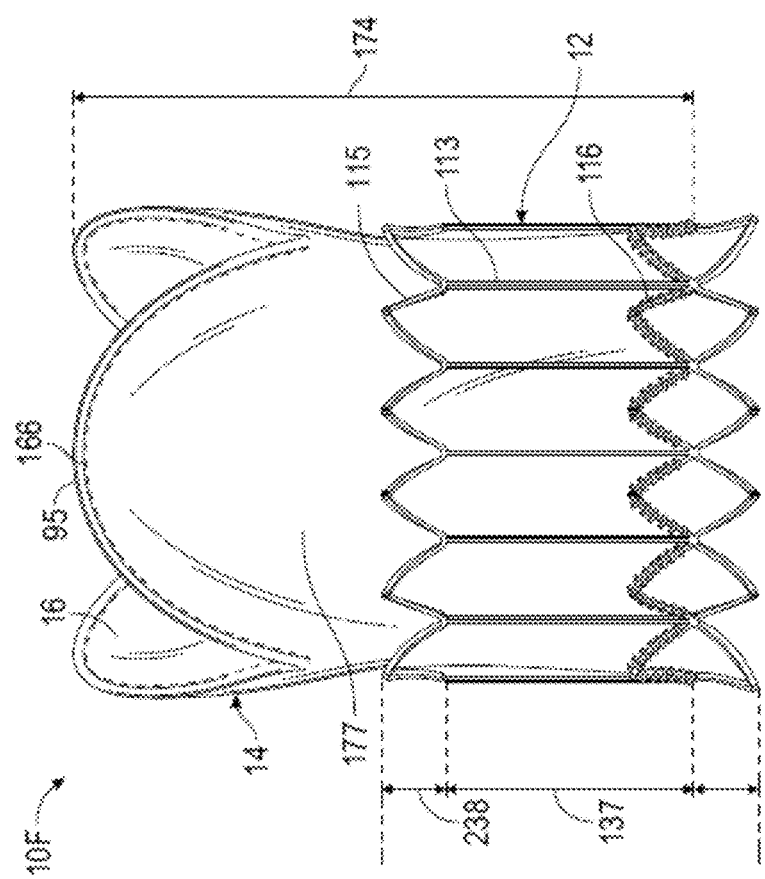

FIGS. 10A-10B show a valve prosthesis 10F wherein the inflow edge 95 of valve segment 14 is completely unsupported (i.e., does not include any valve supports thereto).

Figure 11B:
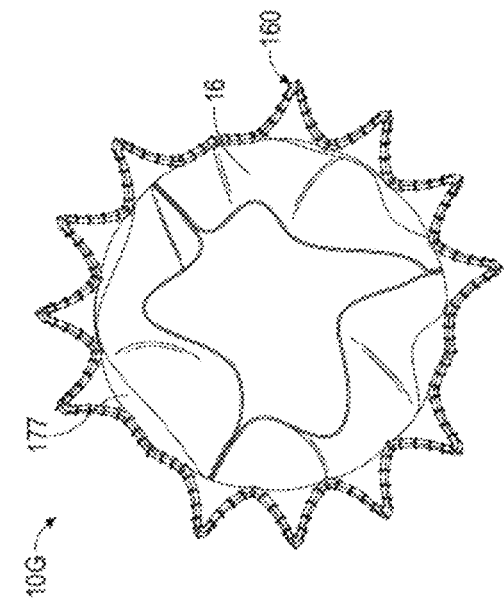
FIGS. 11A-11C show another valve prosthesis wherein the inflow edge of the valve segment is completely unsupported.
Figure 11C:
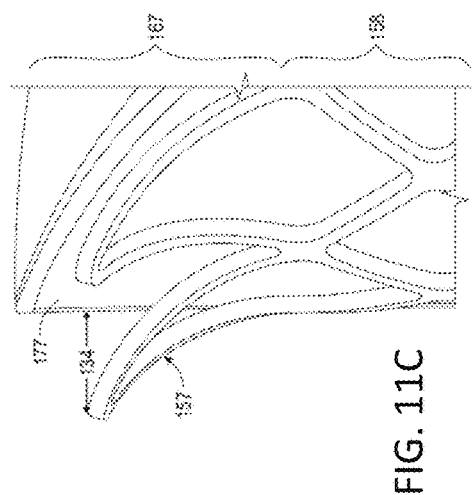
Figure 11A:
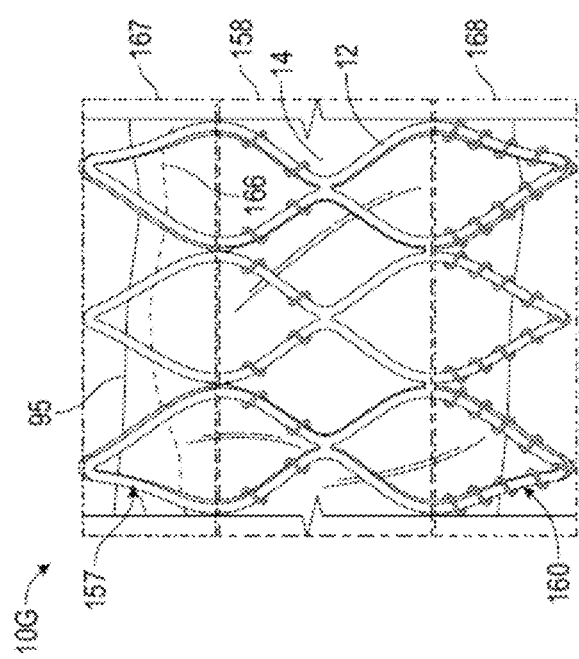

FIGS. 11A-11C show another valve prosthesis 10G wherein the inflow edge 95 of valve segment 14 is completely unsupported (i.e., does not include any valve supports thereto). Indeed, as shown in FIGS. 11A-11C, the prosthesis 10G can include an inflow portion 167, a central annular portion 158, and an outflow portion 168. The valve segment 14 can be fully circumferentially supported by the frame structure 12 within the central annular section 158. However, the valve segment 14 can be unsupported by and/or unconnected from the frame structure 12 in the inflow section 167. Further, the frame structure 12 can flare radially outwards within the inflow section 167. The flared portion 157 of the frame structure 12 can include a plurality of discrete flanges (i.e., formed from flared proximal arches 115) and can, for example, serve to help engage with an external anchor. Moreover, due to the flared portion 157, the valve segment 14 can be radially spaced away from the frame structure 12 within the inflow section 167 by a distance 134 (see FIG. 11C). In some embodiments, the distance 134 can be 1-10 mm, such as 2-8 mm, such as 3-5 mm. Finally, the frame structure 12 can also flare radially outwards within the outflow section 168. The flared portion 160 of the frame structure 12 can also serve to help engage with an external anchor 15. For example, the external anchor 15 can sit between the flared portions 157, 160 upon implantation.

FIGS. 8A-8B show another valve prosthesis 10H that is similar to valve prosthesis 10G of FIGS. 11A-11C except that substantially all of the inflow edge 95 extends proximally beyond the proximal arches 115 of the frame structure 12. When the leaflets are closed (as shown in FIG. 8B), the fluid pressure can act to fill the space created by the leaflets 16 and the seal 177, thereby preventing inward motion or collapse of the valve segment 14.

Figure 12A:
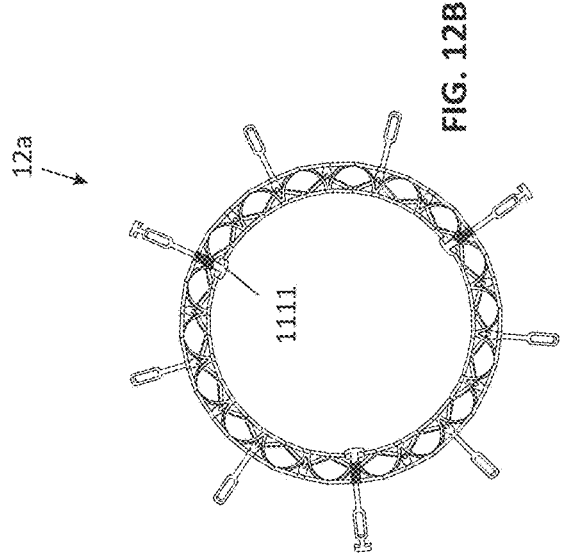
FIGS. 12A-12F show a frame structure including a close-up of commissure attachment mechanisms.
Figure 12C:
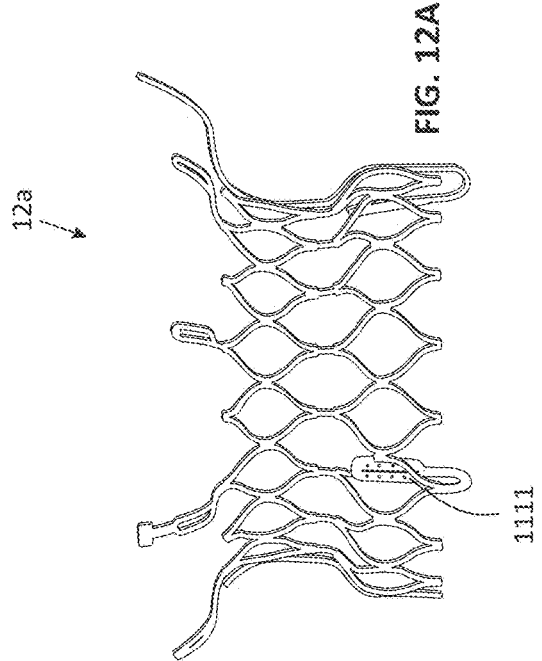
Figure 12B:
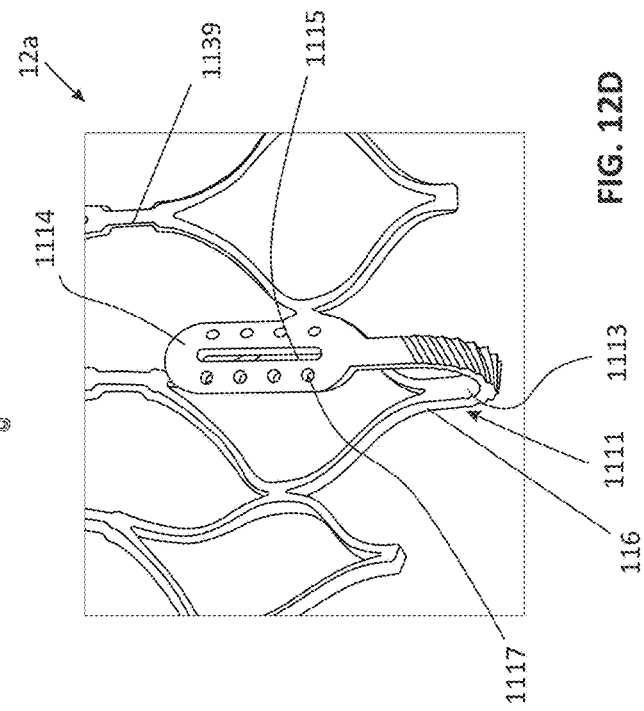
Figure 12D:
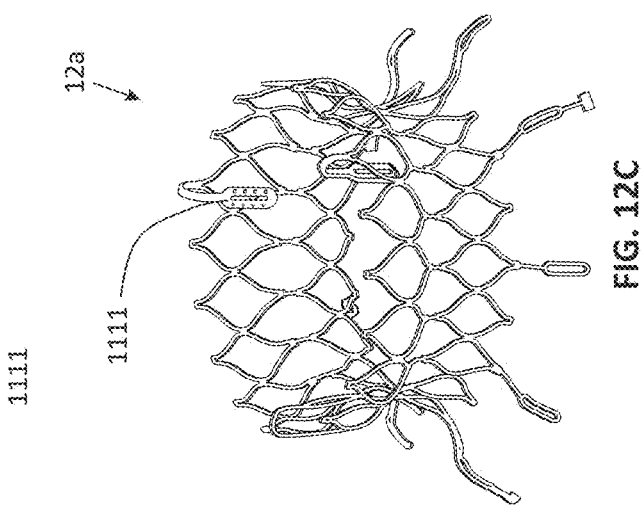
Figure 12E:
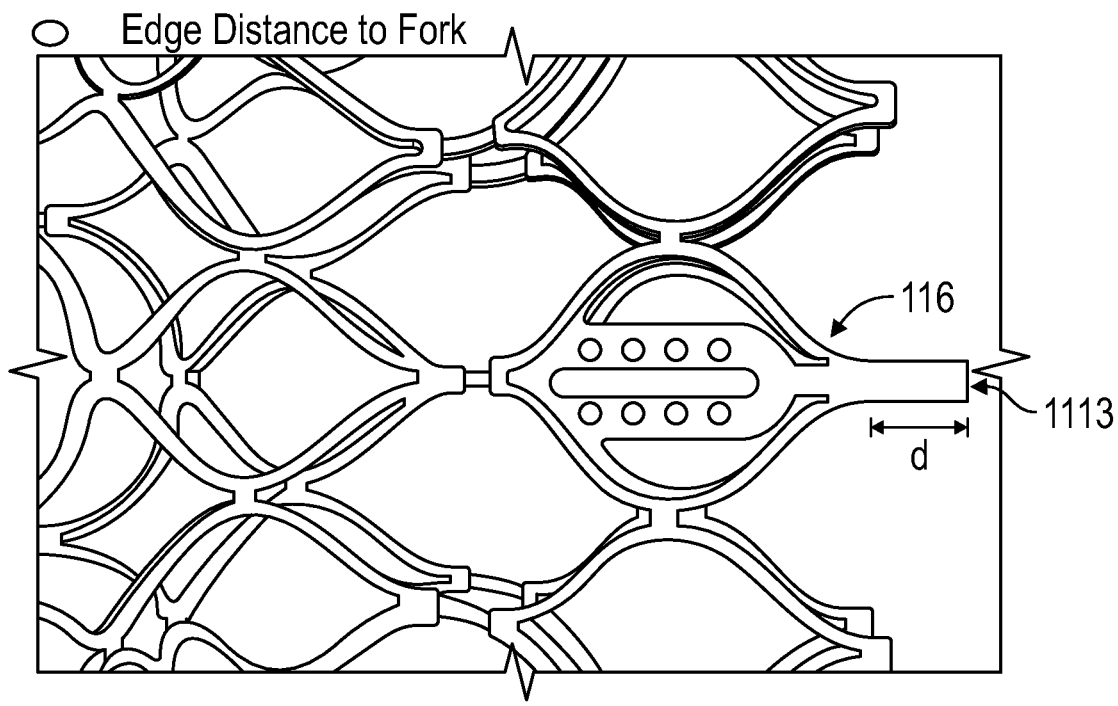
Figure 12F:
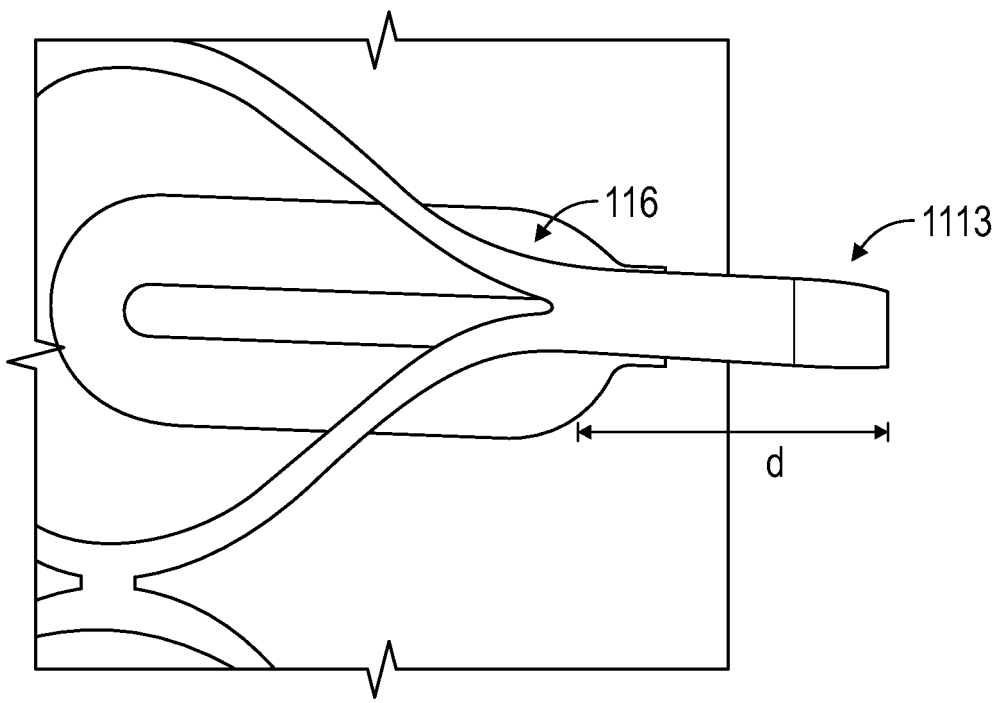

Referring to FIGS. 12A-12D, and particularly to FIG. 12D (which shows a close-up of the attachment mechanisms 1111), the interior commissure attachment mechanisms 1111 can each include a distal post 1113 that extends continuously from the distal end of a distal arch (e.g., crown, or apex) 116 (i.e., the distal-most portion of a cell 122) of the frame structure 12a and curves radially inwards, such as by approximately 180 degrees. The commissure attachment mechanisms 1111 can be integrally formed with the valve frame 12, which provides a number of advantages, including simplifying the manufacturing process, increasing mechanical strength, reducing wear, and requiring no separate attachment mechanism. As shown in FIGS. 12E-12F, the distal post 1113 can have a distance d from the distal end of distal arch 116 until where the distal post curves radially inwards. In some embodiments, this distance d can be approximately 2.5 mm long+/−0.25 mm. In other embodiments, this distance d can range from 2-4 mm. The commissure attachment mechanisms 1111 can each further include a rounded paddle 1114 (e.g., continuous with the post 1113) that includes a slot 1115 therethrough configured to pass a portion of the leaflets 16 (e.g., tabs 1661a and 1661b shown in FIG. 13C) therethrough. The slot 1115 can be surrounded by a plurality of sutures holes 1117 configured to enable sewing attachment of the leaflets 16 to the attachment mechanisms 1111.

Figure 13A:
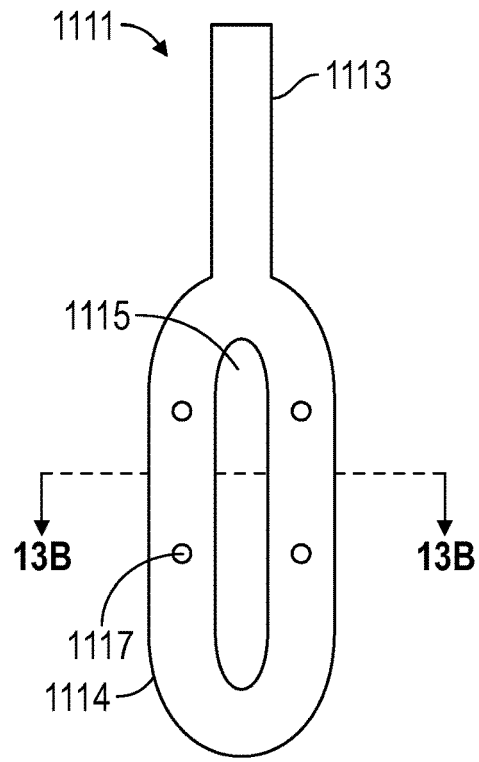
FIGS. 13A-13E illustrate one example of leaflets attached to the frame structure.
Figure 13B:
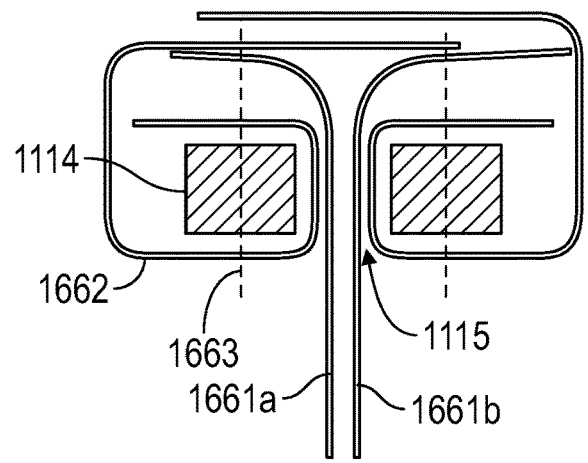
Figure 13C:
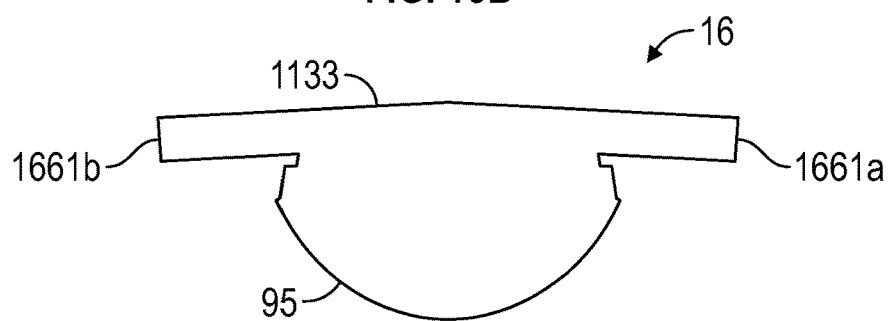
Figure 13E:
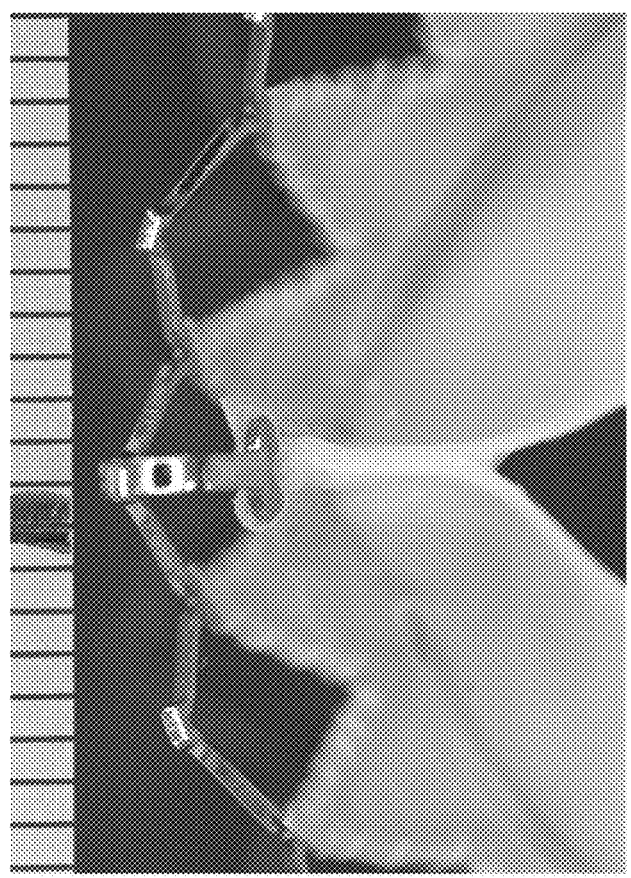
Figure 13D:
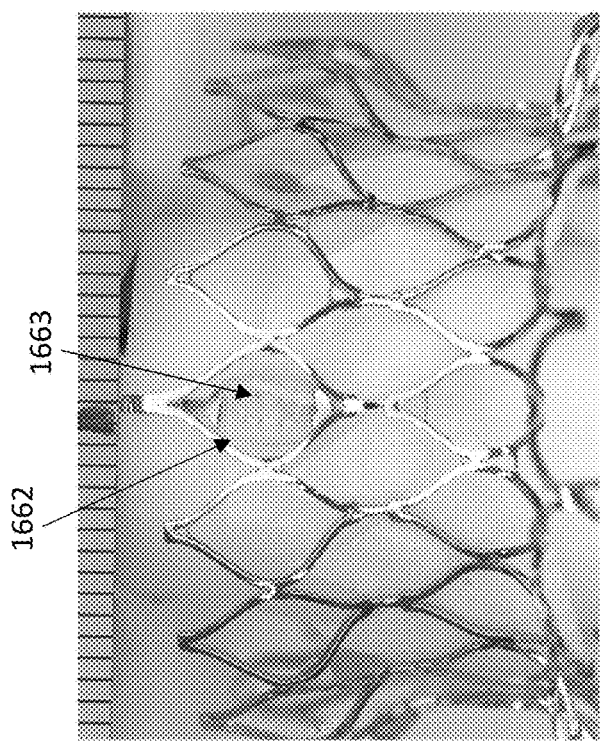

As shown in FIGS. 13A-13C, each of the leaflets 16 can include an inflow edge 95, and a tab 1661a/1661b at each commissure extending radially and parallel with the outflow (e.g., free) edge 1133. To attach the leaflets 16 to the attachment mechanisms 1111, the tabs 1661 a/1661b can be passed through the slot 1115, folded around the exterior of the paddle 1114, and sewn thereto with a suture 1663 passing through the suture holes 1117. Referring to FIGS. 13B-C, a first tab 1661a of a leaflet 16 can pass through a slot of a first attachment mechanism, and a second tab 1661b can pass through a slot of a second attachment mechanism. Each attachment mechanism is configured to receive a single tab of two adjacent leaflets (e.g., tab 1661a from a first leaflet and tab 1661b from a second leaflet). It should be understood that, when looking at FIG. 13B, two adjacent leaflets are attached to the tab (not two tabs from the same leaflet). In some embodiments, an additional layer 1662 of fabric can be positioned between the tabs 1661a/1661b and the paddle 1114 to provide a cushion and/or to prevent rubbing of the leaflets 16 against the paddle 1114. This additional piece of fabric can optionally be wrapped around the paddle 1114 and be secured on the other side with the suture, as shown. FIG. 13D shows overlap of the additional layer 1662 of fabric on the back side of the attachment mechanisms 1111, which is sewn onto the attachment mechanism 1111 with suture 1663. FIG. 13E shows a view looking from the outflow edge at the leaflets 16 where they attach to the attachment mechanism 1111 and the additional layer 1662 of fabric.

In some embodiments, the commissure attachment mechanisms 1111 can have a width or thickness that is greater than the width or thickness of the cell strut or distal arch 116 or other cells 122 of the frame structure 12a. In some embodiments, this increased width or thickness of the commissure attachment mechanism 1111 can help ensure that the attachment mechanism 1111 stays substantially rigid and/or unbending even during opening and closing of the leaflets 16. In other embodiments, the increased width or thickness of the attachment mechanism 1111 can be configured to enable slight bending, thereby distributing strain between the commissure attachment mechanism 1111 and the frame 12a.

Figure 14C:
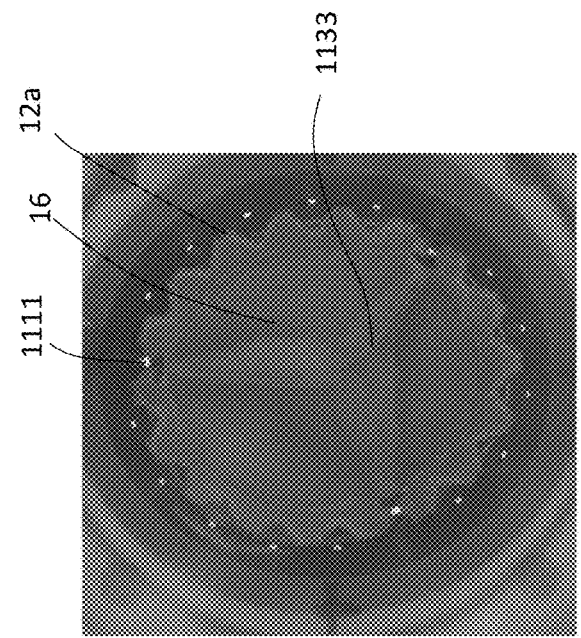
FIGS. 14A-14C illustrate the leaflets closing.
Figure 14B:
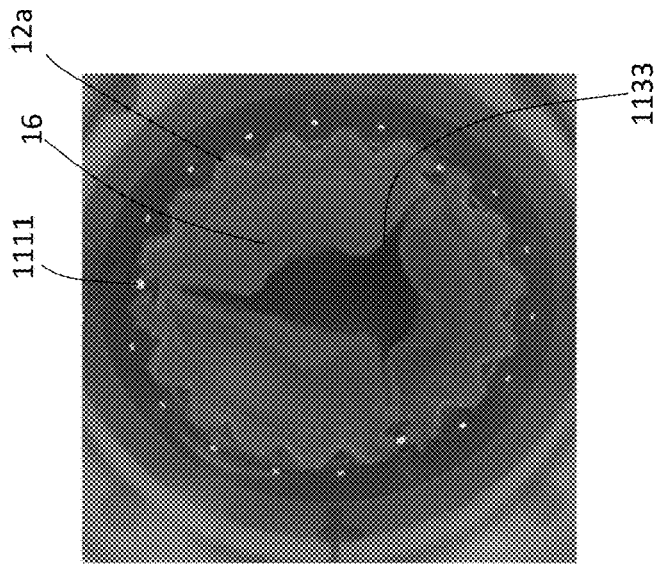
Figure 14A:
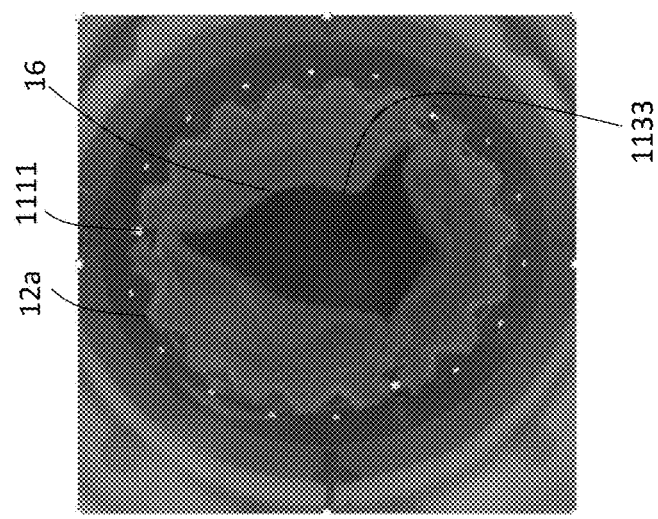

As shown in FIGS. 14A-14C (leaflets closing) and 15A-15C (leaflets opening), the interior commissure attachment mechanisms 1111 can hold the outflow edge 1133 of the leaflets 16 away from the inner perimeter (e.g., diameter) of the frame structure 12a during both opening and closing of the leaflets 16. Referring to FIGS. 16A-16C, for example, the interior commissure attachment mechanisms 1111 can hold the outflow edge 1133 of the leaflets 16 a distance d away from the interior diameter ID of the frame 12a, such as 1.5 mm-4 mm away, such as 2-3 mm, such as approximately 2.5 mm away. Because the outflow edge 1133 of the leaflets 16 is held away from the inner diameter of the frame 12a during both opening and closing of the leaflets 16, deformation to the leaflets 16 is minimized even when the frame structure 12a is deformed (e.g., upon implantation). Additionally, the spacing between the leaflets 16 and the inner diameter of the frame structure 12a can advantageously enable more blood to flow through that area while the leaflets 16 are opening to help prevent blood stagnation between the frame 12a and the leaflets 16. Finally, the spacing between the leaflets 16 and the inner diameter of the frame structure 12a can help maintain durability of the leaflets 16 (i.e., prevent frictional wear of the leaflets 16 over time). In some embodiments, the leaflets are configured to open to a radius that is greater than a radius of the commissure attachment mechanism but less than a radius of the diameter or perimeter of the frame structure.

As a result of the interior commissure attachment mechanism 1111, the attached edges of the leaflets 16 can extend substantially straight down from the central annular portion 101 (i.e., without curving radially outwards). The free (e.g., outflow) edge of the leaflet (e.g., between commissure attachment mechanisms 1111) can open to a radius that is greater than id, without contacting frame 12a. That is, as shown in FIGS. 16A-16D, the inner diameter id and/or circumference formed by the commissure attachment mechanisms 1111 can be approximately equivalent to the inner diameter id and/or circumference of the frame 12a at the central annular portion 101. Thus, the leaflets 16 can form a substantially cylindrical flow path for blood passing therethrough. In FIG. 16D, an outline 161 of the leaflet material is shown when opened. Specifically, an offset allows for increased expansion of the leaflet (into the "gap"), without contacting the frame. This increases blood flow space, without deforming leaflet attachment (from that cylindrical profile).

In some embodiments described herein, the inflow edge 95 of the leaflets can be entirely unsupported except at commissures of the leaflets 16, such as except for at the interior commissure attachment mechanism 1111 and/or the minimal valve supports 124.

FIGS. 17A-17D show further details of the frame 12a. The frame 12a can include a plurality (e.g., three) rows of cells 122 such that the first row of cells is in the atrial flared portion 102, the second row in the central annular portion 101, and the third row of cells in the ventricular flared portion 103. The cells 122 can be substantially diamond shaped and thus can foreshorten during deployment (e.g., expansion). Further, the row of cells 122 in the central annular portion 101 can include axially extending narrowed struts 123 therein that are non-foreshortening. Additionally, the atrial flared portion 102 of frame 12a can include a plurality of eyelets 222 (e.g., oval eyelets) extending from the vertex of some or all of the atrial cells 122 (for example, from every other vertex as shown in FIGS. 17A-17D). The eyelets 222 can be configured to remain above (or proud of) other portions of the atrial flared portion 102 when implanted and can advantageously enable grasping and/or manipulation of the valve frame 12 (e.g., with a hook or suture) during deployment. The eyelets 222 can be connected to the arches (or vertices) of the cells 122 via a straight extension 132. The straight extension 132 can be non-foreshortening during deployment, which can advantageously help with trackability and sheathing of the atrial flared portion 102 during delivery of the frame 12a. The non-foreshortening extensions 132 can additionally advantageously provide increased apposition on the atrial side, allowing for a reduction in length of the foreshortening elements (e.g., the diamond-shaped cells 122) and thus increasing radial stiffness of the valve frame 12a. In some embodiments, the length of the non-foreshortening extensions 132 can be selected to match the size of the atrial brim of the frame with a given anatomy at an implantation site. The base valve structure can remain the same even when the length of these extensions is adjusted. This creates the ability to provide frames with a plurality of different atrial brim sizes while the rest of the frame has consistent dimensions. The frame 12a can further include a plurality of (e.g., three) frame tabs 144 extending from the eyelets 222 and configured to engage with a valve delivery system for deployment. In one embodiment, each of the frame tabs 144 can be spaced apart by 120°. As shown in FIG. 17A, the frame 12a can have an overall height of 24 mm and a landing height (e.g., "landing zone", height within which the anchor is configured to rest) of 4 mm. As shown in FIG. 17D, the frame 12a can have a ventricular diameter of 35 mm.

Figure 18A:
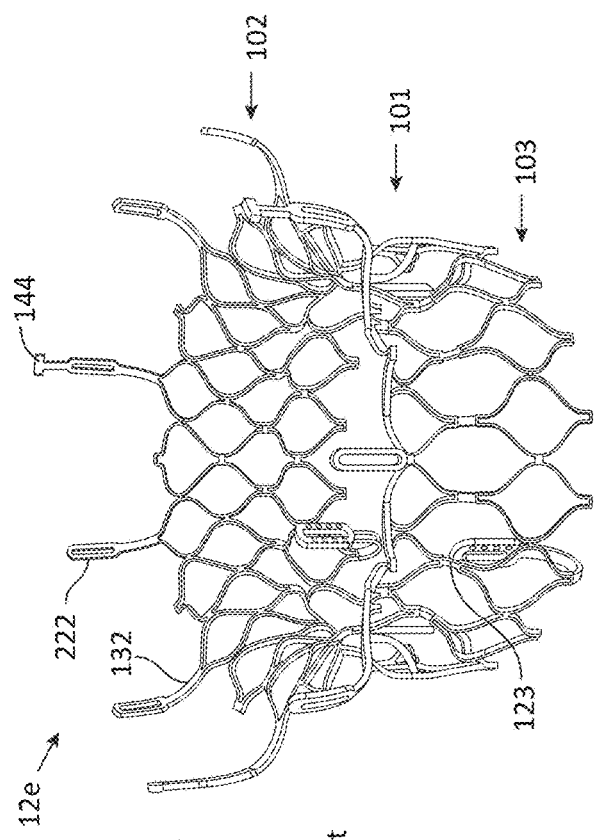
FIGS. 18A-18D illustrate another example of a frame structure.
Figure 18B:
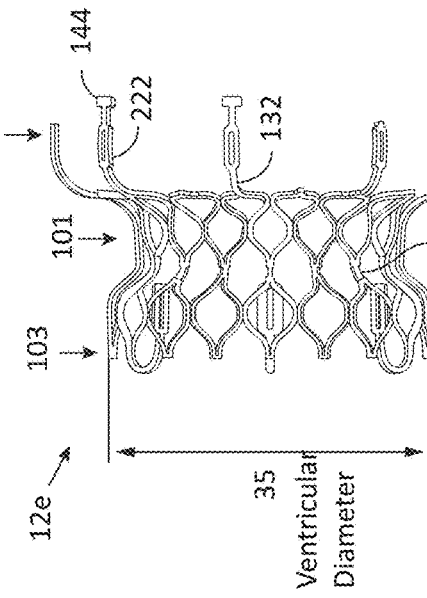
Figure 18C:
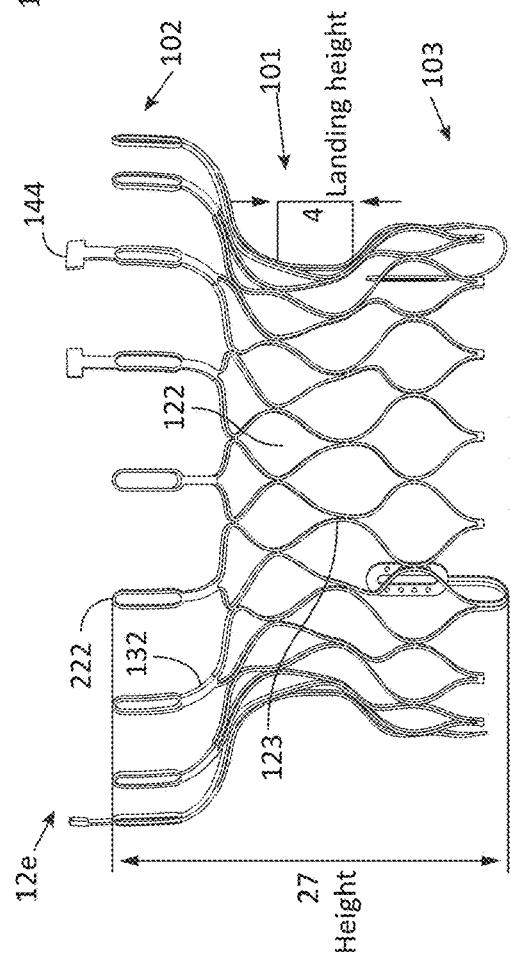
Figure 18D:
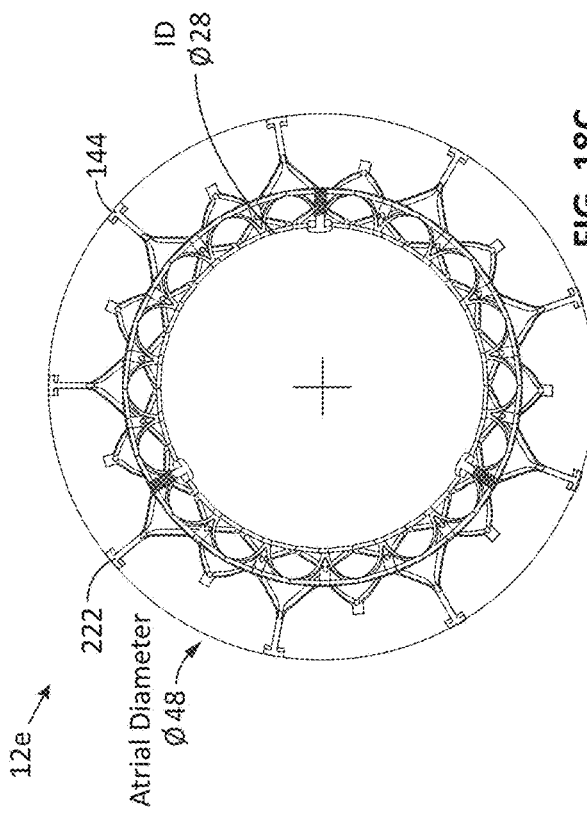

Another exemplary frame 12e is shown in FIGS. 18A-18D. The frame 12e is similar to frame 12a except that frame 12e includes four rows of cells 122. The rows of cells 122 can be configured such that there is an extra row of cells in the atrial flared portion 102 (i.e., such that that there is one row of cells in the ventricular flared portion 103, one row of cells in the central annular portion 101, and two rows of cells in the atrial flared portion 102). Additionally, the cells 122 in the atrial flared portion 102 can be flared further radially outwards in the frame 12e than the frame 12a so as to better engage with the atrial wall proximate to the annulus. Further, the straight extensions 132 can be curved so as to point the eyelets 222 substantially in the axial direction (i.e., towards the atrium). The additional row of cells 122 on the atrial side can advantageously increase the stiffness of the atrial flared portion 102, thereby helping to anchor the atrial flared portion 102 in the atrium (and/or pull the anchor up towards the annulus upon deployment of the frame 12e). Frame 12e can have an overall height of 27 mm and a landing height of 4 mm. As shown in FIG. 18D, the frame 12e can have a ventricular diameter of 35 mm.

Figure 19A:
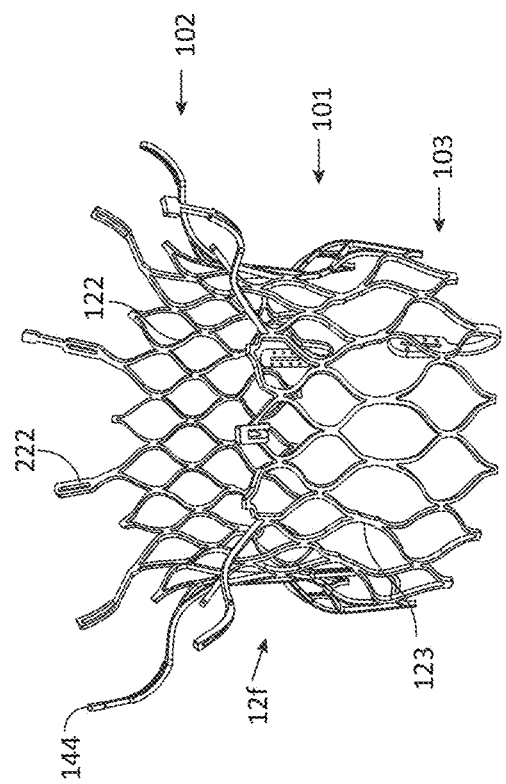
FIGS. 19A-19D illustrate one example of a frame structure.
Figure 19C:
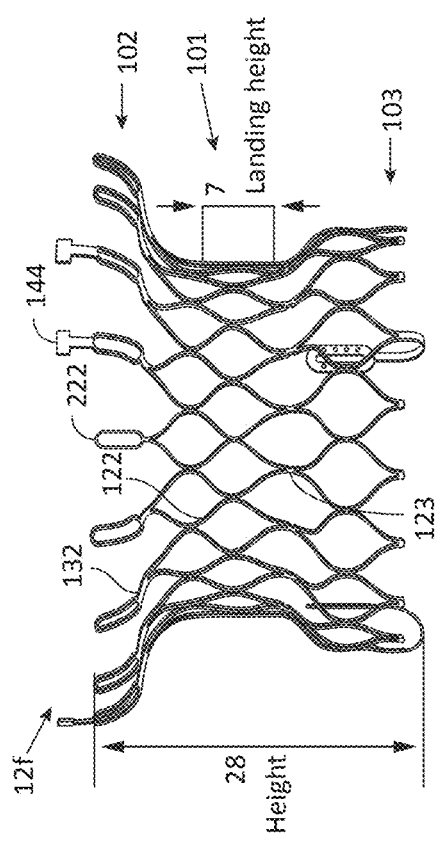
Figure 19B:
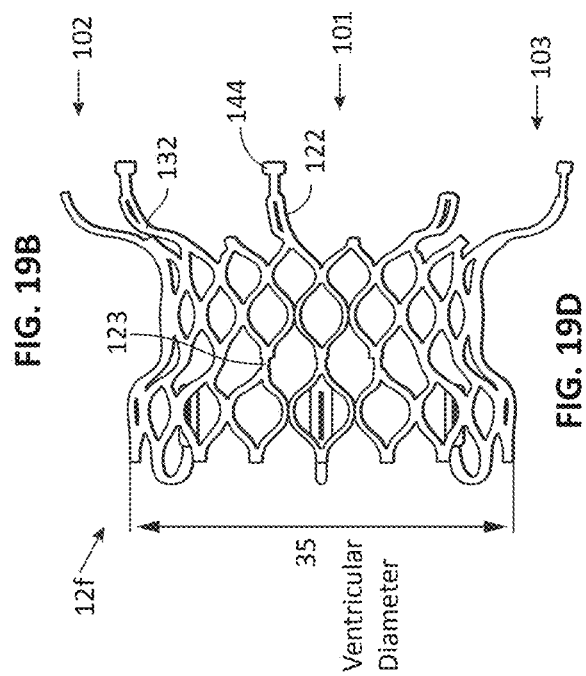
Figure 19D:
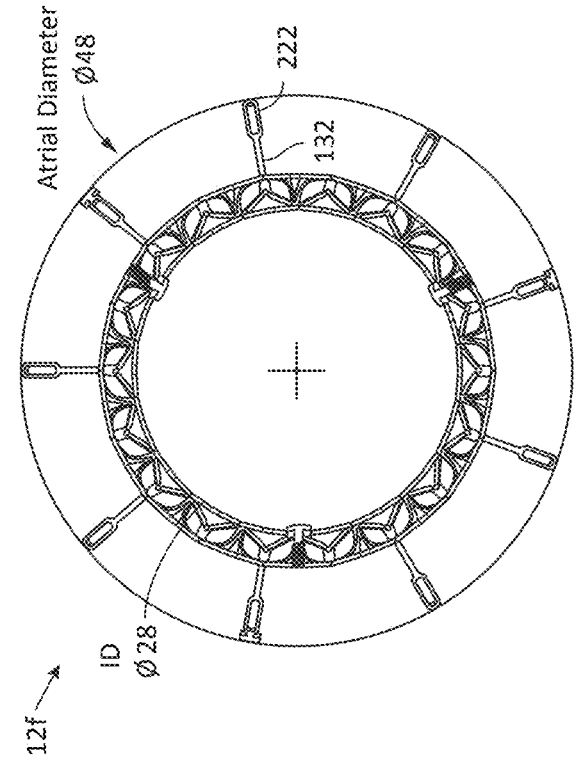

Another exemplary frame 12f is shown in FIGS. 19A-19D. The frame 12f is similar to frame 12e except that the additional row of cells 122 at the atrial end is flared less radially outwards (i.e., the vertices can point more in the axial direction rather than outwards in the radial direction). Reducing the amount of flaring can increase the landing zone height, which can better enable the anchor 15 to be positioned against the central annular portion 101. Frame 12f can have an overall height of 28 mm and a landing height of 7 mm. As shown in FIG. 19D, the frame 12f can have a ventricular diameter of 35 mm.

Another exemplary frame 12g is shown in FIGS. 20A-20D. The frame 12g is similar to frame 12e except that the atrial-most cells 122 are lengthened so as to extend up to the axial location of the eyelets 222 (eliminating straight extensions 132). This increase in length of the atrial-most cells 122 can result in the vertices pointing more axially, thereby making the vertices less traumatic. Like frame 12e, the frame 12g can have an overall height of 27 mm and a landing height of 4 mm. As shown in FIG. 20D, the frame 12g can have a ventricular diameter of 35 mm.

A table showing exemplary dimensions for frames 12a, 12e, 12f, and 12g is shown in FIG. 21. Referring to the table of FIG. 21, all of the frames can have an ID of 28 mm and a ventricular OD of 35 mm. However, the atrial OD is adjusted between the frames, ranging from 47 mm for the 12a frame up to 49 mm for the 12g frame. The expanded height can also vary between the frames, ranging from 24 mm for frame 12*a*, 27 mm for frame 12*e* and 12*g*, and 28 mm for frame 12*f*. The landing height of the frames can be about 4 mm for the 12*a*, 12*e*, and 12*g* frames, and about 7 mm for frame 12*f*. The ventricular height can be about 14 mm for frames 12*a*, 12*e*, and 12*g*, and about 18 mm for frame 12*f*. Frame 12*a* can have a sheathed height of less than 33 mm, while frames 12*e*, 12*f*, and 12*g* can have sheathed heights of less than 38 mm.

Another exemplary frame 12*h* is shown in FIGS. 22A-22B. The frame 12*h* is similar to frame 12*g* except that the atrial flared portion 102 flares further outward to a larger radius. Additionally, the distal-most cells 122 are more elongate. Finally, the landing height can be slightly larger at approximately 4-5 mm.

Figure 23A:
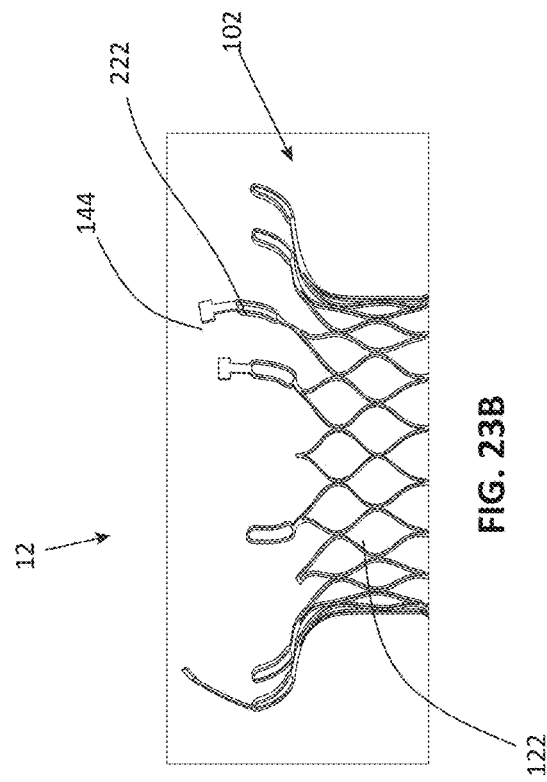
FIGS. 23A-23D illustrate another example of a frame structure.
Figure 23B:
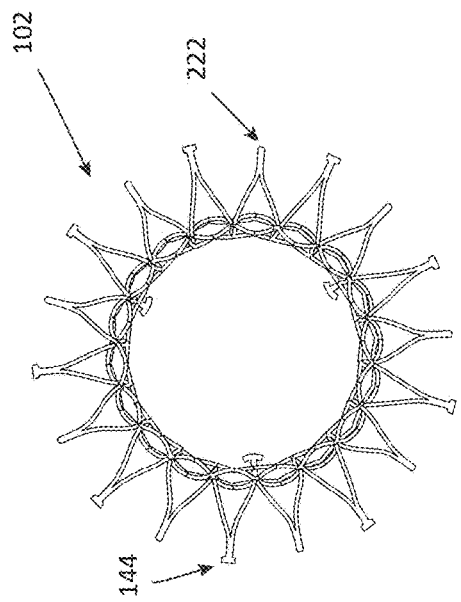
Figure 23C:
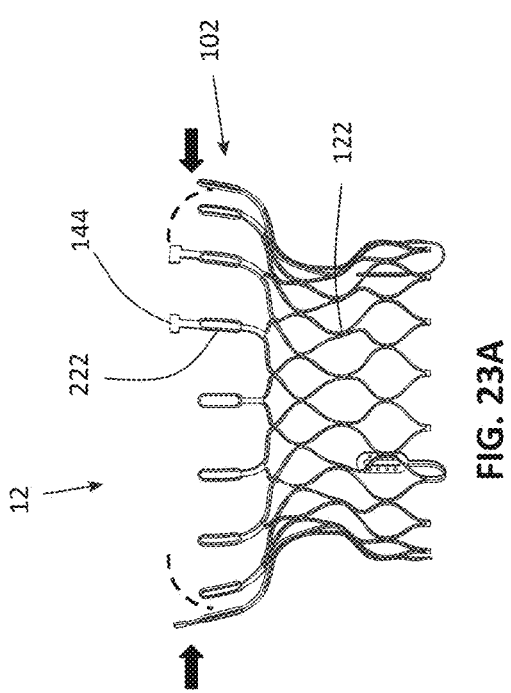
Figure 23D:
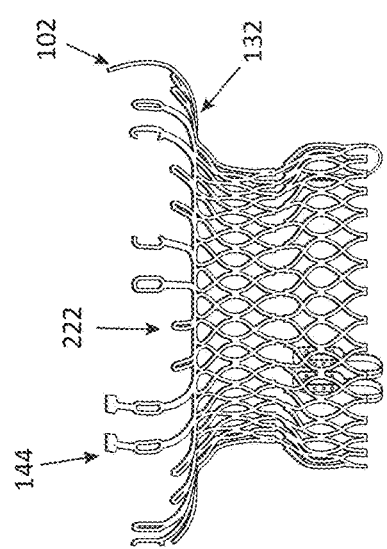
Figure 24B:
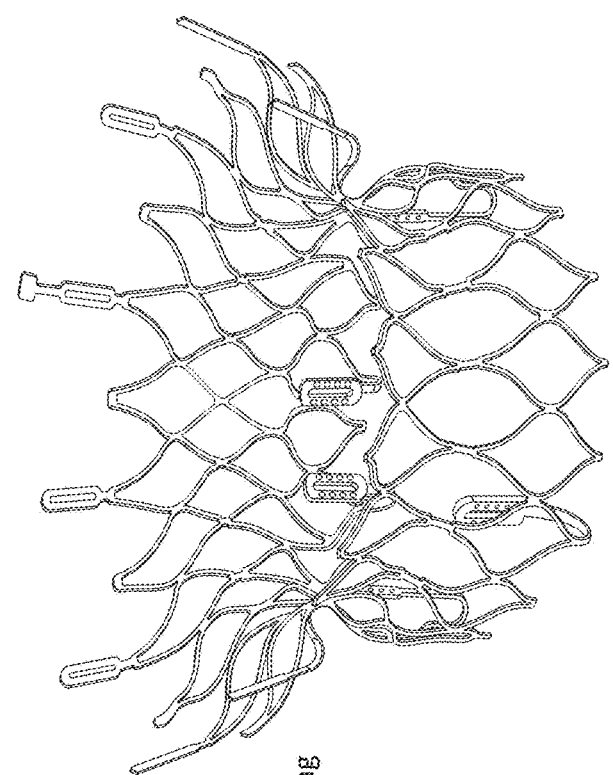
FIGS. 24A-24D illustrate one example of a frame structure.
Figure 24D:
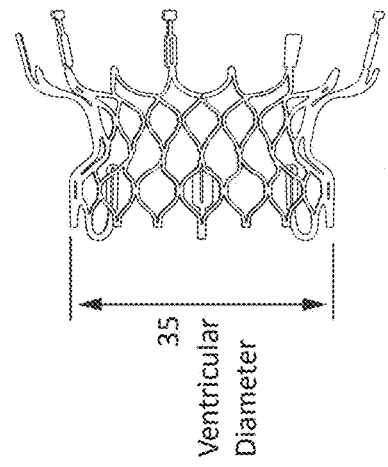
Figure 24A:
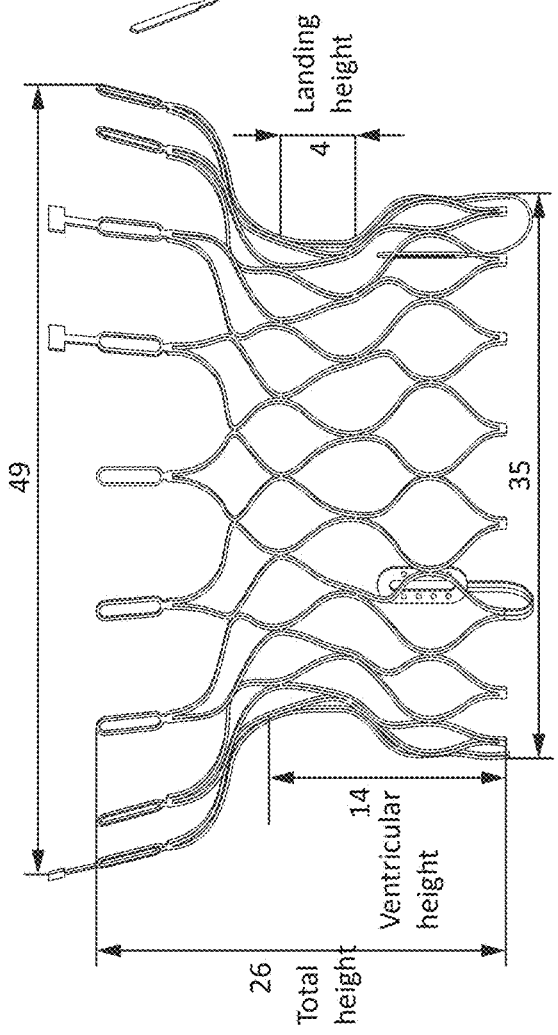
Figure 24C:
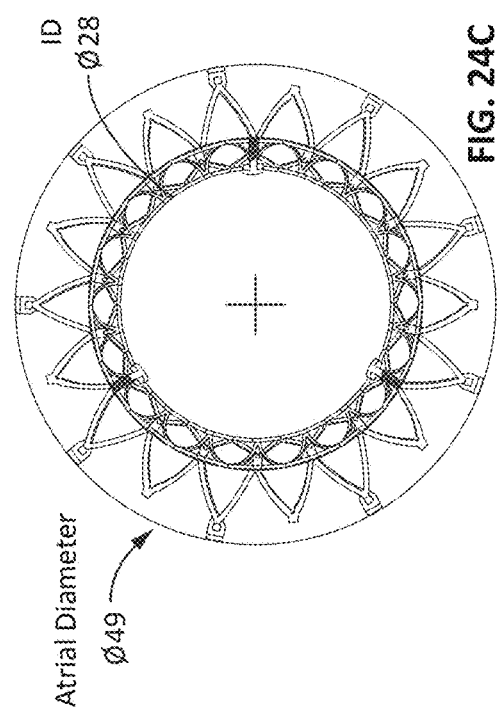

Referring to FIGS. 23A-23B, any of the frames 12 described herein (e.g., frames 12*a*-12*h*) can be modified such that the atrial flared portion 102 curves around (e.g., in a C-shape) such that the distal tips point radially inwards. Doing so can help reduce trauma to the atrium when the valve prosthesis is implanted. In some embodiments, at least some of the distal tips can point inwards with a radius of curvature below 10 mm. In another embodiment, the radius of curvature of the distal tips can be between 3-10 mm. In some embodiments, as shown in FIGS. 23C-23D the inward curvature of the atrial flared portion 102 can be formed by keeping the foreshortening cells 122 the same dimension, but increasing the length of the non-foreshortening elements on the atrial side (e.g., the straight extension 132, eyelets 222, or frame tabs 144) and curving those non-foreshortening elements upward and/or inwards.

FIGS. 24A-24D illustrate another frame embodiment with a total height of 26 mm, a ventricular height of 14 mm, a ventricular OD of 35 mm and a landing height of 4 mm. This embodiment includes longer atrial struts with no inward curvature and no extended paddle arms compared to some of the embodiments described above.

Figure 25A:
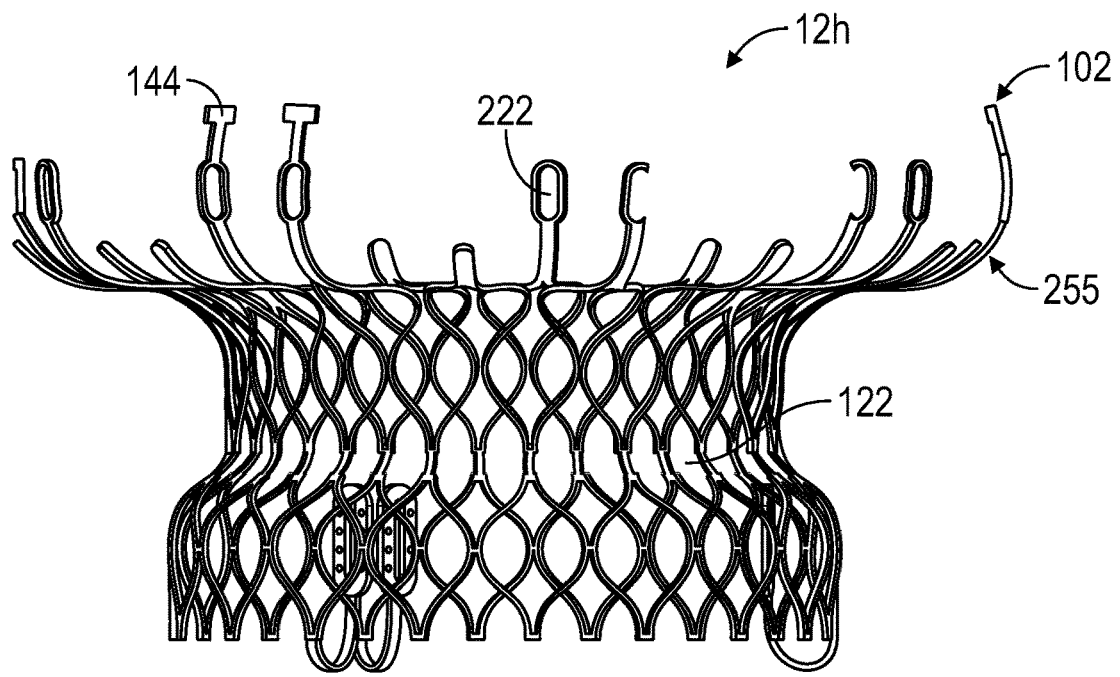
FIGS. 25A-25B illustrate another example of a frame structure.
Figure 25B:
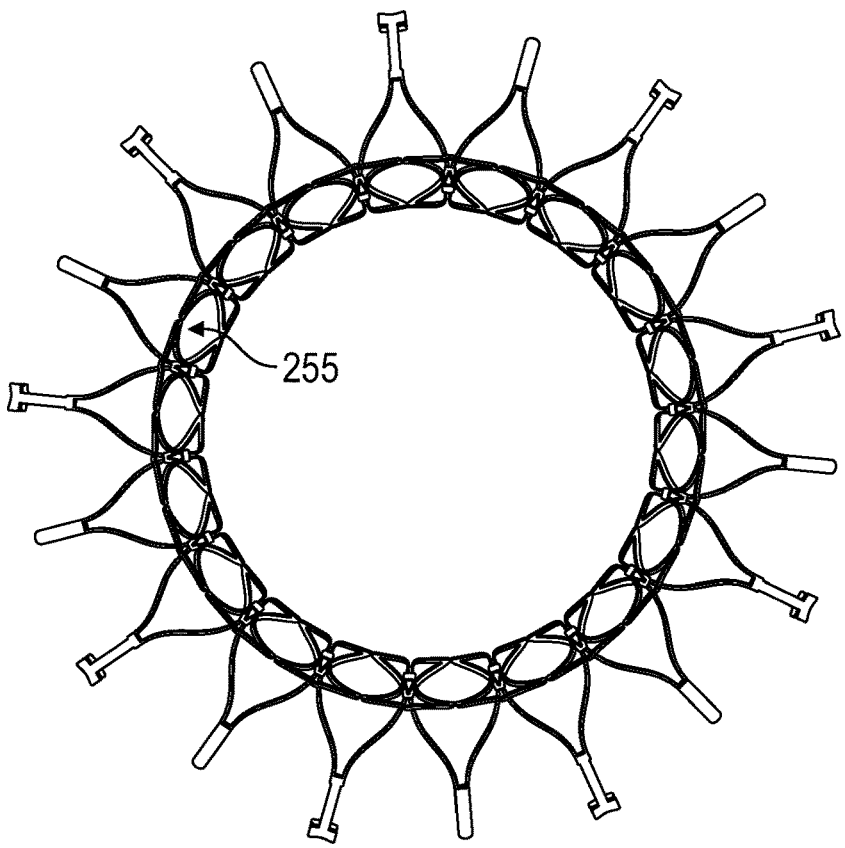

FIGS. 25A-25B illustrate another embodiment of a frame 12*h* that includes a pattern of cells 122 that terminate in a horizontal section 255 of the frame near the atrial portion 102. This allows for easier variation of the atrial brim size depending on the specific need of a particular patient. For example, in the frame 12*h* of FIGS. 25A-25B can have an atrial OD of 53 mm. In another embodiment, the length of the cells on the atrial side of the frame, such as the cells that terminate at or in the horizontal section 255, can be longer than the other cells to increase the atrial diameter of the frame.

Any of the valve frames 12 (e.g., frame 12*a*-12*h*) described herein can include one or more skirts or seals thereon. For example, the valve frame 12 can include an internal skirt and one or more external skirts. The skirts can be made, for example, of PET.

Figure 26A:
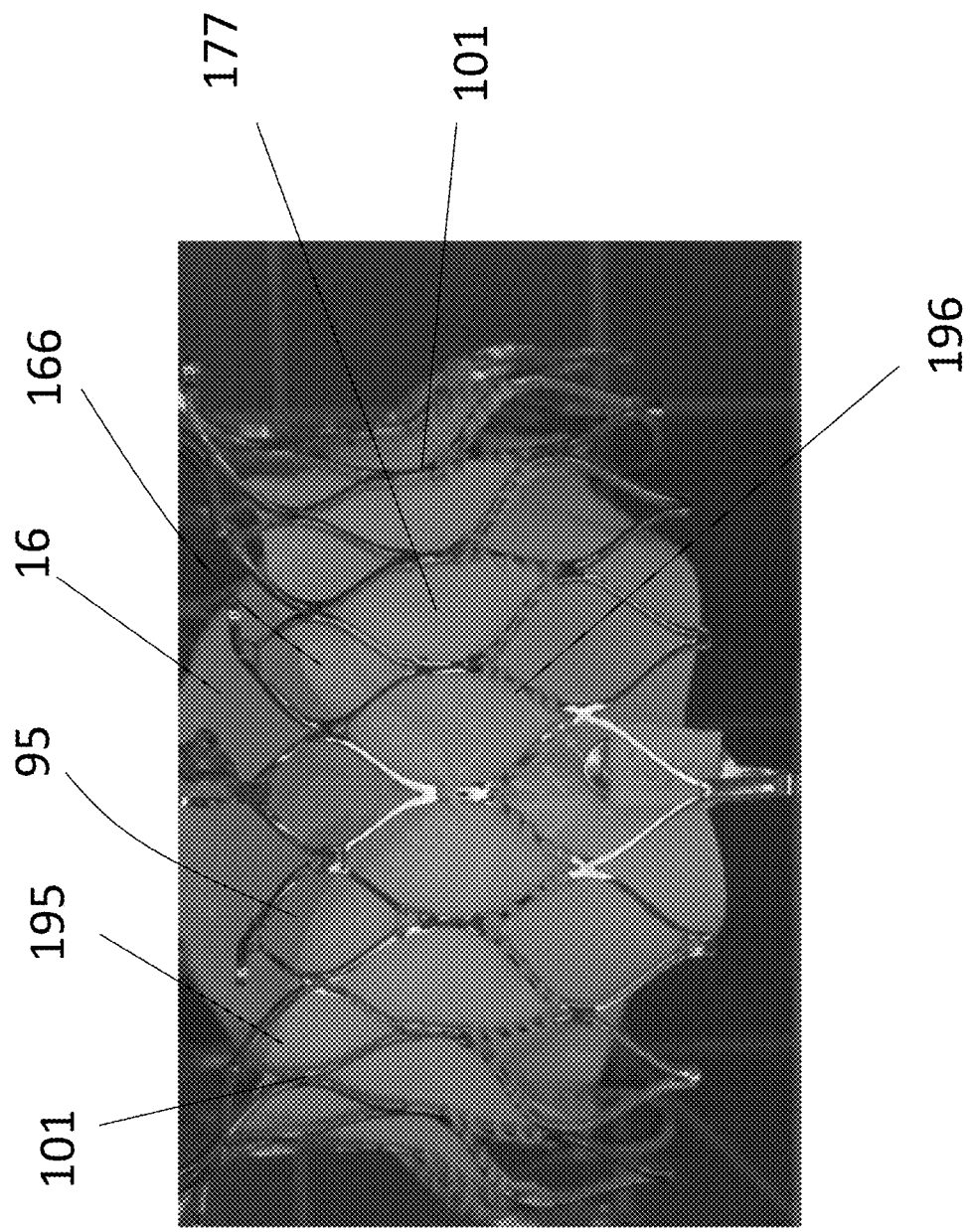
FIGS. 26A-26C illustrate an internal skirt attached to a frame.
Figure 26C:
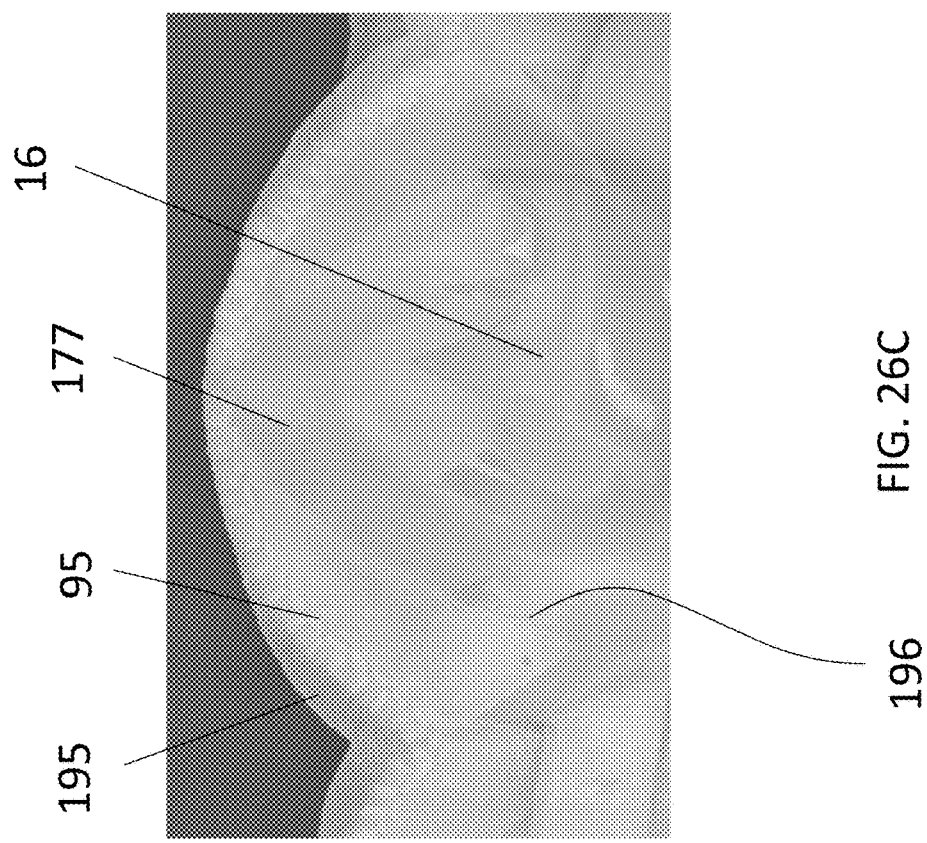
Figure 26B:
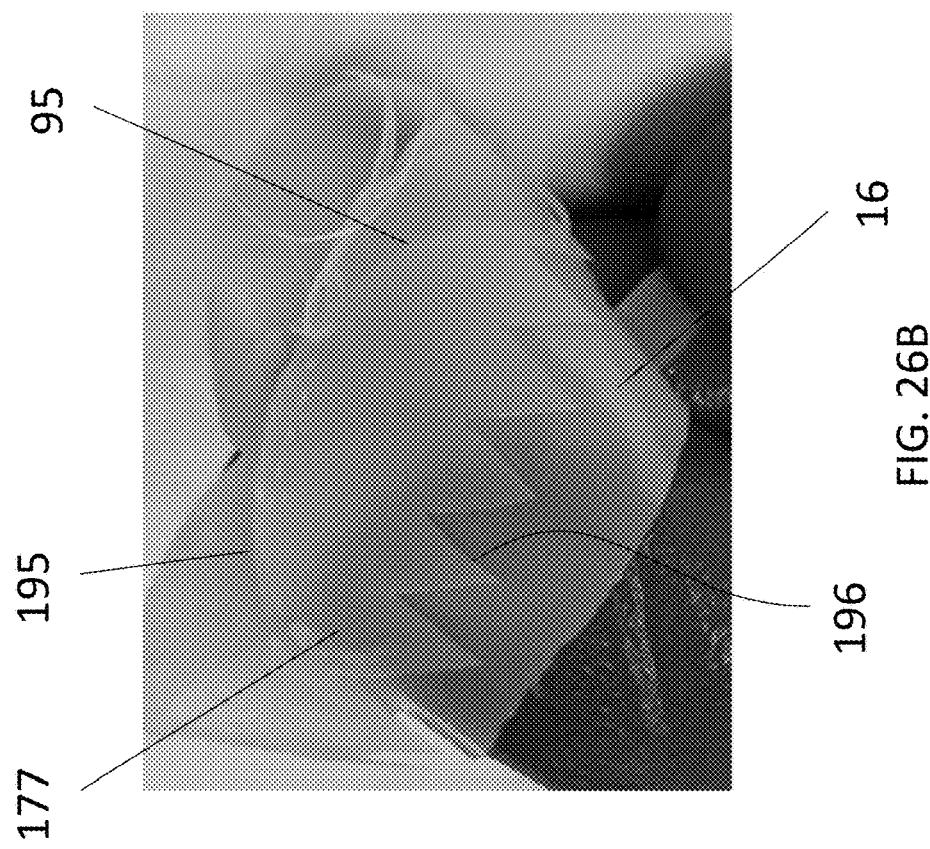

Referring to FIGS. 26A-26C, an internal skirt 177 can be attached to the internal circumference of the frame 12. The inflow edge 195 of the internal skirt 177 can include three convex segments 166 configured to at least partially conform to the inflow edges 95 of the leaflets 16. In some embodiments, as shown in FIGS. 26B-26C, the radius of curvature of the convex segments 166 of the inflow edge 195 of the internal skirt 177 can be greater than the radius of curvature of the inflow edges 95 of the leaflets 16. Further, the internal skirt 177 (e.g., the inflow edges 195) can be attached to the inflow edges 95 of the leaflets 16. The internal skirt 177 may thereby (e.g., indirectly) couple the inflow edges 95 of the leaflets 16 to the frame 12. The outflow edge 196 of the internal skirt 177 can be cut in a pattern (e.g., a zigzag or repeating triangular pattern) configured to match the cell pattern of the frame 12. The outflow edge 196 can be attached to the frame 12 within and/or distal to the central annular portion 101, and proximate to the outflow region 103. Thus, the internal skirt 177 may not extend all the way to the ventricular end of the frame 12.

Referring to FIGS. 27A-27F, in some embodiments, the ventricular flared portion 103 can further include an external skirt 225 thereon. The ventricular external skirt 225 can advantageously prevent chordae from interacting with (e.g., getting stuck in) the cells and/or tips of the ventricular flared portion 103, and/or can aid in making the ventricular flared portion 103 less traumatic. The external skirt 225 can, for example, wrap around the ventricular end of the frame 12 so as to cover the exposed vertices of the cells 122.

Figure 27F:
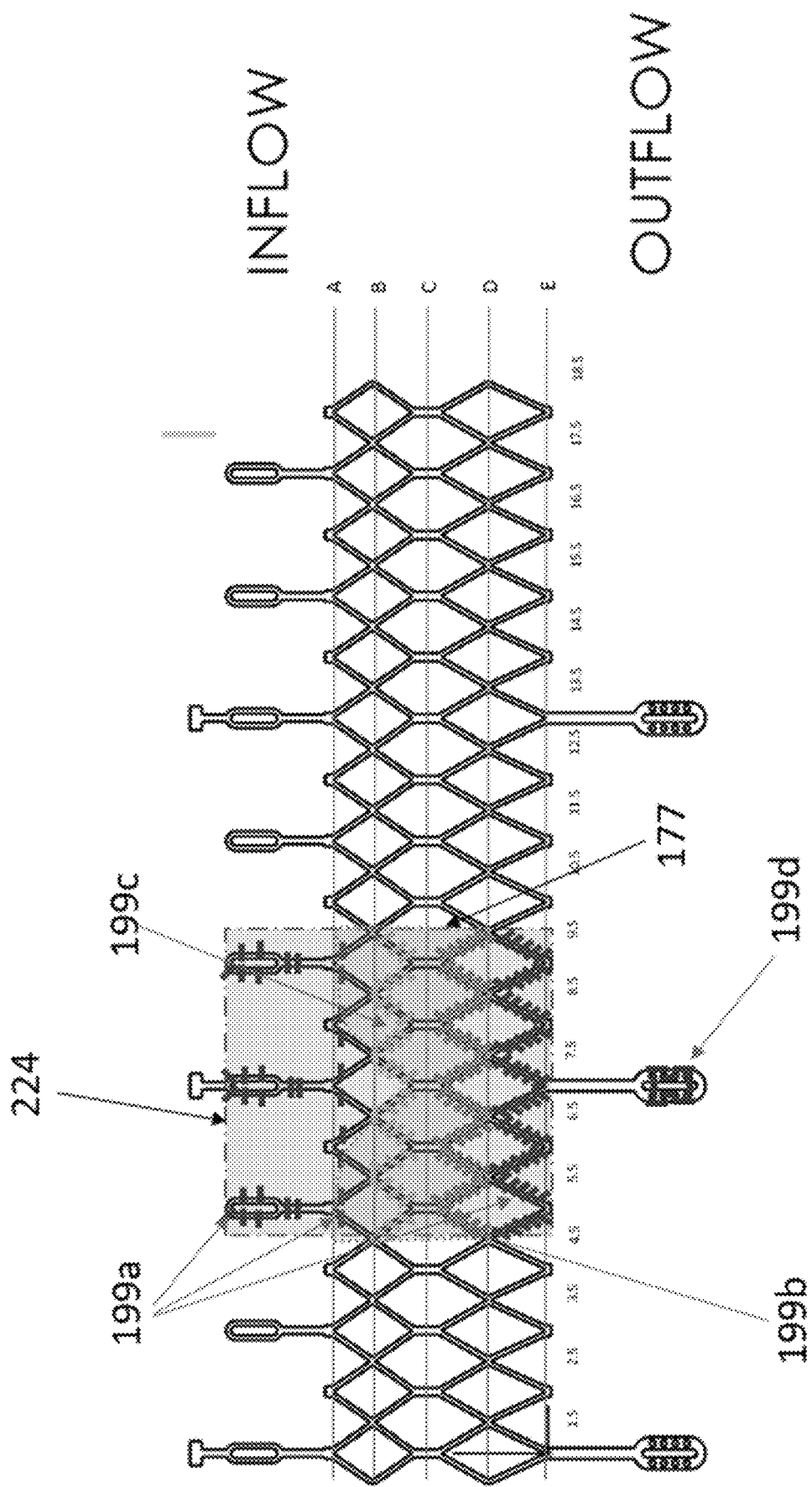

FIGS. 27A-27F also show exemplary frame attachment locations for the internal skirt 177, the atrial external skirt 224, and the ventricular external skirt 225. As best shown in FIGS. 27B, 27C, and 27D, the inner skirt 177 can be sewn to the frame 12 proximate to the tips of the atrial flare (shown by the arrows c pointing to the stitches). As shown best in FIGS. 27B-27C, the atrial external skirt 224 can be attached to the frame 12 such that the skirt tabs 229 fold over (and are sewn to) the eyelets 222 (shown by arrows a pointing to the stitches). Additionally, the atrial external skirt 224 can be sewn around the circumference of the frame 12 near the tips of the flare (shown by the arrows b pointing to the stitches). As best shown in FIGS. 27D-27E, the ventricular external skirt 225 can be attached such that the edge of the skirt 225 folds over the tips of the ventricular flare. Additionally, the ventricular external skirt 225 can be sewn to the frame 12 along the distal (ventricular)-most struts of the frame 12 (shown by the arrows d point to the stitches). In some embodiments, the external skirts 224, 225 can overlap one another proximate to the central annular circumferential portion 101. In other embodiments, the external skirts 224, 225 can have an axial space therebetween, e.g., such that a central section (e.g., the central annular portion 101) does not have an external skirt thereon.

Referring to FIG. 27F, the frame can include an internal skirt 177 and an external skirt 224. The external skirt 224 can be sewn to the frame at attachment points 199*a*. The internal skirt 177 can be sewn to the frame at attachment points 199*b*. Additionally, both the external skirt and the internal skirt can be sewn to the frame at attachment points 199*c*. Additionally, as described above, the commissure attachment mechanisms can include attachment points 199*d* for sewing attachment to a fabric strip, tissue, and the frame.

Figure 28:
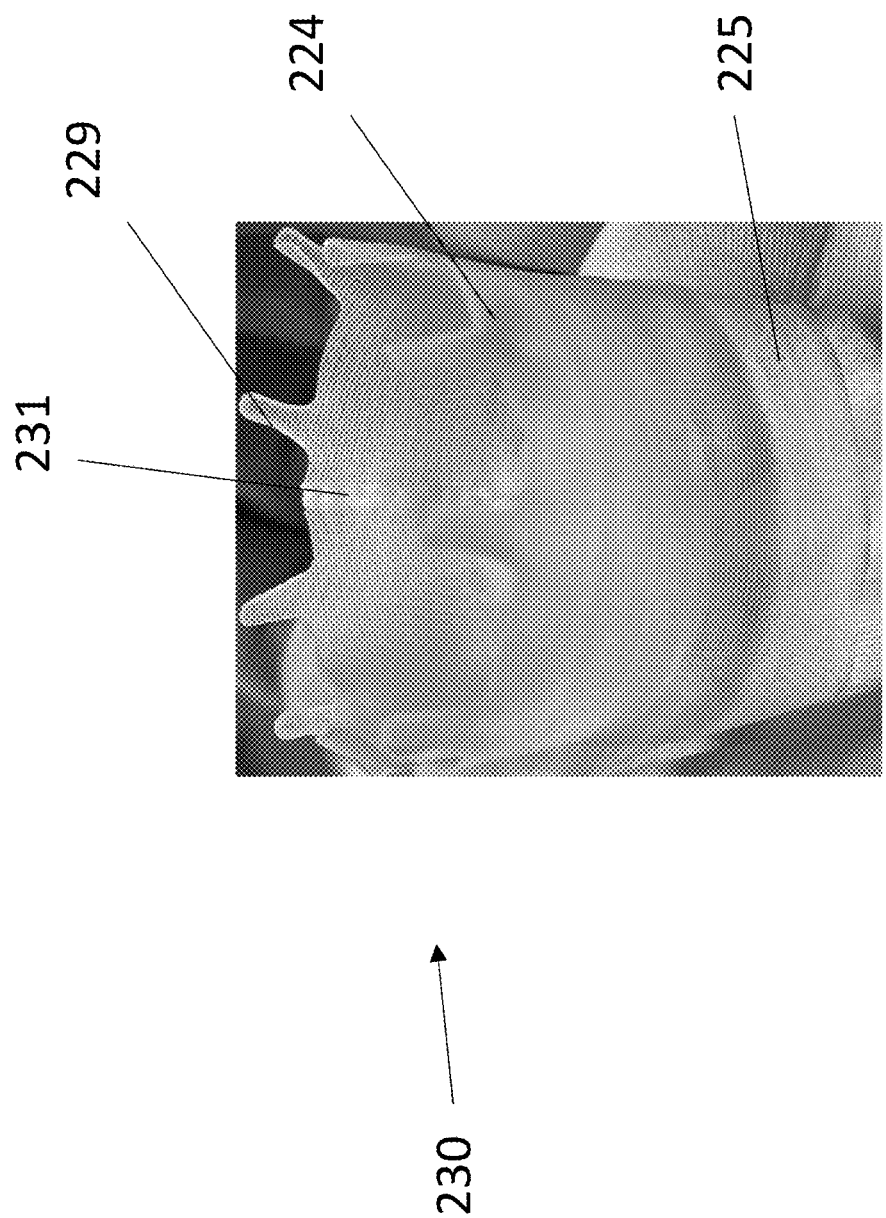
FIGS. 28-29 illustrate a frame with a unitary skirt.

Referring to FIG. 28, in some embodiments, the atrial and ventricular external skirts 224, 225 can be part of a single unitary skirt 230. The single unitary skirt 230 can advantageously help prevent bunching and/or folding that may occur with two separate skirts. In some embodiments, the single unitary skirt 230 can be manufactured from a flat sheet of knitted material that is laser cut and sewn together (e.g., along seam 231). In this embodiment, the cylindrical single unitary skirt 230 can then be dip coated and shape set over a mandrel. In other embodiments, the single unitary skirt 230 can be manufactured from a tube knit fabric. In this embodiment, the tube knit fabric can be slid over a mandrel, dip coated, and then laser cut into a pattern while still positioned on the mandrel. This embodiment can advantageously form a seamless single unitary skirt 230.

Figure 29:
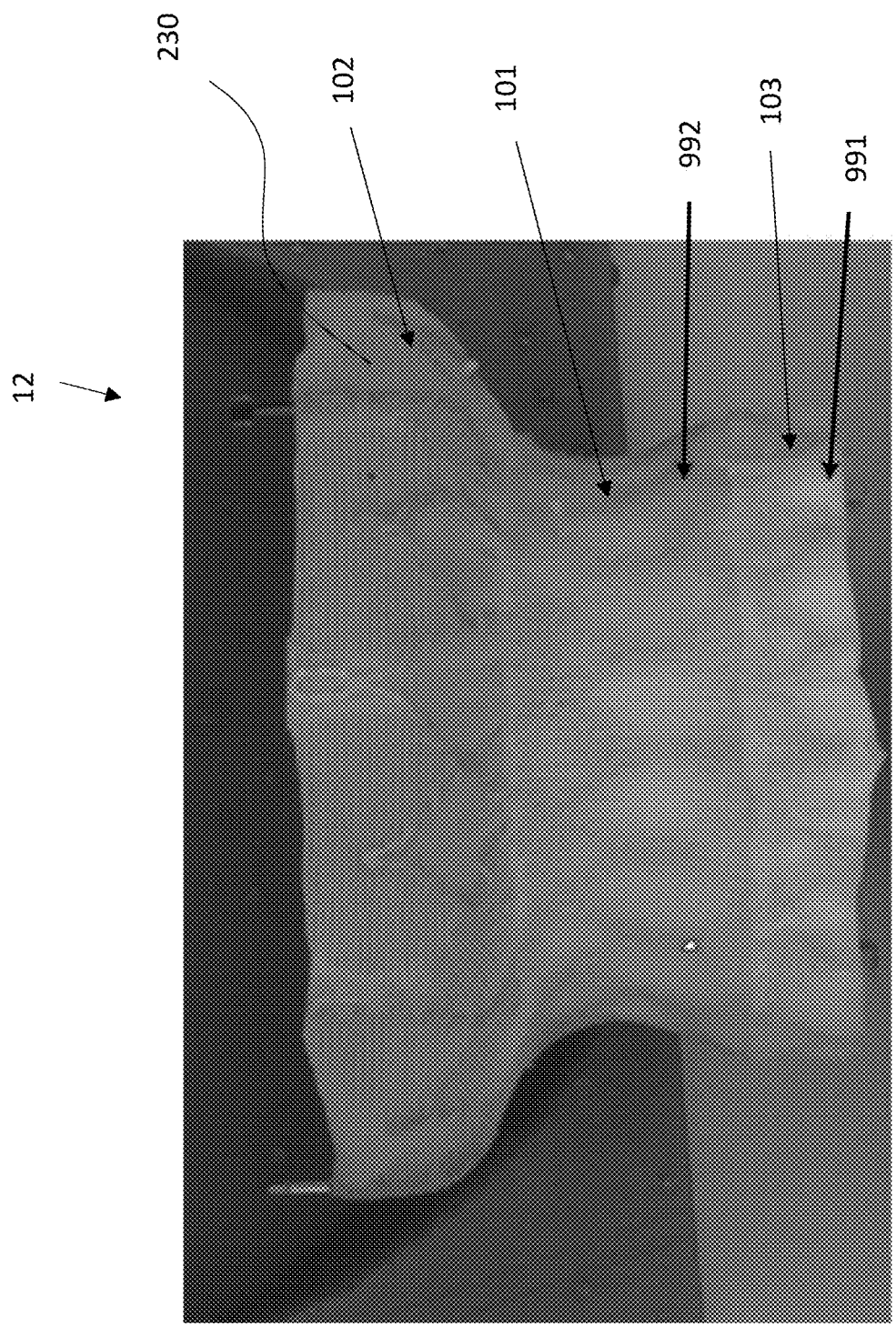

Referring to FIG. 29, in some embodiments, the frame can include a unitary skirt 230 (e.g., as described with respect to FIG. 28) with additional layers along a portion of the frame 12. For example, the single unitary skirt 230 can be layered with an additional ventricular skirt section 991 positioned along the distal-most struts of the frame 12 and/or folded thereover. The additional ventricular skirt section can advantageously help reduce trauma to the native valve (e.g., to the chordae). The single unitary skirt 230 can additionally or alternatively be layered with an additional skirt section 992 at the central annular portion 101, which can help prevent damage to the native leaflets.

The skirts described herein can be made of a polymer, such as polyethylene terephthalate (PET). Further, the skirts described herein can be woven and/or knitted (e.g., with a denier of 15-25, such as approximately 20). For example, FIG. 30A shows a frame 12 having a woven atrial external skirt 224 and a knitted ventricular external skirt 225. In contrast, FIG. 30B shows a frame 12 having a knitted unitary skirt 230.

Any of the skirts described herein can include a coating, such as a chronoflex AR coating, to reduce the pore size of the skirt and increase resistance to fluid flow therethrough. For example, in some embodiments, only the external atrial skirt 224 can include a coating thereon. In other embodiments, both the external and atrial skirts 224, 225 (either individual or unitary) can include a coating thereon.

As described herein, the valve prosthesis may include a frame structure (e.g., with a tapered waist and atrial and ventricular flared portions) with leaflets therein. In some embodiments, the leaflets can be formed of multi-layered materials for preferential function. The leaflets may be attached directly to the frame structure. Alternatively, the leaflets may be attached to an intermediate valve structure that is in turn connected to the frame structure. The leaflets may be connected to the frame structure before or after the frame structure has been deployed adjacent a native valve. The leaflets may comprise a biocompatible one-way valve. Flow in one direction may cause the leaflets to deflect open and flow in the opposite direction may cause the leaflets to close. The frame structure may be configured like a stent. The frame structure may, for example, comprise a scaffold in a diamond pattern formed from a shape memory material (e.g., nitinol, NiTi). One of ordinary skill in the art will appreciate that many other structures, materials, and configurations may be employed for the frame structure. For example, the frame structure may be formed of a polymer of sufficient elasticity. The frame structure may be formed of a combination of metal and polymer, such as metal (e.g., shape memory material) covered in polymer. The frame structure may include a variety of patterns besides diamond shapes. In some embodiments, the frame structure is a closed frame such that blood flow is forced through the leaflets therein. One or more skirts and/or seals may help force blood through the leaflets. Exemplary frame structures and valve prostheses are described in PCT Application No. PCT/US2019/047542, filed Aug. 21, 2019, titled "PROSTHETIC CARDIAC VALVE DEVICE, SYSTEMS, AND METHODS," now PCT Publication No. WO 2020/041495 in International Patent Application No. PCT/US2020/027744, filed Apr. 10, 2020, titled "MINIMAL FRAME PROSTHETIC CARDIAC VALVE DELIVERY DEVICES, SYSTEMS, AND METHODS," now PCT Publication No. WO 2020/210685, and in International Patent Application No. PCT/US2021/037661, filed Jun. 16, 2021, titled "MINIMAL FRAME PROSTHETIC CARDIAC VALVE DELIVERY DEVICES, SYSTEMS, AND METHODS," the entireties of which are incorporated by reference herein.

Additionally, in some embodiments, the valve prostheses described herein include one or more anchors. The anchor may include a flat spiral shape with a plurality of windings or loops spiraling radially outwards from a central point. The loops of the flat spiral shaped anchor may be generally positioned within the same plane. The anchor may be formed from a shape memory material (e.g., NiTi). The anchor can be configured to extend around the chordae of the valve (e.g., the mitral valve) and around the valve prosthesis to hold the valve prosthesis in place. Flat spiral anchors are described in U.S. patent application Ser. No. 16/723,537, filed Dec. 20, 2019, titled "PROSTHETIC CARDIAC VALVE DEVICES, SYSTEMS, AND METHODS," now U.S. Publication No. US-2020-0261220-A1, the entirety of which is incorporated by reference herein.

The valve prostheses and/or anchors described herein may be delivered via a delivery system. Exemplary delivery systems are described in International Application No. PCT/US2020/023671, filed Mar. 19, 2020, titled "PROSTHETIC CARDIAC VALVE DEVICES, SYSTEMS, AND METHODS," now PCT Publication No. WO 2020/191216, and in International Application No. PCT/US2021/040623, filed Jul. 7, 2021, titled "VALVE DELIVERY SYSTEM," the entireties of which are incorporated by reference herein.

It should be understood that any feature described herein with respect to one embodiment can be substituted for or combined with any feature described with respect to another embodiment. For example, it should be understood that any of the frame structures, features of the frame structures (e.g., commissure attachment mechanisms), or skirts described with respect to one embodiment can be interchanged and/or combined with any of the other frame structures described herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A device for treating a diseased native valve in a patient, the device comprising:
    a frame structure comprising an inflow portion, a central annular portion having a first circular cross-section with a first inner diameter, and a flared outflow portion that has a second circular cross-section with a second inner diameter larger than the first inner diameter of the central annular portion;
    a valve segment positioned radially within the frame structure and extending from the central annular portion to the flared outflow portion, the valve segment comprising a plurality of leaflets; and
    a plurality of commissure attachment mechanisms coupling the plurality of leaflets to the frame structure, each commissure attachment mechanism extending radially and bending inwards approximately 180 degrees from an outflow end of the frame structure to align with the first inner diameter such that the plurality of leaflets form a cylindrical flow path from the central annular portion to the plurality of commissure attachment mechanisms for blood passing therethrough.

2. The device of claim 1, wherein an inflow edge of the valve segment is unsupported by the frame structure.

3. The device of claim 2, wherein the inflow edge is spaced radially inwards from an inflow end of the frame structure.

4. The device of claim 1, wherein an inflow end of the frame structure is flared radially outwards.

5. The device of claim 1, wherein tips of the outflow end point substantially axially.

6. The device of claim 1, wherein the plurality of commissure attachment mechanisms each comprise a paddle, each of the paddles including a slot therein through which tabs of the plurality of leaflets pass.

7. The device of claim 6, wherein the paddle further comprises a plurality of holes therethrough for sewing attachment of the tabs to the paddle.

8. The device of claim 1, wherein the plurality of commissure attachment mechanisms each include a post that attaches to the outflow end of the frame structure and curves radially inwards.

9. The device of claim 8, wherein the post attaches to a strut of the outflow end, and wherein a thickness of the post is greater than a thickness of the strut.

10. The device of claim 1, wherein the gap is between 1.5 mm and 4 mm when the plurality of leaflets are fully opened.

11. The device of claim 1, wherein the plurality of leaflets are unsupported except at the commissure attachment mechanisms.

12. The device of claim 1, further comprising a spiral anchor configured to be placed around the central annular portion of the frame structure.

13. The device of claim 12, wherein the frame structure comprises a plurality of struts, and wherein the struts are configured to create an area of flexibility within the central annular portion of the frame structure.

14. The device of claim 1, wherein each commissure attachment mechanism is integrally formed with the frame structure.

15. The device of claim 1, wherein the plurality of commissure attachment mechanisms extend radially inwards to point towards an inflow direction of the frame structure, wherein the outflow end of the frame structure further comprises a plurality of tips that point towards an outflow direction of the frame structure.

16. The device of claim 1, wherein the plurality of commissure attachment mechanisms comprises up to three commissure attachment mechanisms.

17. The device of claim 1, wherein commissures of the plurality of leaflets are directly attached to the plurality of commissure attachment mechanisms.

18. A device for treating a diseased native valve in a patient, the device comprising:
a frame structure comprising a central annular portion having a first circular cross-section with a first inner circumference, an inflow portion, and an outflow portion, wherein the outflow portion is flared radially outwards relative to the central annular portion such that it has a second circular cross-section with a second inner circumference that is larger than the first inner circumference;
a valve segment positioned radially within the frame structure, the valve segment comprising a plurality of leaflets; and
a plurality of commissure attachment mechanisms coupling the plurality of leaflets to the outflow portion of the frame structure, each commissure attachment mechanism extending radially inwards such that a third inner circumference formed by the commissure attachment mechanisms is equal to the first inner circumference of the central annular portion.

19. The device of claim 18, wherein an inflow edge of the valve segment is unsupported by the frame structure.

20. The device of claim 19, wherein the inflow edge is spaced radially inwards from the inflow portion of the frame structure.

21. The device of claim 18, wherein the inflow portion of the frame structure is flared radially outwards.

22. The device of claim 18, wherein the outflow portion further comprises tips that point substantially axially in an outflow direction of the frame structure.

23. The device of claim 22, wherein the plurality of commissure attachment mechanisms further comprise second tips that point substantially axially in an inflow direction of the frame structure.

24. The device of claim 18, wherein the plurality of commissure attachment mechanisms comprises up to three commissure attachment mechanisms.

25. The device of claim 18, wherein commissures of the plurality of leaflets are directly attached to the plurality of commissure attachment mechanisms.

* * * * *